US006593330B2

(12) United States Patent
Nilsson

(10) Patent No.: US 6,593,330 B2
(45) Date of Patent: Jul. 15, 2003

(54) COMPOUNDS AND THEIR USE

(75) Inventor: Björn M. Nilsson, Uppsala (SE)

(73) Assignee: Biovitrum (SE)

( * ) Notice: Subject to any disclaimer, the term of this patent is extended or adjusted under 35 U.S.C. 154(b) by 0 days.

(21) Appl. No.: 09/989,358

(22) Filed: Nov. 20, 2001

(65) Prior Publication Data

US 2002/0147200 A1 Oct. 10, 2002

Related U.S. Application Data

(60) Provisional application No. 60/253,509, filed on Nov. 28, 2000.

(30) Foreign Application Priority Data

Nov. 20, 2000 (SE) .............................. 0004245

(51) Int. Cl.$^7$ .................... C07D 401/04; A01K 31/496; A61P 3/04; A61P 25/06; A61P 25/08

(52) U.S. Cl. .................................. 514/252.11; 544/357

(58) Field of Search ...................... 544/357; 514/252.11

(56) References Cited

U.S. PATENT DOCUMENTS

| 3,253,989 A | 5/1966 | Moser et al. ................. 167/55 |
| 4,078,063 A | 3/1978 | Lumma, Jr. et al. ......... 260/268 |
| 4,081,542 A | 3/1978 | Lumma, Jr. et al. ......... 260/268 |

FOREIGN PATENT DOCUMENTS

| DK | 2202385 A1 | 1/1972 |
| EP | 0226842 A2 | 7/1987 |
| EP | 0330263 A1 | 2/1988 |
| EP | 0345808 A1 | 12/1989 |
| EP | 0370560 B1 | 5/1990 |
| EP | 0462638 A1 | 12/1991 |
| EP | 0572863 A1 | 12/1993 |
| EP | 0580465 A1 | 1/1994 |
| EP | 0655440 A2 | 5/1995 |
| EP | 0657426 A2 | 6/1995 |
| EP | 0657426 A3 | 3/1996 |
| EP | 0655440 A3 | 11/1996 |
| EP | 0863136 A1 | 9/1998 |
| EP | 1023898 A1 | 8/2000 |
| ES | 514549 A1 | 7/1982 |
| JP | 07300474 A2 | 11/1995 |
| WO | WO 87/04928 A1 | 8/1987 |
| WO | WO 95/01976 A1 | 1/1995 |
| WO | WO 96/11920 A1 | 4/1996 |
| WO | WO 98/30548 A1 | 7/1998 |
| WO | WO 98/42712 A1 | 10/1998 |
| WO | WO 98/56768 A1 | 12/1998 |
| WO | WO 99/11619 A1 | 3/1999 |
| WO | WO 99/58490 A3 | 11/1999 |
| WO | WO 99/58490 A2 | 11/1999 |
| WO | WO 0012475 A1 | 3/2000 |
| WO | WO 0012481 A3 | 3/2000 |
| WO | WO 0012481 A2 | 3/2000 |
| WO | WO 00/12482 A3 | 3/2000 |
| WO | WO 00/12482 A2 | 3/2000 |
| WO | WO 00/12502 A1 | 3/2000 |
| WO | WO 00/12510 A1 | 3/2000 |
| WO | WO 00/17163 A1 | 3/2000 |
| WO | WO 00/17170 A2 | 3/2000 |
| WO | WO 00/35922 A1 | 6/2000 |
| WO | WO 00/44737 A1 | 8/2000 |
| WO | WO 00/44753 A1 | 8/2000 |
| WO | WO 00/50401 A1 | 8/2000 |
| WO | WO 00/76984 A2 | 12/2000 |
| WO | WO 00/76984 A3 | 12/2000 |
| WO | WO 00/77002 A1 | 12/2000 |
| WO | WO 00/77010 A2 | 12/2000 |
| WO | WO 01/77001 A1 | 12/2000 |
| WO | WO 01/09111 A1 | 2/2001 |
| WO | WO 01/09122 A3 | 2/2001 |
| WO | WO 01/09122 A2 | 2/2001 |
| WO | WO 01/09123 A1 | 2/2001 |
| WO | WO 01/09126 A1 | 2/2001 |
| WO | WO 01/12602 A1 | 2/2001 |
| WO | WO 01/12603 A1 | 2/2001 |

OTHER PUBLICATIONS

Campbell et al., Simon F., "2,4–Diamino–6,7–dimethoxyquinazolines. 3. 2–(4–Heterocyclylpiperasin–1–yl) Derivatives as $\alpha_1$–Adrenoceptor Antagonists and Antihypertensive Agents", *J. Med. Chem.*, vol. 30, pp. 1794–1798, 1987.

Dourish, Colin T., "Multiple Serotonin Receptors: Opportunities for New Treatments for Obesity?", *Obesity Research*, vol. 3, Suppl. 4, pp. 449S–462S, 1995.

Dukat et al., Malgorzata, "Structure–Activity Relationships fo rthe Binding of Arylpiperazines and Arylbiguanides at 5–HT$_3$ Serotonin Receptors", *J. Med. Chem.*, vol. 39, pp. 4017–4026, 1996.

Jenck et al., F., "The role of 5–HT$_{2c}$ receptors in affective disorders", *Exp. Opin. Invest. Drugs*, pp. 1587–1599, 1998.

Kennett, GA, "5–HT drugs and eating disorders", *IDrugs*, vol. 1, No. 4, pp. 456–470, 1998.

Lee et al., Hong Shick, "Effect of the Serontonin Agonist, MK–212, on the Body Temperature in Schizophrenia", *Society of Biological Phychiatry*, vol. 31, pp. 460–470, 1992.

(List continued on next page.)

Primary Examiner—Richard L. Raymond
Assistant Examiner—Venkataraman Balasubramanian
(74) Attorney, Agent, or Firm—Fish & Richardson P.C.

(57) ABSTRACT

A compound of the general formula (I):

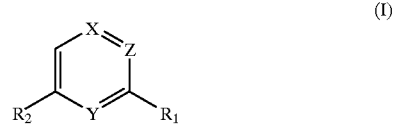

wherein $R_1$, $R_2$, X, Y and Z are as described in the specification.

30 Claims, No Drawings

OTHER PUBLICATIONS

Leysen, Dirk C.M., "Selective 5–HT$_{2c}$ agonists as potential antidepressants", *IDrugs,* vol. 2(2), pp. 109–120, 1999.

Lumma et al., Jr., William C., "Piperazinylpyrazines with Central Serotoninmimetic Activity", *Journal of Medicinal Chemistry,* vol. 21, No. 6, pp. 536–542, 1978.

Lumma, Jr. et al., William C., "Piperazinylquinoxalines with Central Serotoninmimetic Activity", *J. Med. Chem.,* vol. 24, pp. 93–101, 1981.

Meltzer, Herbert Y., "Clinical studies on the mechanism of action of clozapine: the dopamine–serotonin hypothesis of schizophrenia", *Psychopharmacology,* pp. S18–S27, 1989.

Methvin et al., Isaac, "Pyrrolo[3,2,2–ij] quinoline Derivatives, a 5–HT$_{2c}$ Receptor Agonist with Selectivity over the 5–HT$_{2a}$ Receptor: Potential Therapeutic Applications for Epilepsy and Obesity", *Biiorganic & Medicinal Chemistry Letters,* vol. 10, pp. 919–921, 2000.

Pavia et al., Michael R., "6–Alkyl–N, N–disubstrituted–2–pyridinamines as Anticonvulsant Agents", *J. Med. Chem.,* vol. 30., pp. 1210–1214, 1987.

Pavia et al., Michael R., "6–Alkoxy–N, N–disubstrituted–2–pyridinamines as Anticonvulsant Agents", *J. Med. Chem.,* vol. 32, pp. 1237–1242, 1989.

Rogers et al., R.J., "Differential Effects of Novel Ligands for 5–HT Receptor Subtypes on Nonopioid Defensive Analgesia in Male Mice", *Neuroscience & Biobehavioral Reviews,* vol. 15, pp. 489–495, 1991.

Roth et al., Bryan L., "The Multiplicity of Serontonin Receptors: Uselessly Diverse Molecules or an Embarrassment of Riches?", *The Neuroscientist,* pp. 252–262, 2000.

Sargent et al., P.A., "5–HT$_{2c}$ receptor activation decreases appetite and body weight in obese subjects", *Psychopharmacology,* vol. 133, pp. 309–312, 1997.

Shutske et al., Gregory M., "Synthesis of Some Piperazinylpyrazolo[3,4–b]pyridines as Selective Serotonin Re–uptake Inhibitors", *J. Heterocylic Chem.,* vol. 34, pp. 789–795, 1997.

Tecott et al., Laurence H., "Eating disorder and epilepsy in mice lacking 5–HT$_{2c}$ serotonin receptors", *Nature,* vol. 374, pp. 542–546, 1995.

COMPOUNDS AND THEIR USE

CROSS REFERENCE TO RELATED APPLICATIONS

This application claims priority from Swedish Patent Application No. 0004245-7, filed Nov. 20, 2000 and U.S. Provisional Patent Application Ser. No. 60/253,509, filed Nov. 28, 2000. These applications are incorporated herein by reference in their entirety.

FIELD OF THE INVENTION

The present invention relates to novel compounds, to pharmaceutical compositions comprising the compounds, to processes for their preparation, as well as to the use of the compounds for the preparation of a medicament which particularly acts on the central nervous system.

BACKGROUND OF THE INVENTION

Many diseases of the central nervous system are influenced by the adrenergic, the dopaminergic, and the serotonergic neurotransmitter systems. For example, serotonin has been implicated in a number of diseases and conditions which originate in the central nervous system. A number of pharmacological and genetic experiments involving receptors for serotonin strongly implicate the 5-$HT_{2c}$ receptor subtype in the regulation of food intake (Obes. Res. 1995, 3, Suppl. 4, 449S–462S). The 5-$HT_{2c}$ receptor subtype is transcribed and expressed in hypothalamic structures associated with appetite regulation. It has been demonstrated that the 5-$HT_{2c}$ receptor agonist m-chlorophenylpiperazine (mCPP), which has some preference for the 5-$HT_{2c}$ receptor, reduces food intake in mice that express the normal 5-$HT_{2c}$ receptor while the compound lacks activity in mice expressing the mutated inactive form of the 5-$HT_{2c}$ receptor (Nature 1995, 374, 542–546). In a recent clinical study, a slight but sustained reduction in body weight was obtained after 2 weeks of treatment with mCPP in obese subjects (Psychopharmacology 1997, 133, 309–312). Recently, a series of pyrrolo[3,2,1-ij]quinoline derivatives was identified to be 5-$HT_{2c}$ receptor agonists having selectivity over the 5-$HT_{2A}$ receptor (Isaac M., et al., Bioorg. Med. Chem. Lett. 2000, 10, 919–921). The compounds are said to offer a novel approach to the treatment of obesity and epilepsy.

Weight reduction has also been reported from clinical studies with other "serotonergic" agents (see e.g. IDrugs 1998, 1, 456–470). For example, the 5-HT reuptake inhibitor fluoxetine and the 5-HT releasing agent/reuptake inhibitor dexfenfluramine have exhibited weight reduction in controlled studies. However, currently available drugs that increase serotonergic transmission appear to have only a moderate and, in some cases, transient effects on the body weight.

The 5-$HT_{2c}$ receptor subtype has also been suggested to be involved in CNS disorders such as depression and anxiety (Exp. Opin. Invest. Drugs 1998, 7, 1587–1599; IDrugs, 1999, 2, 109–120).

The 5-$HT_{2c}$ receptor subtype has further been suggested to be involved in urinary disorders such as urinary incontinence (IDrugs, 1999, 2, 109–120).

Compounds which have a selective effect on the 5-$HT_{2c}$ receptor may therefore have a therapeutic potential in the treatment of disorders like those mentioned above. Of course, selectivity also reduces the potential for adverse effects mediated by other serotonin receptors.

Information Disclosure

U.S. Pat. No. 3,253,989 discloses the use of mCPP as an anorectic agent.

EP-A1-863 136 discloses azetidine and pyrrolidine derivatives which are selective 5-$HT_{2c}$ receptor agonists having antidepressant activity and which can be used for treating or preventing serotonin-related diseases, including eating disorders and anxiety.

EP-A1-330 263 discloses piperazinylalkylpyrimidines as hypoglycemic agents.

WO 87/04928 discloses 2-(1-piperazinyl)pyrimidines as agents for treating neuropathy.

EP-A2-226842 discloses 1,4-naphthalenedione heterocyclic derivatives as antiallergics and antiasthmatics including 2-(3-bromophenyl)-4-(1-piperazinyl)-pyrimidine.

EP-A-657 426 discloses tricyclic pyrrole derivatives having activity on the 5-$HT_{2c}$ receptor and which inter alia may be used for treating eating disorders.

EP-A-655 440 discloses 1-aminoethylindoles having activity on the 5-$HT_{2c}$ receptor and which may be used for treating eating disorders.

EP-A-572 863 discloses pyrazinoindoles having activity on the 5-$HT_{2c}$ receptor and which may be used for treating eating disorders.

J. Med. Chem. 1978, 21, 536–542 and U.S. Pat. No. 4,081,542 disclose a series of piperazinylpyrazines having central serotonin-mimetic activity.

U.S. Pat. No. 4,078,063 discloses a series of piperazinylpyridines having anorexic activity.

J. Med. Chem. 1981, 24, 93–101 discloses a series of piperazinylquinoxalines with central serotoninmimetic activity.

ES 514549 discloses piperazine derivative with anorexigenic action.

EP 370560 discloses 1-[mono- or bis(trifluoromethyl)-2-pyridinyl]piperazines as central nervous system agents.

J. Med. Chem. 1987, 30, 1794–1798 discloses 2-(4-heterocyclylpiperazin-1-yl) derivatives including 2-phenoxy-4-piperazin-1-ylpyrimidine.

DE 2202385 discloses antimicrobial (5-nitro-2-furyl) pyrimidines and -thiadiazoles including 2-(5-nitro-2-furyl)-4-(4-methyl-1-piperazinyl)pyrimidine and 2-(5-nitro-2-furyl)-4-[4-(2-hydroxyethyl)-1-piperazinyl]pyrimidine.

J. Med Chem. 1987, 30, 1210–1214 discloses N,N-disubstituted 6-alkoxy-2-pyridinamines as anticonvulsant agents including 1-(6-methoxy-2-pyridinyl)piperazine, 1-(6-ethoxy-2-pyridinyl)piperazine, 1-(6-isopropoxy-2-pyridinyl)piperazine, 1-(6-isobutoxy-2-pyridinyl)piperazine, 1-(6-cyclopropylmethoxy-2-pyridinyl)piperazine, 1-(6-cyclohexylmethoxy-2-pyridinyl)piperazine, and 1-(6-cyclohexyloxy-2-pyridinyl)piperazine.

J. Med. Chem. 1989, 32, 1237–1242 discloses 6-alkyl-N,N-disubstituted-2-pyridinamines as anticonvulsant agents including 1-(6-butylthio-2-pyridinyl)piperazine, 1-(6-cyclohexylmethyl-2-pyridinyl)piperazine and 1-[6-(2-phenylethyl)-2-pyridinyl]piperazine.

JP 07300474 discloses drugs for treatment of diseases related to serotoninergic nerve including 1-(6-phenoxy-2-pyridinyl)piperazine and 1-[6-(substituted)phenoxy-2-pyridinyl]piperazines, 1-(6-benzyloxy-2-pyridinyl) piperazine, 1-(6-cyclobutyloxy-2-pyridinyl)piperazine, and 1-(6-cyclopentyloxy-2-pyridinyl)piperazine EP 580465 discloses heterocyclic piperazines as 5-HT$_3$ agonists including 6-chloro-2-(3-methylpiperazinyl)pyridine and 6-chloro-2-(4-methylpiperazinyl)pyridine.

WO 00/12475 discloses indoline derivatives as 5-HT$_{2b}$ and/or 5-HT$_{2c}$ receptor ligands, especially for the treatment of obesity.

WO 00/12510 discloses pyrroloindoles, pyridoindoles and azepinoindoles as 5-HT$_{2c}$ receptor agonists, particularly for the treatment of obesity.

WO 00/12482 discloses indazole derivatives as selective, directly active 5-HT$_{2c}$ receptor ligands, preferably 5-HT$_{2c}$ receptor agonists, particularly for use as anti-obesity agents.

WO 00/12502 discloses pyrroloquinolines as 5-HT$_{2c}$ receptor agonists, particularly for use as anti-obesity agents.

WO 00/35922 discloses 2,3,4,4a-tetrahydro-1H-pyrazino[1,2-a]quinoxalin-5(6H)ones as 5HT$_{2c}$ agonists, which may be used for the treatment of obesity.

WO 00/44737 discloses aminoalkylbenzofurans as 5-HT$_{2c}$ agonists, which may be used for the treatment of obesity.

Further compounds reported to be 5HT$_{2c}$ receptor agonists are, for example, indazolylpropylamines of the type described in WO 00/12481; indazoles of the type described in WO 00/17170; piperazinylpyrazines of the type described in WO 00/76984; heterocycle fused γ-carbolines of the type described in WO 00/77001, WO 00/77002 and WO 00/77010; benzofurylpiperazines of the type described in WO 01/09111 and WO 01/09123; benzofurans of the type described in WO 01/09122; benzothiophenes of the type described in 01/09126; aminoalkylindazoles of the type described in WO 98/30548; indoles of the type described in WO 01/12603; indolines of the type described in WO 01/12602; pyrazino(aza)indoles of the type described in WO 00/44753 and tricyclic pyrroles or pyrazoles of the type described in WO 98/56768.

WO 96/11920 discloses CNS-active pyridinylurea derivatives.

WO 95/01976 discloses indoline derivatives active as 5-HT$_{2c}$ antagonists and of potential use in the treatment of CNS disorders.

WO 99/58490 disloses aryl-hydronaphthalenalkanamines which may effectuate partial or complete blockage of serotonergic 5-HT$_{2c}$ receptors in an organism.

SUMMARY OF THE INVENTION

According to the invention novel compounds of the general formula (I) are provided:

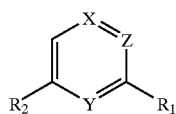
(I)

wherein (i) X and Y represent both nitrogen and Z represents CH, forming a pyrazine derivative, or (ii) X and Z represent both CH and Y represents nitrogen, forming a pyridine derivative, or (iii) X represents C-CF$_3$, Z represents CH, and Y represents nitrogen, forming a 4-trifluoromethylpyridine derivative, or (iv) Y and Z represent both nitrogen and X represents CH, forming a pyrimidine derivative, and wherein R$_1$ and R$_2$ are each, independently, selected from a group A, consisting of

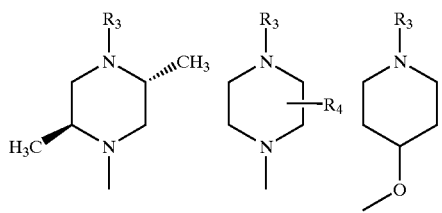

or from a group B, consisting of aryl-C$_1$–C$_6$-alkyl, aryl-C$_1$–C$_6$-alkoxy, heteroaryl-C$_1$–C$_6$-alkoxy, aryloxy-C$_2$–C$_6$-alkoxy, heteroaryloxy-C$_2$–C$_6$-alkoxy, 1-indanyloxy, 2-indanyloxy, aryloxy, heteroaryloxy, arylthio, heteroarylthio, C$_5$–C$_6$-cycloalkylthio, C$_5$–C$_8$-alkoxy, C$_5$–C$_8$-alkylthio, C$_3$–C$_6$-alkynyloxy, C$_3$–C$_6$-alkenyloxy, fluoro-C$_2$–C$_4$-alkoxy, C$_4$–C$_8$-cycloalkyloxy, C$_3$–C$_8$-cycloalkyl-C$_1$–C$_4$-alkoxy, halogen, aryl-C$_1$–C$_4$-alkylthio, heteroaryl-C$_1$–C$_4$-alkylthio, aryl-C$_1$–C$_4$-alkylamino, heteroaryl-C$_1$–C$_4$-alkylamino, heteroaryl and aryl;

with the proviso that:

(i) R$_1$ and R$_2$ are different and are not both selected from group A or group B at the same time;

(ii) when formula (I) is a pyrazine derivative R$_1$ or R$_2$ are other than, phenylthio, phenylmethylthio, phenyl or phenyl substituted by halogen;

(iii) R$_1$ in formula (I) is halogen, especially chloro, only when (I) is a pyrazine derivative and when R$_2$ simultaneously is 2-methylpiperazin-1-yl, 2-ethylpiperazin-1-yl or trans-2,5-dimethylpiperazin-1-yl;

(iv) when formula (I) is a pyrazine derivative and R$_1$ is 4-piperidinyloxy, R$_2$ is other than 3-pyridinylmethoxy, 4-quinolinylmethoxy, 2,4-dimethoxybenzyloxy and 3-(4-pyridinyl)propoxy;

(v) when both X and Z are CH and Y is N in formula (I), forming a pyridine derivative, and R$_1$ is 1-piperazinyl or 4-methylpiperazin-1-yl, then R$_2$ is other than, 2-phenylethyl, benzyloxy, benzylamino, phenylthio, phenoxy, substituted phenoxy, C$_4$–C$_8$-cycloalkyloxy and C$_3$–C$_8$-cycloalkylmethoxy;

(vi) when X is CH and Z and Y both are nitrogen in formula (I), forming a pyrimidine derivative, and R$_2$ is 1-piperazinyl, then R$_1$ is other than phenoxy, phenyl or phenyl substituted by bromo, and C$_5$–C$_8$ alkoxy; and when R$_2$ is 4-methylpiperazin-1-yl or 4-(2-hydroxyethyl)piperazin-1-yl, then R$_1$ is other than 5-nitro-2-furyl;

(vii) when X is CH and Z and Y both are nitrogen in formula (I), forming a pyrimidine derivative, and R$_1$ is 1-piperazinyl, then R$_2$ is other than C$_5$–C$_8$ alkoxy;

and where

R$_3$ is H or C$_{1-4}$-alkyl, allyl, 2-hydroxyethyl, or 2-cyanoethyl, or a nitrogen protecting group, or a prodrug moiety such as an acyl- or an alkoxycarbonyl group forming a cleavable amide or carbamate linkage;

R$_3$ is preferably hydrogen;

R$_4$ is hydrogen or C$_{1-4}$ alkyl, preferably hydrogen, methyl or ethyl, more preferably hydrogen or methyl;

and wherein any aryl or heteroaryl residue, alone or as part of another group, in R$_1$ or R$_2$ may be independently substituted in one or more positions, preferably one or two, by C$_{1-4}$ alkyl, C$_{1-4}$-alkoxy, C$_{1-4}$-alkylthio, C$_{2-4}$-acyl, C$_{1-4}$-alkylsulphonyl, cyano, nitro, hydroxy, C$_{2-6}$-alkenyl, C$_{2-6}$-alkynyl, fluoromethyl, trifluoromethyl, trifluoromethoxy, halogen, —N(R$_5$)(R$_6$), aryl, aryloxy, arylthio, aryl-C$_{1-4}$-alkyl, aryl-C$_{2-4}$-alkenyl, aryl-C$_{2-4}$-alkynyl, heteroaryl, heteroaryloxy, heteroarylthio or heteroaryl-C$_{1-4}$-alkyl, aryl-C$_{1-4}$-alkoxy, aryloxy-C$_{1-4}$-alkyl, dimethylamino-C$_{2-4}$-alkoxy;

and wherein any aryl or heteroaryl residue as substituents on aryl or heteroaryl, alone or as part of another group, in R$_1$ or R$_2$ in turn may be substituted in one or more positions, preferably one, independently of each other by C$_{1-4}$-alkyl, C$_{1-4}$-alkoxy, halogen, trifluoromethyl, cyano, hydroxy or dimethylamino; and R$_5$ and R$_6$ independently of each other are hydrogen, methyl or ethyl, or together with the nitrogen atom to which they are bound form a pyrrolidine, piperazine, morpholine, thiomorpholine or a piperidine ring;

and pharmaceutically acceptable salts, hydrates, geometrical isomers, tautomers, optical isomers, N-oxides and prodrug forms thereof.

When R$_3$ serves as a nitrogen protecting group R$_3$ is t-butoxycarbonyl (t-BOC), benzyl or trityl.

In case the compounds of formula (I) can be in the form of optical isomers, the invention comprises the racemic mixture as well as the individual enantiomers as such.

In case the compounds of formula (I) contain groups, which may exist in tautomeric forms, the invention comprises the tautomeric forms of the compounds as well as mixtures thereof.

In case the compounds of formula (I) can be in the form of geometrical isomers, the invention comprises the geometrical isomers as well as mixtures thereof.

According to another aspect, the invention provides the compounds according to formula (I) above for use in therapy.

Still another aspect of the invention provides a pharmaceutical composition comprising a compound according to formula (I) above as the active ingredient, preferably together with a pharmaceutically acceptable carrier and, if desired, other pharmacologically active agents.

In yet another aspect, the invention provides a method for the treatment of a human or animal subject suffering from a serotonin-related disease, particularly 5-HT$_{2c}$ receptor-related, especially eating disorders, particularly obesity; memory disorders, schizophrenia, mood disorders, anxiety disorders, pain, substance abuse, sexual dysfunctions, epilepsy, and urinary disorders.

Another aspect of the invention provides for the use of the compounds according to formula (I) above for the manufacture of a medicament for the treatment of a serotonin-related disease, particularly 5-HT$_{2c}$ receptor-related, especially eating disorders, particularly obesity; memory disorders; schizophrenia, mood disorders, anxiety disorders, pain, substance abuse, sexual dysfunctions, epilepsy and urinary disorders.

Finally a method for modulating 5HT$_{2c}$ receptor function is an aspect of the invention.

DETAILED DESCRIPTION OF THE INVENTION

According to the present invention, a class of novel compounds has been developed which compounds bind to the 5-HT$_{2c}$ receptor (agonists and antagonists) and which therefore may be used for the treatment of serotonin-related disorders.

First, the various terms used, separately and in combinations, in the above definition of the compounds having the general formula (I) will be explained.

By "heteroatom" is meant nitrogen, oxygen, sulphur, and in heterocyclic rings (including heteroaromatic as well as saturated and partially saturated heterocyclic rings), also selenium.

The term "aryl" is intended to include aromatic rings (monocyclic or bicyclic) having from 6 to 10 ring carbon atoms, such as phenyl, 1-naphthyl, 2-naphthyl, 1,2,3,4-tetrahydronaphthyl (can be linked to the remainder of the molecule via a carbon atom in any ring) and indanyl (can be linked to the remainder of the molecule via a carbon atom in any ring).

The term "heteroaryl" means a mono- or bicyclic aromatic ring system, only one ring need be aromatic, and which can be linked to the remainder of the molecule via a carbon or nitrogen atom in any ring, and having from 5 to 10 ring atoms (mono- or bicyclic), in which one or more of the ring atoms are other than carbon, such as nitrogen, sulphur, oxygen and selenium. Examples of such heteroaryl rings are pyrrole, imidazole, thiophene, furan, thiazole, isothiazole, thiadiazole, oxazole, isoxazole, oxadiazole, pyridine, pyrazine, pyrimidine, pyridazine, pyrazole, triazole, tetrazole, chroman, isochroman, coumarin, quinoline, quinoxaline, isoquinoline, phthalazine, cinnoline, quinazoline, indole, isoindole, indoline, isoindoline, benzothiophene, benzofuran, 2,3-dihydrobenzofuran, isobenzofuran, benzoxazole, 2,1,3-benzoxadiazole, benzothiazole, 2,1,3-benzothiadiazole, 2,1,3-benzoselenadiazole, benzimidazole, indazole, 2,3-dihydro-1,4-benzodioxine, 1,3-benzodioxole, 1,2,3,4-tetrahydroquinoline, 3,4-dihydro-2H-1,4-benzoxazine, 1,5-naphthyridine, 1,8-naphthyridine, 3,4-dihydro-2H-pyrido[3,2-b]-1,4-oxazine, and 2,3-dihydro-1,4-benzoxathiine. If a bicyclic aryl or heteroaryl ring is substituted, it may be substituted in any ring.

Exemplary aryl-C$_1$–C$_6$-alkyl, in which the alkyl portion of the group may be straight or branched, include benzyl, 2-phenylethyl, 3-phenyl-1-propyl, 1-phenylethyl, 1-phenyl-2-propyl and the like.

Exemplary aryl-C$_1$–C$_6$-alkoxy, in which the alkyl portion of the group may be straight or branched, include benzyloxy, 2-naphthylmethoxy, 2-phenylethoxy, 3-phenyl-1-propoxy, 1-phenylethoxy, 1-phenyl-2-propoxy, 2-phenyl-1-propoxy and the like.

Exemplary aryloxy-C$_2$–C$_6$-alkoxy, in which the alkyl portion of the group may be straight or branched, include 2-phenoxyethoxy, 2-(1-naphthyloxy)ethoxy, 3-(2-naphthyloxy)-1-propoxy, 3-phenoxy-1-propoxy, 4-phenoxy-1-butoxy, 5-phenoxy-1-pentoxy, 1-phenoxy-2-propoxy and the like.

Exemplary C$_3$–C$_8$-cycloalkyl-C$_1$–C$_4$-alkoxy, in which the alkyl portion of the group may be straight or branched, include cyclopropylmethoxy, cyclopentylmethoxy, 2-cyclohexylethoxy, 1-cyclohexylethoxy, 1-cyclopropylethoxy, 1-cyclobutylethoxy and the like.

Exemplary heteroaryl-C$_1$–C$_4$-alkylamino include 2-(2-pyridinyl)ethylamino, 3-pyridinylmethylamino, 2-(2-thienyl)ethylamino, 2-(1H-indol-3-yl)ethylamino and the like.

Exemplary heteroaryloxy-C$_2$–C$_6$-alkoxy include 2-(8-quinolinyloxy)ethoxy, 2-(3-pyridinyloxy)ethoxy, 3-(8-quinolinyloxy)propoxy and the like Exemplary C$_3$–C$_6$-alkynyloxy include propargyloxy, 1-hexynyloxy, 2-hexynyloxy, 3-butynyloxy, 3-pentynyloxy and the like.

C$_{5-8}$-alkoxy may be straight or branched. Exemplary alkoxy groups include pentyloxy, isopentyloxy, hexyloxy, and isohexyloxy.

Halogen includes fluorine, chlorine or bromine.

Where it is stated above that aryl and heteroaryl residues may be substituted (in one or more postions), this applies to aryl and heteroaryl per se as well as to any combined groups containing aryl or heteroaryl residues, such as heteroaryloxy-$C_2$–$C_6$-alkoxy, heteroaryloxy, aryl-$C_1$–$C_6$-alkoxy etc.

The term "N-oxides" means that one or more nitrogen atoms, when present in a compound, are in N-oxide form (N→O).

The term "prodrug forms" means a pharmacologically acceptable derivative, such as a carbamate or an amide, which derivative is biotransformed in the body to form the active drug. Reference is made to Goodman and Gilman's, The Pharmacological basis of Therapeutics, $8^{th}$ ed., McGraw-Hill, Int. Ed. 1992, "Biotransformation of Drugs, p. 13–15.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Pharmaceutically acceptable salts" mean salts which are pharmaceutically acceptable, as defined above, and which possess the desired pharmacological activity. Such salts include acid addition salts formed with organic and inorganic acids, such as hydrogen chloride, hydrogen bromide, hydrogen iodide, sulfuric acid, phosphoric acid, acetic acid, glycolic acid, maleic acid, malonic acid, oxalic acid, toluenesulphonic acid, methanesulphonic acid, fumaric acid, succinic acid, tartaric acid, citric acid, benzoic acid, ascorbic acid and the like.

Preferred embodiments of the invention are:
a compound of formula (I) wherein X and Y represent both nitrogen and Z represents CH, forming a pyrazine derivative;
a compound of formula (I) wherein Y and Z both represent nitrogen and X represents CH, forming a pyrimidine derivative;
a compound of formula (I) wherein $R_1$ or $R_2$ is selected from

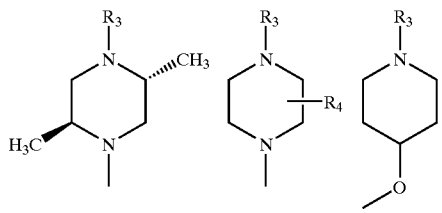

and wherein $R_3$ is hydrogen;
a compound of formula (I) wherein $R_1$ or $R_2$ is selected from

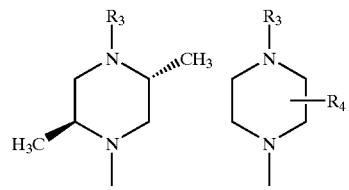

and where $R_3$ is hydrogen and $R_4$ is selected from hydrogen or methyl or ethyl;

a compound of formula (I) wherein $R_1$ or $R_2$ is

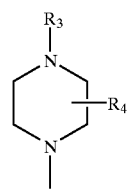

and where $R_3$ is hydrogen and $R_4$ is selected from hydrogen or methyl or ethyl; and
a compound of formula (I) wherein $R_1$ or $R_2$ is selected from

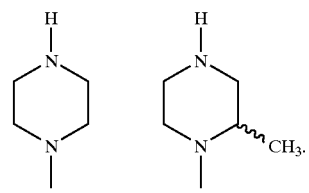

In a further preferred embodiment, the compounds of formula (I) are selected from compounds in which X and Y both are nitrogen and Z is CH giving pyrazine derivatives of formula (II):

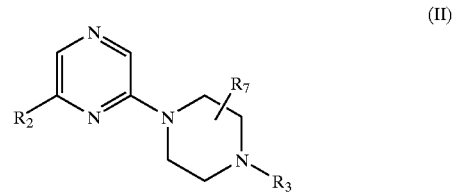

(II)

wherein
$R_2$ and $R_3$ are as defined above wherein any aryl and heteroaryl residue, alone or as part of another group, in $R_2$ in turn may be substituted in one or more positions, preferably one or two, independently of each other by $C_{1-4}$-alkyl, $C_{1-4}$-alkoxy, $C_{1-4}$-alkylthio, $C_{2-4}$-acyl, $C_{1-4}$-alkylsulphonyl, cyano, nitro, hydroxy, $C_{2-6}$-alkenyl, $C_{2-6}$-alkynyl, fluoromethyl, trifluoromethyl, trifluoromethoxy, halogen, —N($R_5$)($R_6$), aryl, aryloxy, arylthio, aryl-$C_{1-4}$-alkyl, aryl-$C_{2-4}$-alkenyl, aryl-$C_{2-4}$-alkynyl, heteroaryl, heteroaryloxy, heteroarylthio or heteroaryl-$C_{1-4}$-alkyl, aryl-$C_{1-4}$-alkoxy, aryloxy-$C_{1-4}$-alkyl, dimethylamino-$C_{2-4}$-alkoxy;
wherein any aryl or heteroaryl residue as substituents on aryl or heteroaryl, alone or as part of another group, in $R_2$ in turn may be substituted in one or more postions, preferably one, independently of each other by $C_{1-4}$-alkyl, $C_{1-4}$-alkoxy, halogen, trifluoromethyl, cyano, hydroxy or dimethylamino; $R_5$ and $R_6$ are as defined above; and
$R_7$ is hydrogen or $C_{1-4}$ alkyl.

Another aspect of the invention is a compound of any of the formulae herein wherein $R_3$ is hydrogen; or wherein $R_7$ is hydrogen, methyl, or ethyl; or wherein $R_7$ is methyl and is attached to the C2-position of the piperazine ring; or wherein $R_7$ is hydrogen.

In formula (II), $R_3$ is preferably hydrogen, and $R_7$ is preferably hydrogen or $C_{1-4}$-alkyl. When $R_7$ is $C_{1-4}$-alkyl, it is most preferably substituted in the 2-postion of the piperazine ring. $R_7$ is most preferably hydrogen or methyl.

Preferred compounds of the general formula (I) above are:
2-(Benzyloxy)-6-(1-piperazinyl)pyrazine,
2-[(2-Methoxybenzyl)oxy]-6-(1-piperazinyl)pyrazine,
2-[(3-Methoxybenzyl)oxy]-6-(1-piperazinyl)pyrazine,
2-[(3,5-Difluorobenzyl)oxy]-6-(1-piperazinyl)pyrazine,
2-(1-Naphthylmethoxy)-6-(1-piperazinyl)pyrazine,
2-(1-Phenylethoxy)-6-(1-piperazinyl)pyrazine,
2-[1-(3-Fluorophenyl)ethoxy]-6-(1-piperazinyl)pyrazine,
2-[1-(2-Methoxyphenyl)ethoxy]-6-(1-piperazinyl)pyrazine,
2-(3,4-Dihydro-2H-chromen-4-yloxy)-6-(1-piperazinyl) pyrazine,
2-(2-Phenylethoxy)-6-(1-piperazinyl)pyrazine,
2-[(2-Phenoxybenzyl)oxy]-6-(-piperazinyl)pyrazine,
2-[2-(3-Chlorophenyl)ethoxy]-6-(1-piperazinyl)pyrazine,
2-[2-(2-Methoxyphenyl)ethoxy]-6-(1-piperazinyl)pyrazine,
2-[2-(3-Methoxyphenyl)ethoxy]-6-(1-piperazinyl)pyrazine,
2-[2-(4-Methoxyphenyl)ethoxy]-6-(1-piperazinyl)pyrazine,
2-[2-(2,5-Dimethoxyphenyl)ethoxy]-6-(1-piperazinyl) pyrazine,
2-[(2-Phenylethyl)sulfanyl]-6-(1-piperazinyl)pyrazine,
2-[(5-Fluoro-2-methoxybenzyl)oxy]-6-(1-piperazinyl) pyrazine,
2-[(3-Cyanobenzyl)oxy]-6-(1-piperazinyl)pyrazine,
2-[(2-Chlorobenzyl)sulfanyl]-6-(1-piperazinyl)pyrazine,
2-[2-(4-Dimethylaminophenyl)ethoxy]-6-(1-piperazinyl) pyrazine,
2-[2-(1H-Indol-3-yl)ethoxy]-6-(1-piperazinyl)pyrazine,
2-[2-(1H-Indol-1-yl)ethoxy]-6-(1-piperazinyl)pyrazine,
4-(Benzyloxy)-2-(1-piperazinyl)pyrimidine,
4-[(2-Methoxybenzyl)oxy]-2-(1-piperazinyl)pyrimidine,
2-{[3-(Benzyloxy)benzyl]oxy}-4-(1-piperazinyl) pyrimidine,
2-Benzyl-6-(1-piperazinyl)pyrazine,
2-[(3,5-Dimethoxybenzyl)oxy]-6-(1-piperazinyl)pyrazine,
1-[6-(Benzyloxy)-2-pyrazinyl]-2-methylpiperazine,
1-[6-(Benzyloxy)-2-pyrazinyl]-2-ethylpiperazine
1-[6-(Benzyloxy)-2-pyrazinyl]-trans-2,5-dimethylpiperazine.
2-[2-(2-Fluorophenyl)ethoxy]-6-(1-piperazinyl)pyrazine,
2-(2,3-Dihydro-1H-inden-1-ylmethoxy)-6-(1-piperazinyl) pyrazine
2-(4-Phenoxybutoxy)-6-(1-piperazinyl)pyrazine.
2-[(5-Phenoxypentyl)oxy]-6-(1-piperazinyl)pyrazine.
2-[(2,5-Dimethoxybenzyl)oxy]-6-(1-piperazinyl)pyrazine.
2-{[2-(2-Phenylethyl)benzyl]oxy}-6-(1-piperazinyl) pyrazine
(2R)-1-[6-(Benzyloxy)-2-pyrazinyl]-2-methylpiperazine,
2-[2-(2,6-Difluorophenoxy)ethoxy]-6-(1-piperazinyl) pyrazine
2-[2-(2-Naphthyloxy)ethoxy]-6-(1-piperazinyl)pyrazine
2-(1-Methyl-2-phenylethoxy)-6-(1-piperazinyl)pyrazine
2-{[2-(Phenoxymethyl)benzyl]oxy}-6-(1-piperazinyl) pyrazine
2-[(5-Fluoro-2-methoxybenzyl)oxy]-6-(1-piperazinyl) pyrazine
2-[(2,5-Difluorobenzyl)oxy]-6-(1-piperazinyl)pyrazine
2-[(2-Fluorobenzyl)oxy]-6-(1-piperazinyl)pyrazine
2-(Benzo[b]thiophen-3-ylmethoxy)-6-(1-piperazinyl) pyrazine,
2-[2-(5-Methyl-2-phenyl-oxazol-4-yl)-ethoxy]-6-(1-piperazinyl)pyrazine,
2-[1-(2,6-Difluoro-phenyl)-ethoxy]-6-(1-piperazinyl) pyrazine,
2-(2-Naphthalen-2-yl-ethoxy)-6-(1-piperazinyl)pyrazine,
2-[3-(Naphthalen-2-yloxy)-propoxy]-6-(1-piperazinyl) pyrazine,
2-[2-(7-Methoxy-naphthalen-2-yloxy)-ethoxy]-6-(1-piperazinyl)pyrazine,
2-[5-(4-Chlorophenyl)-2-methylfuran-3-ylmethoxy]-6-(1-piperazinyl)pyrazine,
2-(1H-Indol-4-ylmethoxy)-6-(1-piperazinyl)pyrazine,
and their pharmacologically acceptable salts and solvates; and
2-(Benzyloxy)-6-(1-piperazinyl)pyrazine,
2-[(2-Methoxybenzyl)oxy]-6-(1-piperazinyl)pyrazine,
2-[(3-Methoxybenzyl)oxy]-6-(1-piperazinyl)pyrazine,
2-[(3,5-Difluorobenzyl)oxy]-6-(1-piperazinyl)pyrazine,
2-(1-Naphthylmethoxy)-6-(1-piperazinyl)pyrazine,
2-(1-Phenylethoxy)-6-(1-piperazinyl)pyrazine,
2-[1-(3-Fluorophenyl)ethoxy]-6-(1-piperazinyl)pyrazine,
2-[1-(2-Methoxyphenyl)ethoxy]-6-(1-piperazinyl)pyrazine,
2-(3,4-Dihydro-2H-chromen-4-yloxy)-6-(1-piperazinyl) pyrazine,
2-(2-Phenylethoxy)-6-(1-piperazinyl)pyrazine,
2-[(2-Phenoxybenzyl)oxy]-6-(1-piperazinyl)pyrazine,
2-{[3-(Benzyloxy)benzyl]oxy}-6-(1-piperazinyl)pyrazine,
2-[2-(3-Chlorophenyl)ethoxy]-6-(1-piperazinyl)pyrazine,
2-[2-(2-Methoxyphenyl)ethoxy]-6-(-piperazinyl)pyrazine,
2-[2-(3-Methoxyphenyl)ethoxy]-6-(1-piperazinyl)pyrazine,
2-[2-(4-Methoxyphenyl)ethoxy]-6-(1-piperazinyl)pyrazine,
2-[2-(2,5-Dimethoxyphenyl)ethoxy]-6-(1-piperazinyl) pyrazine,
2-[(2-Phenylethyl)sulfanyl]-6-(1-piperazinyl)pyrazine,
2-[(5-Fluoro-2-methoxybenzyl)oxy]-6-(1-piperazinyl) pyrazine,
2-[(3-Cyanobenzyl)oxy]-6-(1-piperazinyl)pyrazine,
2-[(2-Chlorobenzyl)sulfanyl]-6-(1-piperazinyl)pyrazine,
2-[2-(4-Dimethylaminophenyl)ethoxy]-6-(1-piperazinyl) pyrazine,
2-[2-(1H-Indol-3-yl)ethoxy]-6-(1-piperazinyl)pyrazine,
2-[2-(1H-Indol -1-yl)ethoxy]-6-(1-piperazinyl)pyrazine,
4-(Benzyloxy)-2-(1-piperazinyl)pyrimidine,
4-[(2-Methoxybenzyl)oxy]-2-(1-piperazinyl)pyrimidine,
2-{[3-(Benzyloxy)benzyl]oxy}-4-(1-piperazinyl) pyrimidine,
2-Benzyl-6-(1-piperazinyl)pyrazine,
2-[(3,5-Dimethoxybenzyl)oxy]-6-(1-piperazinyl)pyrazine,
1-[6-(Benzyloxy)-2-pyrazinyl]-2-methylpiperazine,
and their pharmacologically acceptable salts and solvates.

As mentioned above, the compounds of the present invention are useful for the treatment (including prophylactic treatment) of serotonin-related disorders, especially 5-HT$_{2c}$ receptor-related, in a human being or in an animal (including e.g. pets), such as eating disorders, especially obesity; memory disorders, such as Alzheimer's disease; schizophrenia; mood disorders, including, but not restricted to, major depression and bipolar depression, including both mild and manic bipolar disorder, seasonal affective disorder (SAD); anxiety disorders, including situational anxiety, generalized anxiety disorder, primary anxiety disorders (panic disorders, phobias, obsessive-compulsive disorders, and post-traumatic stress disorders), and secondary anxiety disorders (for example anxiety associated with substance abuse); pain; substance abuse; sexual dysfunctions; epilepsy; and urinary disorders, such as urinary incontinence. Additionally, the compounds of the present invention are generally useful in treatment of diseases and disorders of the central nervous system (CNS).

The compounds of the present invention in radiolabelled form, may be used as a diagnostic agent.

This invention relates to methods of making compounds of any formulae herein comprising reacting any one or more of the compounds or formulae delineated herein including any processes delineated herein.

In one aspect, the invention is a method of making a compound of formula (I) delineated herein, taking a compound of the following formula:

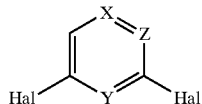

wherein; (i) X and Y represent both nitrogen and Z represents CH, forming a pyrazine derivative, or (ii) X and Z represent both CH and Y represents nitrogen, forming a pyridine derivative, or (iii) X represents C—$CF_3$, Z represents CH, and Y represents nitrogen, forming a 4-trifluoromethylpyridine derivative, or (iv) Y and Z represent both nitrogen and X represents CH, forming a pyrimidine deriviative, and wherein each Hal is independently a halogen; and reacting the compound with one or more chemical reagents in one or more steps to produce a compound of general formula (I) delineated herein.

The compounds of general formula (I) above may be prepared by, or in analogy with, conventional methods, and especially according to or in analogy with the following methods.

Method A

Compounds of formula (I) above in which $R_1$ (or $R_2$) are bound to the pyrazine-, pyridine- or pyrimidine ring in (I) via an O, S or N atom in $R_1$ (or $R_2$), are prepared by reacting a compound of the structural formula (III), (IV), (V), or (VI)

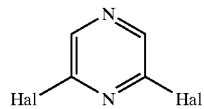
(III)

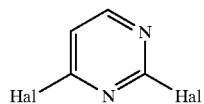
(IV)

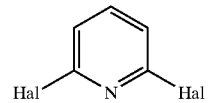
(V)

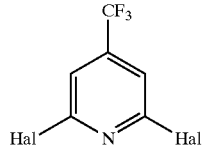
(VI)

wherein Hal is halogen, with an appropriate amine, alcohol or thiol or its corresponding anion to produce a compound of formula (VII), (VIII), (IX), or (X):

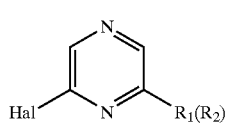
(VII)

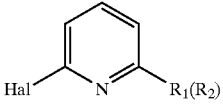
(VIII)

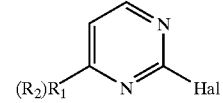
(IX)

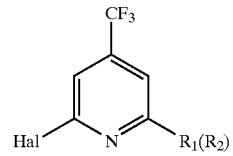
(X)

wherein $R_1$ (or $R_2$) is as defined above and with the proviso that $R_1$ (or $R_2$) is not any of the following groups

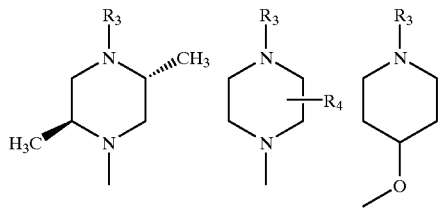

The appropriate alcohol, amine, or thiol may be converted completely or partially to its corresponding anion by treatment with bases, such as triethylamine, 1,8-diazabicyclo[5.4.0]undec-7-ene, $K_2CO_3$, NaOH, NaH, KO-t-Bu, lithium diisopropylamide or the like. The reaction is carried out in a solvent, such as dioxane, tetrahydrofuran, tert-butanol or N,N-dimethylformamide (DMF), at 0–200 °C. for 1–24 hours. The compound of formula (VII), (VIII), (IX), or (X) is reacted with 1 to 10 molar equivalents of an appropriate amine selected from

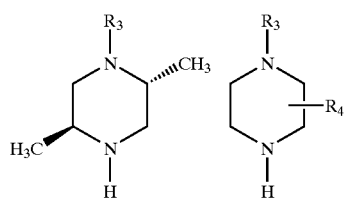

and where $R_3$ and $R_4$ are as defined above, in a solvent such as acetonitrile, dioxane, tetrahydrofuran, n-butanol, DMF, or in a mixture of solvents such as DMF/dioxane, optionally in the presence of a base, such as $K_2CO_3$, $Na_2CO_3$, $Cs_2CO_3$, NaOH, triethylamine, pyridine or the like, at 0–200° C. for 1–24 hours to produce the compound of formula (I). When $R_3$ is a nitrogen protecting group as defined above, the subsequent N-deprotection is carried out by conventional methods such as those described in Protective Groups in Organic Synthesis, John Wiley & Sons, 1991 or subsequent editions thereof.

Method B

Compounds of formula (I) are prepared by reacting a compound of formula (VII), (VIII), (IX) or (X) above with a 4-hydroxysubstituted piperidine compound of formula (XI)

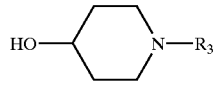
(XI)

wherein $R_3$ is as defined above.

The reaction is carried out in a solvent, such as toluene, DMF, tert-butanol or dioxane, in the presence of a base, such as 1,8-diazabicyclo[5.4.0]undec-7-ene, KOH, KO-t-Bu, NaH or the like, at 0–200° C. for 1–24 hours.

The nitrogen atom in (XI) may be protected with a suitable protecting group, preferably tert-butoxycarbonyl, trityl or benzyl. N-Deprotection is then carried out by conventional methods such as those described in Protective Groups in Organic Synthesis, John Wiley & Sons, 1991 or subsequent editions thereof.

Method C

Compounds of formula (I) are prepared by reacting a compound of formula (III), (IV), (V), or (VI) above with an appropriate amine, selected from

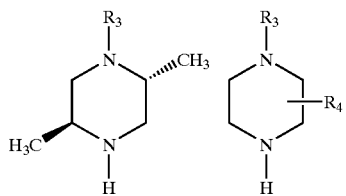

or a 4-hydroxysubstituted piperidine compound (XI)

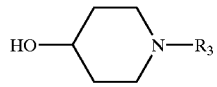
(XI)

and where $R_3$ and $R_4$ are as defined above to produce a compound of formula (XII) or (XIII):

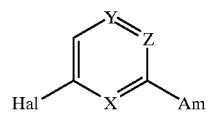
(XII)

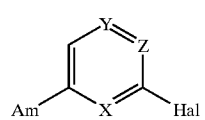
(XIII)

wherein Hal is as defined above, and X, Y, Z have the same meaning as in formula (I), and Am is an amine residue selected from

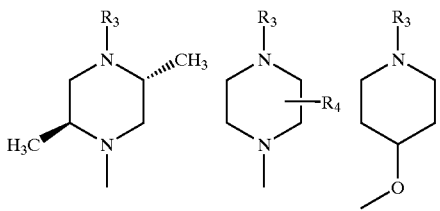

and where $R_3$ and $R_4$ are as defined above. The reaction conditions may be those described for methods A and B above. The compound of formula (XII) or (XIII) is reacted with an appropriate alcohol, amine (other than those defined for Am above) or thiol or its corresponding anions to produce a compound of the formula (I). The reaction conditions may be those described for method A above. When $R_3$ is a nitrogen protecting group as defined above, the subsequent N-deprotection is carried out by conventional methods such as those described in Protective Groups in Organic Synthesis, John Wiley & Sons, 1991 or subsequent editions thereof.

Method D

According to another general process (the Suzuki reaction; for a review, see: Chem. Rev. 1995, 95, 2457–2483), the compounds of formula (I) wherein $R_1$ or $R_2$ are aryl or heteroaryl may be prepared by reacting a compound of formula (III), (IV), (V), or (VI) with a boronic acid derivative of the type heteroaryl-B(OH)$_2$ or aryl-B(OH)$_2$, where heteroaryl and aryl are as defined above, in the presence of a transition metal catalyst such as (Ph$_3$P)$_4$Pd, where Ph represents phenyl, in a suitable solvent such as an ether (e.g., 1–2-dimethoxyethane or tetrahydrofuran), in the presence or absence of water, or an aromatic hydrocarbon (e.g., toluene). The reaction is preferably carried out in the presence of a base such as an alkali or alkaline earth metal carbonate (e.g., sodium carbonate) at a suitable temperature up to reflux to provide a compound of formula (XIV) or (XV)

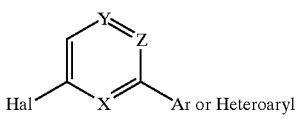
(XIV)

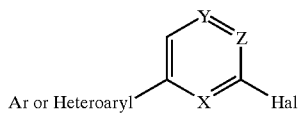
(XV)

The compound of formula (XIV) or (XV) is reacted with 1 to 10 molar equivalents of an appropriate amine selected from

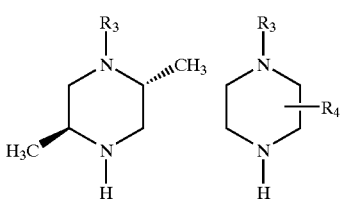

or a 4-hydroxysubstituted piperidine compound (XI)

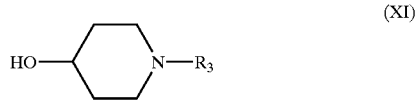

to produce a compound of formula (I) and where $R_3$ and $R_4$ are as defined above. The reaction conditions may be those described for methods A and B above.

Method E

A compound of formula (XII) or (XIII) is reacted with a boronic acid derivative heteroaryl-B(OH)$_2$ or aryl-B(OH)$_2$ to provide a compound of formula (I). Heteroaryl and aryl are as defined above. The reaction conditions may be those described in method D.

An obtained compound of formula (I) may be converted to another compound of formula (I) by methods well known in the art.

The processes described above may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are maleic acid, fumaric acid, succinic acid, methanesulfonic acid, acetic acid, oxalic acid, benzoic acid, hydrochloric acid, sulphuric acid, phosphoric acid, and the like.

The compounds of formula (I) may possess one or more chiral carbon atoms, and they may therefore be obtained in the form of optical isomers, e.g. as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The necessary starting materials for preparing the compounds of formula (I) are either known or may be prepared in analogy with the preparation of known compounds.

In accordance with the present invention, the compounds of formula (I), in the form of free bases or salts with physiologically acceptable acids, can be brought into suitable galenic forms, such as compositions for oral use, for injection, for nasal spray administration or the like, in accordance with accepted pharmaceutical procedures. Such pharmaceutical compositions according to the invention comprise an effective amount of the compounds of formula (I) in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavouring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

As mentioned above, the compounds of the invention may be used for the treatment of serotonin-related disorders in a human being or an animal, such as eating disorders, particularly obesity, memory disorders, schizophrenia, mood disorders, anxiety disorders, pain, substance abuse, sexual dysfunctions, epilepsy, and urinary disorders. The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will now be illustrated with the following examples, which however, are for illustrative purposes are not intended to limit the scope of the invention.

EXAMPLES

General

The structures of the prepared compounds were confirmed by standard spectroscopical methods, and elemental analysis and/or high resolution MS. The NMR data were obtained on a JEOL JNM-EX 270, a Bruker 400 DPX or a Bruker DRX 500 spectrometer. IR spectra were obtained on a Perkin Elmer SPECTRUM 1000 FT-IR spectrometer. High resolution MS was obtained on a Micromass LCT spectrometer. Elemental analysis was performed by Mikro Kemi AB, Uppsala, Sweden or at Pharmacia AB, Stockholm, Sweden. Melting points, when given, were obtained on a Büchi or a Gallenkamp melting point apparatus and are uncorrected.

Example 1

2-(1-Naphthylmethoxy)-6-(1-piperazinyl)Pyrazine

To a solution of 2,6-dichloropyrazine (298 mg, 2.00 mmol) and 1-naphthylmethanol (348 mg, 2.20 mmol) in dioxane (5 mL) was added NaH (55% in mineral oil, 96 mg, 2.2 mmol) at room temperature. The reaction was stirred at room temperature and monitored by GC. After 3 h, piperazine (189 mg, 2.20 mmol) and NaH (55% in oil, 96 mg, 2.2 mmol) was added into the reaction flask at room temperature. The reaction mixture was stirred at room temperature for 24 h. The solvent was evaporated off. To the residue was added piperazine (671 mg, 7.80 mmol) and acetonitrile (5 mL) and the solution was heated under reflux for 5 h. The reaction mixture was directly loaded on a short column of silica gel for flash column chromatography. Elution with MeOH/dichloromethane (1:9) furnished 0.41 g (64%) of the title compound. HRMS m/z calcd for $C_{19}H_{20}N_4O$ (M)$^+$ 321.1715, found 321.1721. Anal. ($C_{19}H_{20}N_4O.0.1\ H_2O$) C, H, N.

Example 2

2-[1-(3-Fluorophenyl)ethoxy]-6-(1-piperazinyl) pyrazine

Step 1: 2-Chloro-6-[1-(3-fluorophenyl)ethoxy] pyrazine

To a solution of 2,6-dichloropyrazine (298 mg, 2.00 mmol) and 1-(3-fluorophenyl)ethanol (308 mg, 2.2 mmol) in dioxane (5 mL) was added NaH (55% in oil, 96 mg, 2.2 mmol) at room temperature. The reaction mixture was stirred over night. Water (0.5 mL) was added and the mixture was stirred for 15 min. Drying ($K_2CO_3$), filtration, and concentration in vacuo gave the title compound as an oil (0.55 g) that was used directly in the next step. MS m/z 254 (M+H)$^+$.

Step 2: 2-[1-(3-Fluorophenyl)ethoxy]-6-(1-piperazinyl)pyrazine

A mixture of the product from step 1 above (crude, 1.09 g,~4.3 mmol), piperazine (1.03 g, 12.0 mmol) and $K_2CO_3$ (1.00 g, 7.2 mmol) in acetonitrile (5 mL) was heated under reflux overnight (20 h). After cooling, ethyl acetate (15 mL) and water (5 mL) were added. The ethyl acetate layer was filtered through a short column of silica gel using MeOH/ ethyl ether (1:1) as eluent to give 0.72 g (55%) of the title compound as an oil. HRMS m/z calcd for $C_{16}H_{19}N_4O_4F$ (M)$^+$ 302.1543, found 302.1528. Anal. ($C_{16}H_{19}N_4OF$ .$0.5H_2O$) C, H, N.

Example 3

2-(1,3-Benzodioxol-5-ylmethoxy)-6-(1-piperazinyl) pyrazine, Acetate

Step 1: 2-(1,3-Benzodioxol-5-ylmethoxy)-6-chloropyrazine

To a solution of 2,6-dichloropyrazine (298 mg, 2.00 mmol) and piperonyl alcohol (335 mg, 2.20 mmol) in dioxane (5 mL) was added NaH (55% in mineral oil, 96 mg, 2.2 mmol) at room temperature. The reaction mixture was stirred overnight. Water (0.5 mL) was added and the mixture was stirred for 15 min. Drying, $Na_2CO_3$, filtration and concentration in vacuo furnished an oil (0.54 g) that was used directly in the next step. HRMS m/z calcd for $C_{12}H_9ClN_2O_3$ (M)$^+$ 264.0302, found 264.0303.

Step 2: 2-(1,3-Benzodioxol-5-ylmethoxy)-6-(1-piperazinyl)pyrazine, Acetate

A mixture of the product from step 1 above (0.54 g, 2.0 mmol), piperazine (0.86 g, 10 mmol) and $K_2CO_3$ (1.00 g, 7.2 mmol) in acetonitrile (5 mL) was heated under reflux for 5 h. After cooling, ethyl acetate (20 mL) and water (5 mL) were added. The saved ethyl acetate layer was filtered through a short column of silica gel using methanol/ethyl ether (1:1) as eluent. This furnished the free base of the title compound as an oil (0.43 g). This material was dissolved in methanol and acetic acid (0.5 mL) was added. The solution was concentrated. Diethyl ether (25 mL) was added and the flask was shaken until crystallization started. The crystals was collected, washed with diethyl ether and dried in air to give 0.34 g (45%) of the title compound: mp 124–127° C. HRMS m/z calcd for $C_{16}H_{18}N_4O_3$ (M)$^+$ 314.1379, found 314.1308. Anal. ($C_{16}H_{18}N_4O_3.CH_3COOH.1.6H_2O$) C, H, N.

Example 4

2-[(3-Methoxybenzyl)oxy]-6-(1-piperazinyl) pyrazine, Acetate

Step 1: 2-Chloro-6-[(3-methoxybenzyl)oxy]pyrazine

To a solution of 2,6-dichloropyrazine (444 mg, 3.00 mmol) and 3-methoxybenzyl alcohol (455 mg, 3.30 mmol) in dioxane (5 mL) was added NaH (55% in oil, 144 mg, 3.30 mmol) at room temperature. The reaction mixture was stirred overnight. Water (0.5 mL) and ethyl acetate (10 mL) were added and the mixture was stirred for 15 min and then filtered. The filtrate was dried over $K_2CO_3$ and concentrated to give an oil (0.86 g) that was used directly in the next step. MS m/z 250 (M+H)$^+$.

Step 2: 2-[(3-Methoxybenzyl)oxy]-6-(1-piperazinyl) pyrazine, Acetate

A mixture of the product from step 1 above (0.57 g, ~2.0 mmol), piperazine (0.86 g, 10 mmol) and $K_2CO_3$ (1.00 g, 7.2 mmol) in acetonitrile (5 mL) was heated under reflux for 10 h. After cooling, ethyl acetate (30 mL) was added. The ethyl acetate layer was washed with water and brine, dried over $Na_2CO_3$, and concentrated under reduced pressure. The residue was dissolved in diethyl ether. Acetic acid (0.5 mL) was added and the solution was left at room temperature for crystallization. The crystals were collected, washed with diethyl ether and dried in vaccum to give 0.54 g (75%) of the title compound: mp 111–113° C. HRMS m/z calcd for $C_{16}H_{20}N_4O_2$ (M)$^+$ 300.1586, found 300.1589. Anal. ($C_{16}H_{20}N_4O_2.CH_3COOH$) C, H, N.

Example 5

2-[(2-Methoxybenzyl)oxy]-6-(1-piperazinyl) pyrazine, Dihydrochloride

Step 1: 2-Chloro-6-[(2-methoxybenzyl)oxy]pyrazine

The title compound was prepared according to the procedure of example 4, step 1 starting from 2,6-dichloropyrazine (298 mg, 2.00 mmol), 2-methoxybenzyl alcohol (303 mg, 2.20 mmol) and NaH (55% in mineral oil, 96 mg, 2.2 mmol). The yield of the crude product was 0.49 g (98%) and was used directly as such in the next step. MS m/z 250 (M)$^+$. HRMS m/z calcd for $C_{12}H_{11}ClN_2O_2$ (M)$^+$ 250.0509, found 250.0522.

Step 2: 2-[(2-Methoxybenzyl)oxy]-6-(1-piperazinyl) pyrazine, Dihydrochloride The title compound was prepared according to the procedure of example 4, step 2 starting from the product of step 1 above (0.49 g), piperazine (0.86 g, 10 mmol) and $K_2CO_3$ (1.00 g, 7.2 mmol). This gave the free base of the title compound as an oil. Yield 0.43 g (73%). The free base was dissolved in ethyl ether and a solution of HCl in diethyl ether was added until no more precipitate was formed. The precipitate was collected, washed with diethyl ether, and dried in vaccum to give 0.41 g (56%) of the title compound: mp 171–173° C.). HRMS m/z calcd for $C_{16}H_{20}N_4O_2$ (M)$^+$ 300.1586, found 300.1586. Anal. ($C_{16}H_{20}N_4O_2.2HCl$) C, H, N.

Example 6

2-[(3,5-Difluorobenzyl)oxy]-6-(1-piperazinyl) pyrazine, Acetate

Step 1: 2-Chloro-6-[(3,5-difluorobenzyl)oxy] pyrazine

The title compound was prepared according to the procedure of example 4, step 1 starting from 2,6- dichloropyrazine (444 mg, 3.00 mmol), 3,5-difluorobenzyl alcohol (475 mg, 3.30 mmol) and NaH (55% in mineral oil, 144 mg, 3.30 mmol). The solid product was collected, washed with water, and dried to give 0.77 g (100%) of the crude product that was used directly in the next step. An analytical sample was recrystallized from diethyl ether/hexane: mp 70–71° C. MS m/z 257 (M+H)$^+$. Anal. ($C_{11}H_7ClFN_2O$) C, H, N.

Step 2: 2-[(3,5-Difluorobenzyl)oxy]-6-(1-piperazinyl)pyrazine, Acetate

The title compound was prepared according to the procedure of example 4, step 2 starting from the product of step 1 above (0.51 g, ~2.0 mmol), piperazine (0.86 g, 10 mmol) and $K_2CO_3$ (1.00 g, 7.2 mmol). Yield 0.49 g, (67%); mp 70–72° C.; HRMS m/z calcd for $C_{15}H_{16}F_2N_4O$ (M)$^+$ 306.1292, found 306.1292. Anal. ($C_{15}H_{16}F_2N_4O\cdot CH_3COOH\cdot H_2O$) C, H, N.

Example 7

2-([1,1'-Biphenyl]-4-ylmethoxy)-6-(1-piperazinyl)pyrazine, Acetate

Step 1: 2-([1,1'-Biphenyl]-4-ylmethoxy)-6-chloropyrazine

The title compound was prepared according to the procedure of example 4, step 1 starting from 2,6-dichloropyrazine (444 mg, 3.00 mmol), p-phenylbenzyl alcohol (607 mg, 3.30 mmol) and NaH (55% in mineral oil, 144 mg, 3.30 mmol). Recrystallization from hexane gave 0.55 g (88%) of the title compound: mp 86–87° C. MS m/z: 297 (M+H)$^+$. Anal. ($C_{17}H_{13}ClN_2O$) C, H, N.

Step 2: 2-([1,1'-Biphenyl]-4-ylmethoxy)-6-(1-piperazinyl)pyrazine, Acetate

The title compound was prepared according to the procedure of example 4, step 2 starting from the product of step 1 above (0.54 g, 1.87 mmol), piperazine (0.86 g, 10.0 mmol) and $K_2CO_3$ (1.00 g, 7.2 mmol). Yield: 0.35 g (44%); mp 102–104° C. HRMS m/z calcd for $C_{21}H_{22}N_4O$ (M)$^+$ 346.1794, found 346.1777. Anal. ($C_{21}H_{22}N_4O\cdot CH_3COOH\cdot 0.55H_2O$) C, H, N.

Example 8

2-[2-(3-Chlorophenyl)ethoxy]-6-(1-piperazinyl)pyrazine, Acetate

Step 1: 2-Chloro-6-[2-(3-chlorophenyl)ethoxy]pyrazine

The title compound was prepared according to the procedure of example 4, step 1 starting from 2,6-dichloropyrazine (444 mg, 3.00 mmol) and m-chlorophenethyl alcohol (515 mg, 3.30 mmol) and NaH (55% in mineral oil, 144 mg, 3.30 mmol). The crude product (0.92 g) was used directly in the next step. MS m/z 269 (M+H)$^+$.

Step 2: 2-[2-(3-Chlorophenyl)ethoxy]-6-(1-piperazinyl)pyrazine, Acetate

The title compound was prepared according to the procedure of example 4, step 2 starting from the product of step 1 above (0.81 g, 3.02 mmol), piperazine (0.86 g, 10 mmol) and $K_2CO_3$ (1.00 g, 7.2 mmol). Yield: 0.75 g (65%); mp 118–119° C. HRMS m/z calcd for $C_{16}H_{19}ClN_4O$ (M)$^+$ 318.1247, found 318.1249. Anal. ($C_{16}H_{19}ClN_4O\cdot CH_3COOH$) C, H, N.

Example 9

6-(1-Piperazinyl)-2-pyrazinyl 1,2,3,4-tetrahydro-1-naphthalenyl ether, Acetate

Step 1: 2-Chloro-6-(1,2,3,4-tetrahydro-1-naphthalenyloxy)pyrazine

The title compound was prepared according to the procedure of example 4, step 1 starting from 2,6-dichloropyrazine (444 mg, 3.00 mmol) and 1,2,3,4-tetrahydro-1-naphthol (488 mg, 3.30 mmol) and NaH (55% in oil, 144 mg, 3.30 mmol). The crude product (0.86 g) was used directly in the next step. MS m/z 261 (M+H)$^+$.

Step 2: 6-(1-Piperazinyl)-2-pyrazinyl 1,2,3,4-tetrahydro-1-naphthalenyl ether, Acetate The title compound was prepared according to the procedure of example 4, step 2 starting from the product of step 1 above (0.75 g, 2.88 mmol), piperazine (0.86 g, 10 mmol) and $K_2CO_3$ (1.00 g, 7.2 mmol). Yield: 0.59 g (55%); mp 160–162° C. MS m/z 310 (M)$^+$. HRMS m/z calcd for $C_{18}H_{22}N_4O$ (M)$^+$ 310.1794, found 310.1799. Anal. ($C_{18}H_{22}N_4O\cdot CH_3COOH$) C, H, N.

Example 10

2-(1-Piperazinyl)-6-{[4-(trifluoromethyl)benzyl]oxy}pyrazine, Acetate

Step 1: 2-Chloro-6-{[4-(trifluoromethyl)benzyl]oxy}pyrazine

The title compound was prepared according to the procedure of example 4, step 1 starting from 2,6-dichloropyrazine (444 mg, 3.00 mmol) and 4-trifluoromethylbenzyl alcohol (581 mg, 3.30 mmol) and NaH (55% in mineral oil, 144 mg, 3.30 mmol). Recrystallization from hexane gave 0.81 g (93%) of the title compound: mp 67–69° C. MS m/z 289 (M+H)$^+$. Anal. ($C_{12}H_8ClF_3N_2O$) C, H, N.

Step 2: 2-(1-Piperazinyl)-6-{[4-(trifluoromethyl)benzyl]oxy}pyrazine, Acetate

The title compound was prepared according to the procedure of example 4, step 2 starting from the product of step 1 above (0.54 g, 1.89 mmol), piperazine (0.86 g, 10 mmol) and $K_2CO_3$ (1.00 g, 7.20 mmol). Yield: 0.36 g (48%); mp 84–85° C. MS m/z 338 (M)$^+$. HRMS m/z calcd for $C_{16}H_{17}F_3N_4O$ (M)$^+$ 338.1054, found 338.1063. Anal. ($C_{16}H_{17}ClF_3N_4O\cdot CH_3COOH$) C, H, N.

Example 11

2-(1-Piperazinyl)-6-(3-pyridinylmethoxy)pyrazine, Acetate

Step 1: 2-Chloro-6-(3-pyridinylmethoxy)pyrazine

The title compound was prepared according to the procedure of example 4, step 1 starting from 2,6-dichloropyrazine (444 mg, 3.00 mmol), nicotinic alcohol (360 mg, 3.30 mmol) in dioxane (5 mL) and NaH (55% in oil, 144 mg, 3.30 mmol). The crude product, obtained as an oil (0.72 g), was used directly in the next step. MS m/z 221 (M)$^+$.

Step 2: 2-(1-Piperazinyl)-6-(3-pyridinylmethoxy) pyrazine, Acetate

The title compound was prepared according to the procedure of example 4, step 2 starting from the product of step 1 above (0.74 g, 3.35 mmol), piperazine (0.86 g, 10 mmol) and $K_2CO_3$ (1.00 g, 7.2 mmol). Yield: 0.73 g (44%); mp 98–99° C.; MS m/z 271(M)$^+$. HRMS m/z calcd for $C_{14}H_{17}N_5O$ (M)$^+$ 271.1433, found 271.1425. Anal. ($C_{14}H_{17}N_5O \cdot CH_3COOH$) C, H, N.

Example 12

2-(1-Piperazinyl)-6-[2-(3-pyridinyl)ethoxy]pyrazine, Acetate

Step 1: 2-Chloro-6-[2-(3-pyridinyl)ethoxy]pyrazine

The title compound was prepared according to the procedure of example 4, step 1 starting from 2,6-dichloropyrazine (444 mg, 3.00 mmol) and 2-(3-pyridyl)ethanol (405 mg, 3.30 mmol) and NaH (55% in mineral oil, 144 mg, 3.30 mmol). The crude product, obtained as an oil (0.62 g, 88% yield), was used directly in the next step. MS m/z 235 (M)$^+$.

Step 2: 2-(1-Piperazinyl)-6-[2-(3-pyridinyl)ethoxy] pyrazine, Acetate

The title compound was prepared according to the procedure of example 4, step 2 starting from the product of step 1 above (0.62 g, 2.64 mmol), piperazine (0.86 g, 10 mmol) and $K_2CO_3$ (1.00 g, 7.2 mmol). Yield: 0.40 g (44%); mp 90–91° C. MS m/z 285 (M)$^+$. HRMS m/z calcd for $C_{15}H_{19}N_5O$ (M)$^+$ 285.1590, found 285.1598. Anal. ($C_{15}H_{19}N_5O \cdot CH_3COOH$) C, H, N.

Example 13

2-(2-Furylmethoxy)-6-(1-piperazinyl)pyrazine

Step 1: tert-Butyl 4-(6-chloro-2-pyrazinyl)-1-piperazinecarboxylate

A mixture of tert-butyl 1-piperazinecarboxylate (5.07 g, 27.2 mmol), 2,6-dichloropyrazine (3.38 g, 22.7 mmol), and $K_2CO_3$ (4.09 g, 30.0 mmol) in acetonitrile (20 mL) was stirred at 65° C. for 12.5 h and for a further 15 h at room temperature. Ether was added and the suspension was filtered. Concentration in vacuo furnished the crude product as an oil that crystallized upon standing. Purification by chromatography on silica gel using ethyl acetate/n-hexane (6:4) as eluent gave 6.1 g (90%) of the title compound as a solid. HRMS m/z calcd for $C_{13}H_{19}ClN_4O_2$ (M)$^+$ 298.1197, found 298.1211. Anal. ($C_{13}H_{19}ClN_4O_2$) C, H, N.

Step 2: 6-Chloro-2-(1-piperazinyl)pyrazine*

A solution of trifluoroacetic acid (TFA; 6 mL) in dichloromethane (24 mL) was added to a stirred solution of the product of step 1 above (5.79 g, 19.4 mmol) in dichloromethane (20 mL) at 0° C. After 1 h and 1.5 h of stirring, additional portions (10 mL and 5 mL) of TFA were added. Crushed ice and 5 M aqueous NaOH were added and the mixture was extracted with dichloromethnae (12×200 mL). The combined organic layers were dried ($K_2CO_3$), filtered and concentrated in vacuo. This furnished 3.48 g (90%) of the title compound as a light yellow solid.

*Previously described in a) J. Med. Chem. 1978, 21, 536–542; b) U.S. Pat. No. 4,082,844

Step 3: 2-(2-Furylmethoxy)-6-(1-piperazinyl) pyrazine

K-t-BuO (1.55 g, 13.8 mmol) was added to a mixture of the product from step 2 above (1.40 g, 7.05 mmol) and 2-furanmethanol (5.3 g, 54 mmol). After being stirred for 7.5 h at 110° C., the mixture was applied onto a bed of silica (16×6 cm). Elution with $CHCl_3$/MeOH (95:5 followed by 90:10) furnished 1.35 g (74%) of the title compound as an oil. HRMS m/z calcd for $C_{13}H_{16}N_4O_2$(M)$^+$ 260.1273, found 260.1276. Anal. ($C_{13}H_{16}N_4O_2$) C, H, N.

Example 14

2-(2-Phenylethoxy)-6-(1-piperazinyl)pyrazine, Maleate

K-t-BuO (0.80 g, 7.13 mmol) was added to a mixture of the product from example 13, step 2 (0.638 g, 3.21 mmol) and 2-phenylethanol (5.62 g, 46.0 mmol). After being stirred for 5 h at 105° C. in a sealed flask, the mixture was applied onto a bed of silica (16×5 cm). Elution with $CHCl_3$/MeOH (97:3 followed by 90:10) furnished 0.68 g of an thick beige colored oil. This material was redissolved in ethyl acetate and $K_2CO_3$ was added. Filtration and concentration in vacuo furnished 0.67 g (74%) of the free base of the title compound as an oil. HRMS m/z calcd for $C_{16}H_{20}N_4O$ (M)$^+$ 284.1637, found 284.1630. The free base was converted into its maleate salt which was recrystallized from MeOH/ether: mp 166–168° C. Anal. ($C_{16}H_{20}N_4O \cdot C_4H_4O_4$) C, H, N.

Example 15

2-(2-Furyl)-6-(1-piperazinyl)pyrazine

Step 1: 2-Chloro-6-(2-furyl)pyrazine 1,2-Dimethoxyethane (130 mL) was added to a mixture of tetrakis(triphenylphosphine)palladium (0) (0.93 g, 0.80 mmol) and 2,6-dichloropyrazine (2.55 g, 17.1 mmol). After 5 min of stirring at room temperature, furan-2-boronic acid (1.91 g, 17.1 mmol) followed by aqueous $Na_2CO_3$ (30 mL; 2 M) were added. The mixture was heated at reflux for 1 h [TLC monitoring by $SiO_2$/n-hexane/ethyl acetate (90:10)]. The layers were separated and the light brownish water layer was extracted with dichloromethane (2×200 mL). The combined organic layers were dried ($K_2CO_3$), filtered and concentrated in vacuo. The brown-yellow oil obtained was purified by silica gel chromatography (18.5×4 cm) eluting with n-hexane/ethyl acetate (90:10). This furnished 1.47 g (48%) of the title compound as a light yellow solid. HRMS m/z calcd for $C_8H_5ClN_2O$ (M)$^+$ 180.0090, found 180.0092. Anal. ($C_8H_5ClN_2O$) C, H, N.

Step 2: 2-(2-Furyl)-6-(1-piperazinyl)pyrazine

A mixture of the product from step 1 above (0.94 g, 5.2 mmol), piperazine (1.28 g, 14.9 mmol, $K_2CO_3$ (0.87 g, 6.3 mmol) in acetonitrile (5 mL) was heated in a sealed pyrex flask at 85° C. for 3 h. The mixture was diluted with dichloromethane, filtered, and concentrated in vacuo. The oily residue was purified by silica gel chromatography (18×4 cm) to furnish a yellow oil. This material was redissolved in a small volume of $CHCl_3$/ether (9:1) and filtered through a short (4 cm) plug of alumina eluting with ether/MeOH (96:4). The filtrate was concentrated in vacuo to afford 0.77 g (64%) of the title compound as a light yellow solid. HRMS m/z calcd for $C_{12}H_{14}N_4O$ (M)$^+$ 230.1168, found 230.1170. Anal. ($C_{12}H_{14}N_4O$) C, H, N.

Example 16

2-(1-Piperazinyl)-6-(3-thienyl)pyrazine

Step 1: 2-Chloro-6-(3-thienyl)pyrazine 1,2-Dimethoxyethane (120 mL) was added to a mixture of tetrakis(triphenylphosphine)palladium (0) (0.87 g, 0.75 mmol) and 2,6-dichloropyrazine (2.43 g, 16.3 mmol). After 15 min of stirring at room temperature, thiophene-3-boronic acid (2.09 g, 16.3 mmol) followed by aqueous $Na_2CO_3$ (2 M; 25 mL) were added. The mixture was heated at reflux for 2 h [TLC monitoring by $SiO_2$/n-hexane/ethyl acetate (85:15)]. The layers were separated and the light brownish water layer was extracted with ether (2×100 mL). The combined organic layers were dried ($K_2CO_3$), filtered and concentrated in vacuo. The brownish oil obtained was purified by silica gel chromatography (18×5 cm) eluting with n-hexane/ethyl acetate (85:15). This furnished 1.46 g (45%) of the title compound as an off-white solid. HRMS m/z calcd for $C_8H_5ClN_2S$ (M)$^+$ 195.9862, found 195.9868. Anal. ($C_8H_5ClN_2S$) C, H, N.

Step 2: 2-(1-Piperazinyl)-6-(3-thienyl)pyrazine

A mixture of the product from step 1 above (1.04 g, 5.29 mmol), piperazine (1.32 g, 15.3 mmol), and $K_2CO_3$ (0.81 g, 5.82 mmol) in acetonitrile (6 mL) was heated in a sealed pyrex flask at 85° C. for 8.5 h. The reaction mixture was diluted with dichloromethane, filtered, and concentrated in vacuo. The semi-solid residue was purified by column chromatography on silica gel (18×5 cm) using $CHCl_3$/MeOH (9:1) as eluent to furnish an oil. This material was redissolved in ethyl acetate, filtered, and concentrated in vacuo. This gave 0.98 g (75%) of the title compound as a yellow sticky oil. HRMS m/z calcd for $C_{12}H_{14}N_4S$ (M)$^+$ 246.0939, found 246.0943. Anal. ($C_{12}H_{14}N_4S$) C, H, N.

Example 17

N-Benzyl-6-(1-piperazinyl)-2-pyrazinamine

Step 1: N-Benzyl-6-chloro-2-pyrazinamine

A mixture of 2,6-dichloropyrazine (1.31 g, 8.8 mmol), benzylamine (1.15 g, 10.7 mmol) and $K_2CO_3$ (1.65 g, 11.9 mmol) in acetonitrile (6 mL) was heated at 85° C. for 13 h in a sealed pyrex flask. The reaction mixture was diluted with dichloromethane, filtered and concentrated in vacuo. The yellow solid residue was dissolved in a small volume of methanol and purified by silica gel chromatography (18×4 cm) using $CHCl_3$/MeOH (98:2) as eluent. A second purification ($SiO_2$;16×4 cm) using $CHCl_3$ as eluent furnished 1.55 g (81%) of the title compound as a light yellow solid. HRMS m/z calcd for $C_{11}H_{10}ClN_3$ (M)$^+$ 219.0563, found 219.0568. Anal. ($C_{11}H_{10}ClN_3$) C, H, N.

Step 2: N-Benzyl-6-(1-piperazinyl)-2-pyrazinamine

A mixture of the product from step 1 above (1.25 g, 5.7 mmol), piperazine (1.0 g, 11.6 mmol), and $K_2CO_3$ (1.0 g, 7.3 mmol) in dioxane (3 mL) was heated at 160° C. for 11 h in a sealed pyrex flask. The reaction mixture was diluted with dichloromethane, filtered and concentrated in vacuo. The red-brownish residue was dissolved in a small volume of $CHCl_3$/MeOH (9:1) and purified by silica gel chromatography (15×4 cm) using $CHCl_3$/MeOH (95:5, followed by 9:1) as eluent. The free base was obtained as a brownish solid (0.9 g, 3.33 mol) that was redissolved in methanol (10 mL). Maleic acid (0.45 g, 3.83 mmol) in methanol (5 mL) was added and the salt was precipitated out by addition of ether. The salt was recrystallized from MeOH-ether and finally converted back to the free base by alkalinization (10% aqueous $Na_2CO_3$) and extraction with ether (5×60 mL). The combined ether layers were dried ($K_2CO_3$), filtered and concentrated. This furnished 0.36 g (23%) of the title compound as a light yellow powder. HRMS m/z calcd for $C_{15}H_{19}N_5$ (M)$^+$ 269.1640, found 269.1641. Anal. ($C_{15}H_{19}N_5$) C, H, N.

Example 18

1-[6-(2-Thienylmethoxy)-2-pyridinyl]piperazine

Step 1: 2-Chloro-6-(2-thienylmethoxy)pyridine*

K-t-BuO (1.70 g, 15.1 mmol) was added portionwise to a stirred mixture of 2-thiophenemethanol (2.14 g, 18.7 mmol) and 2,6-dichloropyridine (2.13 g, 14.4 mmol) in dioxane (3 mL) at room temperature. An exothermic reaction started and more dioxane (3 mL) was added. After 3 h of stirring at room temperature, the reaction mixture was passed through a column of silica using n-hexane/ethyl acetate (85:15) as eluent. A second purification on silica (16×4 cm) using n-hexane/ethyl acetate (9:1) furnished 3.0 g (93%) of the title compound as a light beige oil. HRMS m/z calcd for $C_{10}H_8ClNOS$ (M)$^+$ 225.0015, found 225.0022. Anal. ($C_{10}H_8ClNOS$) C, H, N.

*Previously described in EP 693490.

Step 2: 1-[6-(2-Thienylmethoxy)-2-pyridinyl] piperazine

A mixture of the product from step 1 above (1.35 g, 5.98 mmol), piperazine (1.55 g, 17.9 mmol) and $K_2CO_3$ (0.91 g, 6.58 mmol) in acetonitrile (5 mL) was heated at 125 125° C. for 6.5 h in a sealed pyrex flask. The reaction mixture was diluted with dichlorometane, filtered and concentrated in vacuo. The semi-solid residue was purified by silica gel (16×4 cm) chromatography using $CHCl_3$/MeOH (9:1) as eluent. Solvents were evaporated and the oily residue was redissolved in $CHCl_3$/ether (1:1). Filtration and concentration in vacuo furnished 0.78 g (47%) of the title compound as a beige oil. HRMS m/z calcd for $C_{14}H_{17}N_3OS$ (M)$^+$ 275.1092, found 275.1101. Anal. ($C_{14}H_{17}N_3OS$) C, H, N.

Example 19

2-(2-Phenoxyethoxy)-6-(1-piperazinyl)pyrazine

Step 1: 2-Chloro-6-(2-phenoxyethoxy)pyrazine

K-t-BuO (1.61 g, 14.3 mmol) was added portionwise to a stirred mixture of 2,6-dichloropyrazine (2.03 g, 13.6 mmol) and 2-phenoxyethanol (2.54 g, 18.4 mmol) in dioxane (8 mL) at 0° C. (ice-bath). After 5 min of stirring, the ice-bath was removed and the mixture was stirred at room temperature for 1 h. The reaction mixture was diluted with ether, filtered and concentrated in vacuo. The oily residue was purified by silica gel chromatography (18×5 cm) using n-hexane/ethyl acetate (92:8) as eluent. This furnished 2.92 g (86%) of the title compound as a white solid. HRMS m/z calcd for $C_{12}H_{11}ClN_2O_2$ (M)$^+$ 250.0509, found 250.0511. Anal. ($C_{12}H_{11}ClN_2O_2$) C, H, N.

Step 2: 2-(2-Phenoxyethoxy)-6-(1-piperazinyl) pyrazine

A mixture of the product from step 1 above (1.29 g, 5.15 mmol), piperazine (1.30 g, 15.1 mmol) and $K_2CO_3$ (0.71 g, 5.14 mmol) in acetonitrile (5 mL) was heated in a sealed pyrex flask at 100° C. for 4 h. The reaction mixture was diluted with dichloromethane, filtered, and concentrated in vacuo. The light-brown semi-solid residue was purified by silica gel chromatography (15×4 cm) using $CHCl_3$/MeOH (9:1) as eluent. Solvents were evaporated off and the residue was redissolved in ether/$CHCl_3$ (1:1). Filtration and concentration in vacuo furnished 1.05 g (68%) of the title compound as a white solid. HRMS m/z calcd for $C_{16}H_{20}N_4O_2$ (M)$^+$ 300.1586, found 300.1578. Anal. ($C_{16}H_{20}N_4O_2$) C, H, N.

Example 20

2-(Benzyloxy)-6-(1-piperazinyl)pyrazine*

A mixture of the product from example 13, step 2 (0.73 g, 3.68 mmol), benzyl alcohol (9.4 g, 87 mmol) and K-t-BuO was stirred at 125° C. for 4.5 h. The reaction mixture was purified by silica gel chromatography (13'5 cm) using CHCl$_3$/MeOH (7:3 followed by 9: 1) as eluent. Solvents were evaporated off and the residue was redissolved in ethyl acetate. Filtration and concentration in vacuo furnished 0.90 g (90%) of the title compound as a beige oil. HRMS m/z calcd for $C_{15}H_{18}N_4O$ (M)$^+$ 270.1481, found 270.1482. Anal. ($C_{15}H_{18}N_4O$) C, H, N.

*This compound was also characterized as its maleate salt: mp 155–156° C. HRMS m/z calcd for $C_{15}H_{18}N_4O$ (M)$^+$ 270.1481, found 270.1482. Anal. ($C_{15}H_{18}N_4O.C_4H_4O_4$) C, H, N.

Example 21

2-Phenoxy-6-(1-piperazinyl)pyrazine

A mixture of the product obtained in example 13, step 2 (1.97 g, 9.92 mmol), phenol (2.43 g, 25.8 mmol), CuO (1.0 g, 12.6 mmol), and K$_2$CO$_3$ (1.43 g, 10.3 mmol) in dioxane (2 mL) was stirred for 4.5 h at 165° C. in a sealed pyrex tube. The reaction mixture was diluted with CHCl$_3$ and filtered through a pad of Celite. The pad was washed with several portions of CHCl$_3$/MeOH (95:5). Solvent removal in vacuo furnished a dark brown oil which was purified by column chromatography on silica gel (14×5 cm) using CHCl$_3$/MeOH (95:5, followed by 90:10) as eluent. The brown oil (1.66 g) was subjected to repeated column chromatography, first on silica gel (18×4 cm) using CHCl$_3$/MeOH (9:1) as eluent and finally on alumina (4×5 cm) using ether/MeOH (95:5) as eluent. This furnished 1.37 g (54%) of the title compound as a light beige oil. HRMS m/z calcd for $C_{14}H_{16}N_4O$ (M)$^+$ 256.1324, found 256.1321. Anal. ($C_{14}H_{16}N_4O$) C, H, N.

Example 22

2-(1-Phenylethoxy)-6-(1-piperazinyl)pyrazine

Step 1: 2-Chloro-6-(1-phenylethoxy)pyrazine

K-t-BuO (2.1 g, 18.7 mmol) was added to a stirred solution of 1-phenyl-1-ethanol (2.45 g, 20.1 mmol) in dioxane (30 mL) at 0° C. (ice-bath). After 10 min of stirring, 2,6-dichloropyrazine (2.49 g, 16.7 mmol) was added whereupon the reaction mixture turned orange colored. After being stirred for a further 1.5 h, ether was added and the mixture was filtered. Concentration in vacuo furnished an orange colored oil that was purified by silica gel chromatography (15×5 cm) using n-hexane ethyl acetate (9:1) as eluent. This gave 3.29 g (84%) of the title compound as a colorless oil. HRMS m/z calcd for $C_{12}H_{11}ClN_2O$ (M)$^+$ 234.0560, found 234.0551.

Step 2: 2-(1-Phenylethoxy)-6-(1-piperazinyl) pyrazine

A mixture of the product from step 1 above (1.53 g, 6.5 mmol), piperazine (1.62 g, 18.9 mmol) and K$_2$CO$_3$ (0.90 g, 6.5 mmol) in acetonitrile (6 mL) was heated in a sealed pyrex flask at 90° C. for 3.5 h. The reaction mixture was diluted with dichloromethane, filtered and concentrated in vacuo. The semi-solid residue was purified by silica gel chromatography (13×4 cm) using CHCl$_3$/MeOH (9:1) as eluent. Solvents were evaporated off and the remaining oil was redissolved in CHCl$_3$, filtered through a short plug of alumina and concentrated in vacuo. This gave 1.34 g (72%) of the title compound as an oil that solidified when refrigerated. HRMS m/z calcd for $C_{16}H_{20}N_4O$ (M)$^+$ 284.1637, found 284.1650. Anal. ($C_{16}H_{20}N_4O.C_4H_4O_4$) C, H, N.

Example 23

2-(2-Fluoroethoxy)-6-(1-piperazinyl)pyrazine, Maleate

Step 1: 2-Chloro-6-(2-fluoroethoxy)pyrazine

K-t-BuO (1.32 g, 11.8 mmol) was added portionwise to a stirred mixture of 2-fluoroethanol (2.16 g, 33.7 mmol) and 2,6-dichloropyrazine (1.61 g, 10.8 mmol) in dioxane (2 mL) at 0° C. (ice-bath). The reaction mixture was then stirred at room temperature for 1 hour, diluted with dichloromethane, filtered, and concentrated in vacuo. The residue was purified by column chromatography on silica gel (19×4 cm) using n-hexane/ethyl acetate (85:15) as eluent. This furnished 1.49 g (78%) of the title compound as a beige liquid. Anal. ($C_6H_6FClN_2O$) C, H, N.

Step 2: 2-(2-Fluoroethoxy)-6-(1-piperazinyl) pyrazine, Maleate

A mixture of the product from step 1 above (0.94 g, 5.31 mmol), piperazine (1.40 g, 16.3 mmol) and K$_2$CO$_3$ (0.81 g, 5.9 mmol) in acetonitrile (5 mL) was stirred at room temperature for 8.5 h and at 65° C. for 4 h. The reaction mixture was diluted with dichloromethane, filtered and concentrated in vacuo. The semi-solid residue was purified by silica gel chromatography (17×4 cm) using CHCl$_3$/MeOH (9:1) as eluent. Solvents were evaporated off and the remaining oil (0.73 g) was redissolved in ether/CHCl$_3$ (1:1) and filtered through a short (4 cm) plug of alumina using ether/MeOH (96:4) as eluent. Solvents were evaporated off and the residue was redissolved in ether and K$_2$CO$_3$ was added. Filtration and concentration in vacuo furnished 0.57 g (47%) of the free base of the title compound as an oil which was converted into its maleate salt. Recrystallization from MeOH/ether furnished 0.58 g of the title compound as a white powder. Anal. ($C_{10}H_{15}FN_4O.C_4H_4O_4$) C, H, N.

Example 24

2-(Cyclopentylmethoxy)-6-(1-piperazinyl)pyrazine

Step 1: 2-Chloro-6-(cyclopentylmethoxy)pyrazine

K-t-BuO (1.65 g, 14.7 mmol) was added portionwise to a stirred mixture of cyclopentanemethanol (2.99 g, 29.9 mmol) and 2,6-dichloropyrazine (1.90 g, 12.8 mmol) in dioxane (6 mL) at 0° C. (ice-bath). The reaction mixture was then stirred for 2.5 h, while the temperature was allowed to reach room temperature. The reaction mixture was diluted with dichloromethane/ether (1:1), filtered, and concentated in vacuo. The beige liquid was purified by column chromatography on silica gel (18×4 cm) using n-hexane/ethyl acetate (94:6) as eluent. Two chromatographic runs afforded 1.66 g (61%) of the title compound as a colorless oil. HRMS m/z calcd for $C_{10}H_{13}ClN_2O$ (M)$^+$212.0716, found 212.0723. Anal. ($C_{10}H_{13}ClN_2O$) C, H, N.

Step 2: 2-(Cyclopentylmethoxy)-6-(1-piperazinyl) pyrazine

A mixture of the product from step 1 above (1.12 g, 5.27 mmol), piperazine (1.36 g, 15.8 mmol) and $K_2CO_3$ (0.77 g, 5.6 mmol) in acetonitrile (5 mL) was stirred at 100° C. for 4.5 h in a sealed pyrex flask. The reaction mixture was diluted with dichloromethane, filtered and concentrated in vacuo. The semi-solid residue was purified by silica gel chromatography (15×4 cm) using $CHCl_3$/MeOH (9:1) as eluent. Solvents were evaporated off and the remaining thick oil was redissolved in ether. Filtration and concentration in vacuo furnished 1.02 g (74%) of the title compound as a beige oil. HRMS m/z calcd for $C_{14}H_{22}N_4O$ $(M)^+$ 262.1794, found 262.1800. Anal. $(C_{14}H_{22}N_4O)$ C, H, N.

Example 25

2-Benzyl-6-(1-piperazinyl)pyrazine

Step 1: 2-Chloro-6-benzylpyrazine

The title compound was prepared in a 20 mmol-scale according to the procedure described in WO 94/26715 with a slight modification. The reaction was carried out at 50° C. for 8 h followed by 10 h at room temperature. Yield: 0.75 g (18%). HRMS m/z calcd for $C_{11}H_9ClN_2(M)^+$ 204.0454, found 204.0450.

Step 2: 2-Benzyl-6-(1-piperazinyl)pyrazine

A mixture of the product from step 1 above (0.83 g, 4.0 mmol), piperazine (1.1 g, 12.8 mmol) and $K_2CO_3$ (0.62 g, 4.49 mmol) in acetonitrile (7 mL) was stirred at 85° C. for 8.5 h. Thr reaction mixture was diluted with dichloromethane, filtered and concentrated in vacuo. The semi-solid residue was purified by silica gel chromatography (20×4 cm) using $CHCl_3$/MeOH (9:1) as eluent. The resulting oil was redissolved in $CHCl_3$ and filtered through a short (4 cm) plug of alumina using ether/MeOH (96:4) as eluent. Solvent removal in vacuo furnished 0.59 g (57%) of the title compound as an oil which became semi-solid upon refrigeration. HRMS m/z calcd for $C_{15}H_{18}N_4$ $(M)^+$ 254.1531, found 254.1527. Anal. $(C_{15}H_{18}N_4)$ C, H, N.

Example 26

2-(3,4-Dihydro-2H-chromen-4-yloxy)-6-(1-piperazinyl)pyrazine, Maleate

Step 1: 2-Chloro-6-(3,4-dihydro-2H-chromen-4-yloxy)pyrazine

K-t-BuO (1.28 g, 11.42 mmol) was added to a stirred solution of 4-chromanol (1.81 g, 12.0 mmol) in dioxane (30 mL) at 0° C. (ice-bath). After being stirred for 5 min at room temperature, the mixture was chilled to 0° C. (ice-bath) and 2,6-dichloropyrazine (1.49 g, 10.0 mmol) was added. The reaction mixture was stirred at room temperature for 15 min and diluted with dichloromethane. Filtration and concentration in vacuo furnished an orange thick oil which was purified by chromatography on silica gel (15×4 cm) using n-hexane/ethyl acetate (8:2) as eluent. This furnished 1.87 g (71%) of the title compound as a colorless oil. HRMS m/z calcd for $C_{13}H_{11}ClN_2O_2$ $(M)^+$ 262.0509, found 262.0520. Anal. $(C_{13}H_{11}ClN_2O_2)$ C, H, N.

Step 2: 2-(3,4-Dihydro-2H-chromen-4-yloxy)-6-(1-piperazinyl)pyrazine, Maleate

A mixture of the product from step 1 above (1.53 g, 5.81 mmol), piperazine (1.45 g, 16.9 mmol) and $K_2CO_3$ (0.80 g, 5.81 mmol) in acetonitrile (10 mL) was heated in a sealed pyrex flask at 110° C. for 6.5 h. The reaction mixture was diluted with $CHCl_3$, filtered and concentrated in vacuo. The semi-solid residue was purified by column chromatography on silica (13×4 cm) using $CHCl_3$/MeOH (9:1) as eluent. The free base of the title compound was obtained as a viscous oil (1.76 g, 97%) which was converted to its maleate salt. Recrystallization from MeOH/ether furnished 1.78 g (74%) of the title compound as a light yellow powder: mp 179.5–182° C. HRMS m/z calcd for $C_{17}H_{20}N_4O_2$ $(M)^+$ 312.1586, found 312.1581. Anal. $(C_{17}H_{20}N_4O_2 \cdot C_4H_4O_4)$ C, H, N.

Example 27

2-[2-(4-Dimethylaminophenyl)ethoxy]-6-(1-piperazinyl)pyrazine, Maleate

Step 1: 2-Chloro-6-[2-(4-dimethylaminophenyl)ethoxy]pyrazine

K-t-BuO (2.27 g, 20.3 mmol) was added to a stirred solution of 4-(dimethylamino)phenethyl alcohol (3.55 g, 21.5 mmol) in dioxane (35 mL) at 0° C. (ice-bath). After being stirred for 5 min at 0° C. and 12 min at room temperature, the mixture was chilled to 0° C. (ice-bath) and 2,6-dichloropyrazine (2.62 g, 17.6 mmol) was added. The reaction mixture was stirred at 0° C. for 5 min and at room temperature for 20 min and diluted with dichloromethane/ether (1:1). Filtration through a pad of Celite, covered with $K_2CO_3$, and concentration in vacuo furnished a yellow oil. This material was purified by chromatography on silica gel (15×5 cm) using n-hexane/ethyl acetate (85:15). A second chromatograhic run on silica gel (14×5 cm) using n-hexane/ethyl acetate (88:12) furnished 3.91 g (80%) of the title compound as a colorless oil. Anal. $(C_{14}H_{16}ClN_3O)$ C, H, N.

Step 2: 2-[2-(4-Dimethylaminophenyl)ethoxy]-6-(1-piperazinyl)pyrazine, Maleate

A mixture of the product from step 1 above (1.83 g, 6.59 mmol), piperazine (1.69 g, 19,6 mmol) and $K_2CO_3$ (0.92 g, 6.7 mmol) in acetonitrile (25 mL) was heated under reflux for 8.5 h. The reaction mixture was diluted with dichloromethane, filtered through a pad of Celite, and concentrated in vacuo. The semi-solid residue was purified by column chromatography on silica (13×4 cm) using $CHCl_3$/MeOH (92:8) as eluent. The free base of the title compound was obtained as a beige viscous oil (1.17 g, 54%) which was converted into its maleate salt. Recrystallization from MeOH/ether furnished 1.33 g of the title compound as a light yellow powder. HRMS m/z calcd for $C_{18}H_{25}N_5O$ $(M)^+$ 327.2059, found 327.2066. Anal. $(C_{18}H_{25}N_5O \cdot C_4H_4O_4)$ C, H, N.

Example 28

2-[2-(1H-Indol-1-yl)ethoxy]-6-(1-piperazinyl)pyrazine, Maleate

Step 1: 2-(1H-Indol-1-yl)ethanol*

A mixture of indole (5.71 g, 48.7 mmol), ethylene carbonate (4.72 g, 53.6 mmol) and $K_2CO_3$ (6.73 g, 48.7 mmol) in DMF (20 mL) was heated under reflux for 2 h. The reaction mixture was diluted with dichloromethane, filtered, and concentrated in vacuo. The light brown oily residue was purified by chromatography on silica gel (13×6 cm) using n-hexane/ethyl acetate (1:1) as eluent. This gave 1.78 g (23%) of the title compound as a beige oil. HRMS m/z calcd for $C_{10}H_{11}NO$ $(M)^+$ 161.0841, found 161.0849. Anal. ($C_{10}H_{11}NO.0.1H_2O$) C, H, N.

*Previously described in a) J. Med. Chem. 1992, 35, 994–1001; b) ibid. 1998, 41, 1619–1630.

Step 2: 2-Chloro-6-[2-(1H-indol-1-yl)ethoxy]pyrazine

K-t-BuO (0.67 g, 5.93 mmol) was added to a stirred solution of the product obtained in step 1 above (0.67 g, 5.93 mmol) in dioxane (20 mL) at 0° C. (ice-bath). After being stirred for 7 min at 0° C. and 5 min at room temperature, the mixture was chilled to 0° C. (ice-bath) and 2,6-dichloropyrazine (2.62 g, 17.6 mmol) was added. The yellowish reaction mixture was stirred at 0° C. for 20 min and at room temperature for 10 min and then diluted with dichloromethane. Drying ($K_2CO_3$), filtration, and concentration in vacuo furnished a beige oil. This material was purified by chromatography on silica gel (13×4 cm) using n-hexane/ethyl acetate (80:20). This furnished 1.39 g (94%) of the title compound as an oil that solidified upon standing. HRMS m/z calcd for $C_{14}H_{12}ClN_3O$ $(M)^+$ 273.0669, found 273.0671. Anal. ($C_{14}H_{12}ClN_3O$) C, H, N.

Step 3: 2-[2-(1H-Indol-1-yl)ethoxy]-6-(1-piperazinyl)pyrazine, Maleate

A mixture of the product from step 1 above (1.05 g, 3.84 mmol), piperazine (0.96 g, 11.1 mmol) and $K_2CO_3$ (0.53 g, 3.84 mmol) was heated at 85° C. for 7 h. The reaction mixture was diluted with $CHCl_3$, filtered, and concentrated in vacuo. The semi-solid residue was purified by chromatography on silica gel (11×4 cm) using $CHCl_3$/MeOH (9:1) as eluent. The resulting oil was redissolved in $CHCl_3$ and filtered through a short (4 cm) plug of alumina covered by $K_2CO_3$ using $CHCl_3$ as eluent. Solvent removal in vacuo furnished 1.02 g (82%) of the free base of the title compound as a beige oil which was converted into its maleate. Recrystallization from MeOH/ether furnished 1.00 g (75%) of the title compound as a light yellow powder: mp 160.5–163° C. HRMS m/z calcd for $C_{18}H_{21}N_5O$ $(M)^+$ 323.1746, found 323.1757. Anal. ($C_{18}H_{21}N_5O.C_4H_4O_4$) C, H, N.

Example 29

2-[2-(1H-Indol-3-yl)ethoxy]-6-(1-piperazinyl)pyrazine

Step 1: 2-Chloro-6-[2-(1H-indol-3-yl)ethoxy]pyrazine

K-t-BuO (2.32 g, 20.6 mmol) was added to a stirred solution of tryptophol (1.7 g, 10.6 mmol) in dioxane (30 mL) at 0° C. (ice-bath). After being stirred for 10 min at 0° C. and 10 min at room temperature, the mixture was chilled to 0° C. (ice-bath) and 2,6-dichloropyrazine (1.37 g, 9.17 mmol) was added. The yellowish reaction mixture was stirred at 0° C. for 30 min and for a further 20 min at room temperature. The mixture was diluted with dichloromethane, filtered, and concentrated in vacuo to furnish a brownish oil. This material was purified by chromatography on silica gel (14×5 cm) using n-hexane/ethyl acetate (75:25). This furnished 1.38 g (55%) of the title compound as a beige solid. Purity>90% by $^1$H NMR in $CDCl_3$.

Step 2: 2-[2-(1H-Indol-3-yl)ethoxy]-6-(1-piperazinyl)pyrazine

A mixture of the product from Step 1 above (1.07 g, 3.90 mmol), piperazine (0.98 g, 11.3 mmol) and $K_2CO_3$ (0.54 g, 3.9 mmol) in acetonitrile (11 mL) was heated at 85° C. for 5 h and at 110° C. for 8 h in a sealed pyrex flask. The reaction mixture was diluted with $CHCl_3$, filtered, and concentrated in vacuo. The semi-solid residue was purified by chromatography on silica gel (11×4 cm) using $CHCl_3$/MeOH (9: 1) as eluent. The resulting oil was redissolved in $CHCl_3$ and filtered through a short plug of alumina, covered by $K_2CO_3$, using $CHCl_3$ as eluent. Solvent removal in vacuo furnished 0.50 g (23%) of the title compound as an oil that solidified upon standing: mp 133–135° C. HRMS m/z calcd for $C_{18}H_{21}N_5O$ $(M)^+$ 323.1746, found 323.1763. Anal. ($C_{18}H_{21}N_5O$) C, H, N.

Example 30

4-[(4-Fluorobenzyl)oxy]-2-(1-piperazinyl)pyrimidine, Dihydrochloride

K-t-BuO (0.224 g, 2.00 mmol) was added to a solution of 4-fluorobenzyl alcohol (0.252 g, 2.00 mmol) in tert-butanol (5.4 mL). After being stirred for 30 min at room temperature, 2,4-dichloryrimidine (0.298 g, 2.00 mmol) in tert-butanol (2 mL) was added. The reaction mixture was stirred over night, poured into 5% aqueous NaOH and extracted with ethyl acetate. The organic layer was dried ($MgSO_4$) and concentrated in vacuo. A solution of piperazine (0.516 g, 6.00 mmol) in THF (5 mL) was added and the resulting mixture was stirred over night. The reaction mixture was concentrated and purified by chromatography on silica using dichloromethane/MeOH (1% HCl) (using gradient 99:1 to 9:1) to give 0.24 g (33%) of the title compound. MS m/z 288 $(M)^+$ and 5 fragments supporting the stated structure. HRMS m/z calcd for $C_{15}H_{17}FN_4O$ $(M)^+$ 288.1386, found 288.1378.

Example 31

4-[(2-Methoxybenzyl)oxy]-2-(1-piperazinyl)pyrimidine, Dihydrochloride

The title compound was prepared according to the procedure of example 30 starting from 2-methoxybenzyl alcohol (0.28 g, 2.0 mmol) to give 0.30 g (40%) of the title compound. MS m/z 300 $(M)^+$ and 3 fragments supporting the stated structure. HRMS m/z calcd for $C_{16}H_{20}N_4O_2$ $(M)^+$ 300.1586, found 300.1586.

Example 32

4-(Benzyloxy)-2-(1-piperazinyl)pyrimidine, Dihydrochloride

The title compound was prepared according to the procedure of example 30 starting from benzyl alcohol (0.22 g, 2.0 mmol) to give 0.23 g (31%) of the title compound. MS m/z 270 $(M)^+$ and 6 fragments supporting the stated structure. HRMS m/z calcd for $C_{15}H_{18}N_4O$ $(M)^+$ 270.1481, found 270.1488.

Example 33

4-(1-Piperazinyl)-2-{[3-(trifluoromethoxy)benzyl]oxy}pyrimidine, Trifluoroacetate

Step 1: 2-Chloro-4-[1-(4-tert-butoxycarbonyl)piperazinyl]pyrimidine*

1-tert-Butoxycarbonylpiperazine (3.72 g, 0.02 mol) was added to a stirred solution of 2,4-dichloropyrimidine (2.98 g, 0.02 mol) and diisopropylethylamine (2.58 g, 0.02 mol) in dichloromethane (200 mL). The reaction mixture was stirred at ambient temperature for 48 h and then concentrated under reduced pressure. The residue obtained was flash-chromatographed over silica using dichloromethane/ether (4:1) as eluent to afford 3.44 g (58%) of the title compound as a colourless solid whose NMR and MS spectra were in agreement with the expected structure. MS (ES+) m/z 299 and 301 (M+H)+.

*Previously described in WO 9911657.

Step 2: 2-Chloro-4-(1-piperazinyl)pyrimidine*

2-Chloro-4-[1-(4-tert-butoxycarbonyl)piperazinyl] pyrimidine. (2.00 g, 6.7 mmol; obtained in step 1 above) was dissolved in a 25% v/v solution of trifluoroacetic acid in dichloromethane (25 mL). The solution was stirred at room temperature for 40 min then the solvent was removed by evaporation under reduced pressure. The oily residue was partitioned between ethyl acetate and saturated aqueous sodium bicarbonate. The organic extract was dried and evaporated under reduced pressure to afford 1.04 g (79%) of the title compound as a colourless solid whose NMR and MS spectra were in agreement with the expected structure. MS (ES+) m/z 199 and 301 (M+H)+.

*Previously described in WO 9535293.

Step 3: 4-(1-Piperazinyl)-2-{[3-(trifluoromethoxy) benzyl]oxy}pyrimidine, Trifluoroacetate A solution of 2-chloro-4-(1-piperazinyl)pyrimidine (0.04 g, 0.2 mmol; obtained in Step 2 above) and 3-trifluoromethoxybenzyl alcohol (0.077 g, 0.4 mmol) in tetrahydrofuran (4.0 ml) was treated with a solution of K-t-BuO in tert-butanol (1M; 0.4 mL, 0.4 mmol). The resulting mixture was heated at 70° C. overnight then allowed to cool. The solvent was evaporated under reduced pressure then the crude reaction mixture partitioned between ethyl acetate (4.0 mL) and water (2.0 mL). The organic phase was evaporated then purified by preparative C-18 HPLC using $CH_3CN/H_2O$/TFA (gradient: $CH_3CN$ 20% to 97%, TFA 0.1%) to afford 11 mg (12%) of the title compound. Purity 85% (HPLC). MS (ES+) m/z 355 (M+H)+.

Example 34

2-[(3-Methoxybenzyl)oxy]-4-(1-piperazinyl) pyrimidine, Trifluoroacetate

The title compound was prepared according to the procedure of example 33, step 3 starting from 3-methoxybenzyl alcohol (0.055 g, 0.40 mmol) to give 5 mg (6%) of the expected product. Purity>90% (HPLC). MS (ES+) m/z 301 (M+H)+.

Example 35

2-{[3-(Benzyloxy)benzyl]oxy}-4-(1-piperazinyl) pyrimidine, Trifluoroacetate

The title compound was prepared according to the procedure of example 33, step 3 starting from 3-benzyloxybenzyl alcohol (0.086 g, 0.40 mmol) to give 10 mg (10%) of the expected product. Purity>90% (HPLC). MS (ES+) m/z 377 (M+H)+.

Example 36

2-[(3-Phenoxybenzyl)oxy]-4-(1-piperazinyl) pyrimidine, Trifluoroacetate

The title compound was prepared according to the procedure of example 33, step 3 starting from 3-phenoxybenzyl alcohol (0.08 g, 0.4 mmol) to give 8 mg (8%) of the expected product. Purity>90% (HPLC). MS (ES+) m/z 363 (M+H)+.

Example 37

2-(2-Naphthylmethoxy)-4-(1-piperazinyl) pyrimidine, Trifluoroacetate

The title compound was prepared according to the procedure of example 33, step 3 starting from 2-naphthylmethyl alcohol (0.063 g, 0.4 mmol) to give 10 mg (12%) of the expected product. Purity>90% (HPLC). MS (ES+) m/z 321 (M+H)+.

Example 38

4-(1-Piperazinyl)-2-{[3-(2-Trifluoromethyl)benzyl] oxy}pyrimidine, Trifluoroacetate A solution of. 2-chloro-4-[1-(4-tert-butoxycarbonyl) piperazinyl]pyrimidine (obtained in example 33, step 1; 0.04 g, 0.2 mmol) and 2-trifluoromethylbenzyl alcohol (0.035 g, 0.20 mmol) in tetrahydrofuran (2.0 mL) was treated with K-t-BuO in tert-butanol (1M; 0.2 mL, 0.2 mmol). The resulting mixture was heated at 65° C. overnight then allowed to cool. The solvent was evaporated under reduced pressure then the crude reaction mixtures partitioned between ethyl acetate (4.0 mL) and water (2.0 mL). The organic phase was evaporated then purified by preparative C-18 HPLC using $CH_3CN/H_2O$/TFA (gradient: $CH_3CN$ 20% to 97%, TFA 0.1%) to afford the BOC protected product. This material was then dissolved in a 25% (v/v) solution of trifluoroacetic acid in dichloromethane (5.0 mL) and allowed to stand at room temperature for 30 min. Removal of the solvent under reduced pressure gave 40 mg (44%) of the title compound. Purity >90% (HPLC). MS (ES+) m/z 339 (M+H)+.

Example 39

(2S)-1-[6-(Benzyloxy)-2-pyrazinyl]-2-methylpiperazine

Step 1: (3S)-3-Methyl-1-tritylpiperazine

To a solution of 2-(S)-methylpiperazine (2.62 g, 26.2 mmol) in dichloromethane (100 mL) was trityl chloride (7.30 g, 26.2 mmol) added and the mixture was stirred at ambient temperature for 1.5 h. The organic phase was washed (×1) with 1 M aqueous $K_2CO_3$, water, and brine. Drying ($MgSO_4$) and solvent removal in vacuo furnished a quantitative yield of the title compound as a glassy oil which solidified upon standing. This material was used directly in the next step.

Step 2: (2S)-1-(6-Chloro-2-pyrazinyl)-2-methylpiperazine

A mixture of 2–6-dichloropyrazine (1.10 g, 7.39 mmol), and the product from step 1 above (2.30 g, 6.72 mmol) and $K_2CO_3$ (1.0 g, 7.39 mmol) in dry DMF (40 mL) was stirred at 110° C. over night. The dark reaction mixture was filtered through a plug of silica and the solvent was removed under reduced pressure. The remaining oil was dissolved in $CHCl_3$/n-heptane (1:1) and filtered through a second plug of silica. The solvent was evaporated and the remaining yellow oil was suspended in EtOH (80 mL). 4 M aqueous HCl (2 mL) was added and the mixture was ultrasonicated for 20 min. The solvent was evaporated and the remaining oil was taken up between water/$CHCl_3$. The organic phase was made alkaline (11 M aqueous NaOH) and extracted twice with CHCl$_3$. The combined dried (MgSO$_4$) organic layers were concentrated in vacuo to afford 0.75 g (54%) of the title compound as a yellow oil. MS m/z 212/214 (M)$^+$($^{35}$Cl/$^{37}$Cl-isotope pattern). HRMS m/z calcd for C$_9$H$_{13}$ClN$_4$ (M)$^+$ 212.0829, found 212.0827.

Step 3: (2S)-1-[6-(Benzyloxy)-2-pyrazinyl]-2-methylpiperazine, Acetate

To a solution of (2S)-1-(6-chloro-2-pyrazinyl)-2-methylpiperazine (prepared in step 2 above; 0.16 g, 0.72 mmol) and benzyl alcohol (0.12 g, 1.1 mmol) in DMF (4 mL) was Na-t-BuO (0.14 g, 1.4 mmol) added and the mixture was stirred at 150° C. overnight. The solvent was evaporated off under reduced pressure and the residue taken up between CHCl$_3$/H$_2$O. The organic phase was concentrated and the crude product was purified by preparative C18-HPLC using acetonitrile/H$_2$O/HOAc with UV detection at 254 nm. Yield: 1 mg (0.4%). MS m/z 284 (M)$^+$. HRMS m/z calcd for C$_{16}$H$_{20}$N$_4$O (M)$^+$ 284.1637, found 284.1640.

Example 40

(2S)-1-[6-(Benzyloxy)-4-(trifluoromethyl)-2-pyridinyl]-2-methylpiperazine, Acetate Step 1: (2S)-1-[6-Chloro-4-(trifluoromethyl)-2-pyridinyl]-2-methylpiperazine The title compound, obtained as an oil, was prepared from the product of example 39, step 1 (2.62 g, 7.62 mmol) and 2,6-dichloro-4-trifluoromethylpyridine (1.81 g, 8.38 mmol) according to the procedure of example 39, step 2. Yield: 0.24 g (11%). MS m/z 279/281 (M)$^+$($^{35}$Cl/ $^{37}$Cl-isotope pattern). HRMS m/z calcd for C$_{11}$H$_{13}$ClF$_3$N$_3$ (M)$^+$ 279.0750, found 279.0751.

Step 2: (2S)-[6-(Benzyloxy)-4-(trifluoromethyl)-2-pyridinyl]-2-methylpiperazine, Acetate The title compund was prepared from the product of step 1 above (0.24 g, 0.86 mmol), benzyl alcohol (0.14 g, 1.29 mmol) and Na-t-BuO (0.165 g, 1.72 mmol) according to the procedure of example 39, step 3. MS m/z 351 (M)$^+$. HRMS m/z calcd for C$_{18}$H$_{20}$F$_3$N$_3$O (M)$^+$ 351.1558, found 351.1555.

Example 41

1-[6-(Benzyloxy)-2-pyrazinyl]-2-ethylpiperazine, Acetate

Step 1: 1-Benzyl-3-ethylpiperazine*

Benzyl bromide (38.7 g, 0.22 mol) was added in portions to a chilled (~0° C.) solution of 2-ethylpiperazine (25 g, 0.22 mol) in DMF (150 mL) with such a rate that the temperature did not exceed 20° C. The mixture was stirred for 1 h, the solvent was evaporated and the residue was partitioned between CHCl$_3$/0.5 M aqueous HCl. The aqueous phase was made alkaline (11 M NaOH) and extracted three times with CHCl$_3$. The combined organic phases were dried (MgSO$_4$) and concentrated. The resulting oil was purified by column chromatography on silica using CHCl$_3$, followed by CHCl$_3$/MeOH/NH$_4$OH (95:5:0.3) as eluents to give 31.6 g (70%) of the title compound as a yellowish oil. Anal. (C$_{13}$H$_{20}$N$_2$) H, N; C: calcd, 76.42; found, 75.85.

*Described in WO 00/76984.

Step 2: 4-Benzyl-1-(6-chloro-2-pyrazinyl)-2-ethylpiperazine

The title compound was prepared according to the procedure of example 39, step 2, starting from the product obtained in step 1 above (4.60 g, 22.5 mmol), 2,6-dichloropyrazine (3.90 g, 26.2 mmol) and K$_2$CO$_3$ (6.22 g, 45.0 mmol). Yield: 6.15 g (86%). MS m/z 316/318 (M)$^+$ ($^{35}$Cl/$^{37}$Cl-isotope pattern). HRMS m/z calcd for C$_{17}$H$_{21}$ClN$_4$ (M)$^+$ 316.1455, found 316.1455.

Step 3: 1-(6-Chloro-2-pyrazinyl)-2-ethylpiperazine

1-Choroethyl chloroformate (4.16 g, 29.1 mmol) was added dropwise under 2 h to a stirred solution of the product obtained in step 2 above (6.15 g, 19.4 mmol) in dry dichloromethane (75 mL) at 0° C. After being stirred at room temperature for 15 h, the reaction mixture was concentrated in vacuo and methanol was added. The mixture was heated at reflux for 2 h and concentrated. The residue was dissolved in CHCl$_3$ and passed through a short (4 cm) plug of silica gel using CHCl$_3$/MeOH (8:2) as eluent. Solvents were evaporated off and the residue was purified by chromatography on silica gel (12×5 cm) using CHCl$_3$/MeOH/Et$_3$N (95:5:0.2) as eluent. This provided 1.9 g (43%) of the title compound as an oil. MS m/z 226/228 (M)$^+$($^{35}$Cl/ $^{37}$Cl-isotope pattern). HRMS m/z calcd for C$_{10}$H$_{15}$ClN$_4$(M)$^+$ 226.0985, found 226.0986.

Step 4: 1-[6-(Benzyloxy)-2-pyrazinyl]-2-ethylpiperazine, Acetate

The title compund was prepared according to the procedure of example 39, step 3, starting from the product of step 3 above (0.163 g, 0.72 mmol), benzyl alcohol (0.12 g, 1.08 mmol) and Na-t-BuO (0.14 g, 1.4 mmol). Purity 90% (HPLC). MS m/z 298 (M)$^+$. HRMS m/z calcd for C$_{17}$H$_{22}$N$_4$O (M)$^+$ 298.1794, found 298.1802.

Example 42

2-[(4-Fluorobenzyl)oxy]-6-(1-piperazinyl)pyrazine

4-Fluorobenzyl alcohol (0.189 g, 1.50 mmol) was dissolved in THF (1 mL) and treated with NaH (0.065 g, 55% dispersion in mineral oil, 1.5 mmol). The reaction mixture was stirred at room temperature for 3 h. A solution of 2,6-dichloropyrazine (1.57 g, 10.5 mmol) in THF (7 mL) was added and the resulting mixture was stirred for 4 h at room temperature. Piperazine (0.580 g, 6.75 mmol) and K$_2$CO$_3$ (0.43 g, 4.5 mmol) were added and the mixture was stirred at 60° C. over night. Filtration, concentration, and purification by chromatography on silica gel using ethyl acetate/acetic acid/methanol/water (24:3:3:2) as eluent furnished 0.20 g (46%) of the title compound as a white solid: mp 183° C. HRMS m/z calcd for C$_{15}$H$_{17}$FN$_4$O(M)$^+$ 288.1386, found 288.1380. Anal. (C$_{15}$H$_{17}$FN$_4$O. 2.6H$_2$O) C, H, N.

Example 43

2-[(4-Methoxybenzyl)oxy]-6-(1-piperazinyl)pyrazine, Acetate

The title compound was prepared according to the procedure of example 42 starting from 4-methoxybenzyl alcohol (0.207 g, 1.50 mmol) and was isolated as a yellow solid. Yield: 0.79 g (67%). HRMS m/z calcd for C$_{16}$H$_{20}$N$_4$O$_2$ (M)$^+$ 300.1586, found 300.1584.

Example 44

2-[2-(4-Fluorophenyl)ethoxy]-6-(1-piperazinyl) pyrazine, 0.5 Acetate

The title compound was prepared according to the procedure of example 42 starting from 2-(4-fluorophenyl)

ethanol (0.210 g, 1.50 mmol) and was isolated as a yellow solid. Yield: 0.145 g (27%). HRMS m/z calcd for $C_{16}H_{19}FN_4O$ $(M)^+$ 302.1543, found 302.1554. Anal. ($C_{16}H_{19}FN_4O \cdot 0.5CH_3COOH$ $H_2O$) C, H, N.

Example 45

2-[2-(3-Methoxyphenyl)ethoxy]-6-(4-piperidinyloxy)pyrazine

Step 1: tert-Butyl 4-[(6-chloro-2-pyrazinyl)oxy]-1-piperidinecarboxylate

A mixture of 2,6-dichloropyrazine (5.00 g, 33.6 mmol), tert-butyl 4-hydroxy-1-piperidinecarboxylate (6.76 g, 33.6 mmol) and K-t-BuO (1 M in tert-butanol; 35 mL, 35 mmol) in $Et_3N$ (200 mL) was stirred at room temperature for 12 h. The reaction was quenched with water (50 mL) and concentrated in vacuo. The residue was dissolved in ethyl acetate, washed with saturated aqueous $KH_2PO_4$, dried ($MgSO_4$), and concentrated in vacuo. The residue was recrystallized from ethanol/water to give 9.50 g (90%) of the title compound as a white solid: mp 86–87° C.; MS m/z 313 $(M)^+$. Anal. ($C_{14}H_{20}ClN_3O_3$C, H, N.

Step 2: 2-Chloro-6-(4-piperidinyloxy)pyrazine

Aqueous 3.0 M HCl (12 mL) was added to a solution of the product obtained in Step 1 above (5.00 g, 15.9 mmol) in methanol (200 mL). The reaction mixture was stirred at 50° C. for 5 h and concentrated in vacuo. The residue was dissolved in water (50 mL) and basified with $K_3PO_4$. The aqueous phase was extracted with ethyl acetate (5×40 mL), dried ($MgSO_4$), and concentrated in vacuo. This gave 3.08 g (91%) of the title compound as a colorless oil which slowly decomposed upon standing. HRMS m/z calcd for $C_9H_{12}ClN_3O$ $(M)^+$ 213.0669, found 213.0663.

Step 3: 2-[2-(3-Methoxyphenyl)ethoxy]-6-(4-piperidinyloxy)pyrazine

A solution of the product obtained in Step 2 above (0.043 g, 0.20 mmol) in DMF (1.1 mL) was added to a mixture of 3-methoxyphenethyl alcohol (0.061 g, 0.40 mmol) and K-t-BuO (1.0 M in tert-butanol; 0.4 mL, 0.40 mmol) in DMF (0.8 mL). The reaction mixture was vortexed for 16 h at 50° C. under nitrogen, quenched with water (0.1 mL) and concentrated in vacuo. The residue was partitioned between water (2 mL) and 4 ethyl acetate (4 mL) and poured through a hydromatrix column, which was eluted with ethyl acetate/$Et_3N$ (95:5). Solvents were evaporated off and the residue was dissolved in methanol/water (50 mL) and loaded onto a conditioned weak cation exchange SPE column (1 g, Amberlyst CG-50 I). The column was washed with water (10 mL) and methanol (10 mL). The compound was eluted with aqueous 2.0 M $NH_3$ in methanol (20 m) and concentrated in vacuo. The residue was analysed for identity and purity by LC-UV/MS. Yield: 8 mg (12%). HRMS m/z calcd for $C_{18}H_{23}N_3O_3$ $(M)^+$ 329.1739, found 329.1743.

Example 46

2-(2-Phenylethoxy)-6-(4-piperidinyloxy)pyrazine

The title compound was prepared according the procedure of example 45, step 3, starting from 2-phenylethanol (49 mg, 0.40 mmol). The product was analysed for identity and purity by LC-UV/MS. Yield: 7 mg (12%). HRMS m/z calcd for $C_{17}H_{21}N_3O_2$ $(M)^+$ 299.1634, found 299.1630.

Example 47

2-(3-Phenoxypropoxy)-6-(4-piperidinyloxy)pyrazine

The title compound was prepared according the procedure of example 45, step 3, starting from 3-phenoxy-1-propanol (61 mg, 0.40 mmol). The product was analysed for identity and purity by LC-UV/MS. Yield: 28 mg (43%). HRMS m/z calcd for $C_{18}H_{23}N_3O_3$ $(M)^+$ 329.1739, found 329.1743.

Example 48

2-[(5-Phenylpentyl)oxy]-6-(4-piperidinyloxy)pyrazine

The title compound was prepared according the procedure of example 45, step 3, starting from 5-phenyl-1-pentanol (66 mg, 0.40 mmol). The product was analysed for identity and purity by LC-UV/MS. Yield: 17 mg (25%).

Example 49

2-{[3-(Benzyloxy)benzyl]oxy}-6-(4-piperidinyloxy)pyrazine

The title compound was prepared according the procedure of example 45, step 3, starting from 3-benzyloxybenzyl alcohol (86 mg, 0.40 mmol). The product was analysed for identity and purity by LC-UV/MS. Yield: 43 mg (55%). HRMS m/z calcd for $C_{23}H_{25}N_3O_3$ $(M)^+$ 391.1896, found 391.1905.

Example 50

2-[1-(2-Methoxyphenyl)ethoxy]-6-(1-piperazinyl)pyrazine

Step 1: 2-Chloro-6-[1-(2-methoxyphenyl)ethoxy]pyrazine

K-t-BuO (0.67 g, 5.97 mmol) was added to a stirred solution of 1-(2-methoxyphenyl)ethanol (0.96 g, 6.28 mmol) in dioxane (15 mL) at 0° C. (ice-bath). After 5 min of stirring at room temperature, the reaction mixture was chilled to 0° C. (ice-bath) and 2,6-dichloropyrazine (0.78 g, 5.23 mmol) was added whereupon the reaction mixture turned yellow. After being stirred for 35 min, dichloromethane and $K_2CO_3$ were added and the mixture was filtered. Concentration in vacuo furnished a yellow oil that was purified by silica gel chromatography (15×4 cm) using n-hexane ethyl acetate (8:2) as eluent. This gave 1.21 g (92%) of the title compound as a colorless oil. HRMS m/z calcd for $C_{13}H_{13}ClN_2O_2$ $(M)^+$ 264.0666, found 264.0677. Anal. ($C_{13}H_{13}ClN_2O_2$) C, H, N.

Step 2: 2-[1-(2-Methoxyphenyl)ethoxy]-6-(1-piperazinyl)pyrazine

A mixture of the product from step 1 above (0.93 g, 3.53 mmol) piperazine (0.88 g, 10.2 mmol) and $K_2CO_3$ (0.49 g, 3.53 mmol) in acetonitrile (7 mL) was heated in a sealed pyrex flask at 90° C. for 6.5 h. The reaction mixture was diluted with dichloromethane, filtered and concentrated in vacuo. The semi-solid residue was purified by silica gel chromatography (13×4 cm) using $CHCl_3$/MeOH (9:1) as eluent. Solvents were evaporated off and the remaining oil was redissolved in $CHCl_3$, filtered through a short plug of alumina, covered with $K_2CO_3$, using $CHCl_3$ as eluent. Solvent removal in vacuo gave 0.74 g (67%) of the title compound as a beige oil. HRMS m/z calcd for $C_{17}H_{22}N_4O_2$ $(M)^+$ 314.1743, found 314.1733. Anal. ($C_{17}H_{22}N_4O_2 \cdot 0.5H_2O$) C, H, N.

Example 51

1-[6-(Benzyloxy)-2-pyrazinyl]-trans-2,5-dimethylpiperazine

Step 1: 1-(6-Chloro-2-pyrazinyl)-trans-2,5-dimethylpiperazine

A mixture of 2,6-dichloropyrazine (0.40 g, 2.68 mmol), trans-2,5-dimethylpiperazine (0.62 g, 5.43 mmol), $K_2CO_3$ (0.41 g, 3.0 mmol) in acetonitrile (5 mL) was stirred at 90° C. for 6 h in a sealed pyrex tube. After cooling, the reaction mixture was filtered and concentrated in vacuo. The oily residue was purified by column chromatography on silica gel using $CHCl_3$/MeOH (9:1) as eluent. This furnished 0.15 g (25%) of the title compound as an oil. HRMS m/z calcd for $C_{10}H_{15}ClN_4$ $(M)^+$ 226.0985, found 226.0983.

Step 2: 1-[6-(Benzyloxy)-2-pyrazinyl]-trans-2,5-dimethylpiperazine

The title compound was prepared according to the procedure of example 20, starting from 1-(6-chloro-2-pyrazinyl)-trans-2,5-dimethylpiperazine (1.23 g, 5.40 mmol; obtained in step 1 above), benzyl alcohol (8.36 g, 77.3 mmol), and K-t-BuO (1.99 g, 17.7 mmol). The reaction mixture was heated at 95° C. for 5.5 h. The yield of the title compound was 0.47 g (29%) which was obtained as an oil. Purity 99% (HPLC). MS m/z 298 $(M)^+$. HRMS m/z calcd for $C_{17}H_{22}N_4O$ $(M)^+$ 298.1794, found 298.1798.

Example 52

2-[2-(2,3-Dimethoxyphenyl)ethoxy]-6-(1-piperazinyl)pyrazine, Maleate

The title compound was prepared according to the procedure of example 50, step 2, starting from 2-chloro-6-[2-(2,3-dimethoxyphenyl)ethoxy]pyrazine [0.65 g, 2.2 mmol; obtained according to the procedure of example 50, step 1, starting from 2-(2,3-dimethoxyphenyl)ethan-1-ol], piperazine (0.57 g, 6.7 mmol) and $K_2CO_3$ (0.31 g, 2.22 mmol). The free base of the title compound was converted into its maleate salt. Recrystallization from MeOH-ether furnished 0.45 g (44%) of the title compound. Purity 98% (HPLC). MS m/z 345 $(M+H)^+$. HRMS m/z calcd for $C_{18}H_{24}N_4O_3$ $(M)^+$ 344.1848, found 344.1861.

Example 53

2-[2-(2-Fluorophenyl)ethoxy]-6-(1-piperazinyl) pyrazine, Maleate

The title compound was prepared according to the procedure of example 50, step 2, starting from 2-chloro-6-[2-(2-fluorophenyl)ethoxy]pyrazine (2.76 g, 10.9 mmol; obtained according to the procedure of example 50, step 1, starting from 2-fluorophenethyl alcohol), piperazine (2.91 g, 33.8 mmol) and $K_2CO_3$ (1.51 g, 10.9 mmol). The yield of the free base of the title compound was 1.88 g (57%) which was converted into its maleate salt. Recrystallization from MeOH-ether furnished 2.11 g of the title compound. Purity 100% (HPLC). MS m/z 303 $(M+H)^+$. HRMS m/z calcd for $C_{16}H_{19}FN_4O$ $(M)^+$ 302.1543, found 302.1550.

Example 54

2-[(2,3-Dimethoxybenzyl)oxy]-6-(1-piperazinyl)pyrazine

The title compound was prepared according to the procedure of example 50, step 2, starting from 2-chloro-6-[(2,3-dimethoxybenzyl)oxy]pyrazine (2.51 g, 8.93 mmol; obtained according to the procedure of example 50, step 1, starting from 2,3-dimethoxybenzyl alcohol), piperazine (2.38 g, 27.7 mmol) and $K_2CO_3$ (1.23 g, 8.9 mmol). The yield of the title compound was 1.66 g (56%) which was obtained as an oil. Purity 100% (HPLC). MS m/z 331 $(M+H)^+$. HRMS m/z calcd for $C_{17}H_{22}N_4O_3$ $(M)^+$ 330.1692, found 330.1690.

Example 55

2-(2,3-Dihydro-1H-inden-1-ylmethoxy)-6-(1-piperazinyl)pyrazine, Maleate

The title compound was prepared according to the procedure of example 50, step 2, starting from 2-chloro-6-(2,3-dihydro-1H-inden-1-ylmethoxy)pyrazine (3.22 g, 13.1 mmol; obtained according to the procedure of example 50, step 1, starting from 1-indanol), piperazine (3.49 g, 40.5 mmol) and $K_2CO_3$ (1.8 g, 13.0 mmol). The yield of the free base of the title compound was 2.19 g (57%) which was obtained as an oil. The free base was converted into its maleate salt. Purity 100% (HPLC). MS m/z 296 $(M)^+$. HRMS m/z calcd for $C_{17}H_{20}N_4O$ $(M)^+$ 296.1637, found 296.1643.

Example 56

2-(4-Phenoxybutoxy)-6-(1-piperazinyl)pyrazine

The title compound was prepared according to the procedure of example 50, step 2, starting from 2-chloro-6-(4-phenoxybutoxy)pyrazine (1.99 g, 7.14 mmol; obtained according to the procedure of example 50, step 1, starting from 4-phenoxy-1-butanol*), piperazine (1.84 g, 21.4 mmol) and $K_2CO_3$ (0.99 g, 7.14 mmol). The yield of the title compound was 1.52 g (65%) which was obtained as an oil. Purity100% (HPLC). MS m/z 329 $(M+H)^+$. HRMS m/z calcd for $C_{18}H_{24}N_4O_2$ $(M)^+$ 328.1899, found 328.1894.

*Prepared by reduction ($LiAlH_4$) of the corresponding acid (cf J. Org. Chem. 1965, 30, 2441–2447; ibid. 1968, 33, 2271–2284).

Example 57

2-[(5-Phenoxypentyl)oxy]-6-(1-piperazinyl)pyrazine

The title compound was prepared according to the procedure of example 50, step 2, starting from 2-chloro-6-[(5-phenoxypentyl)oxy]pyrazine (2.06 g, 7.03 mmol; obtained according to the procedure of example 50, step 1, starting from 5-phenoxy-1-pentanol*), piperazine (1.88 g, 21.8 mmol) and $K_2CO_3$ (0.97 g, 7.03 mmol). The yield of the title compound was 1.15 g (48%) which was obtained as a white solid. Purity 100% (HPLC). MS m/z 343 $(M+H)^+$. HRMS m/z calcd for $C_{19}H_{26}N_4O_2$ $(M)^+$ 342.2056, found 342.2054.

*Described in J. Org. Chem. 1968, 33, 2271–2284.

Example 58

2-[(2,5-Dimethoxybenzyl)oxy]-6-(1-piperazinyl)pyrazine

The title compound was prepared according to the procedure of example 50, step 2, starting from 2-chloro-6-[(2,5-dimethoxybenzyl)oxy]pyrazine (1.02 g, 3.63 mmol; obtained according to the procedure of example 50, step 1, starting from 2,5-dimethoxybenzyl alcohol), piperazine (0.94 g, 10.9 mmol) and $K_2CO_3$ (0.50 g, 3.63 mmol). The yield of the title compound was 0.64 g (53%) which was obtained as a beige solid. Purity 100% (HPLC). MS m/z 331 $(M+H)^+$. HRMS m/z calcd for $C_{17}H_{22}N_4O_3$ $(M)^+$ 330.1692, found 330.1692.

Example 59

2-[2-(3,4-Dimethoxyphenyl)ethoxy]-6-(1-piperazinyl)pyrazine, Maleate

The title compound was prepared according to the procedure of example 50, step 2, starting from 2-chloro-6-[2-

(3,4-dimethoxyphenyl)ethoxy]pyrazine [2.13 g, 7.23 mmol; obtained according to the procedure of example 50, step 1, starting from 2-(3,4-dimethoxyphenyl)ethan-1-ol], piperazine (1.93 g, 22.4 mmol) and $K_2CO_3$ (1.0 g, 7.2 mmol). The yield of the title compound was 1.72 g (69%) which was obtained as a beige oil. Purity 100% (HPLC). MS m/z 345 $(M+H)^+$. The free base was converted into ints maleate salt. HRMS m/z calcd for $C_{18}H_{24}N_4O_3$ $(M)^+$ 344.1848, found 344.1832.

Example 60

2-{[2-(2-Phenylethyl)benzyl]oxy}-6-(1-piperazinyl)pyrazine

The title compound was prepared according to the procedure of example 50, step 2, starting from 2-chloro-6-{[2-(2-phenylethyl)benzyl]oxy}pyrazine (1.72 g, 5.30 mmol; obtained according to the procedure of example 50, step 1, starting from 2-phenethylbenzyl alcohol), piperazine (1.37 g, 16.0 mmol) and $K_2CO_3$ (0.73 g, 5.3 mmol). The yield of the title compound was 1.38 g (69%) which was obtained as an oil. Purity 100% (HPLC). MS m/z 375 $(M+H)^+$. HRMS m/z calcd for $C_{23}H_{26}N_4O$ $(M)^+$ 374.2107, found 374.2113.

Example 61

2-[(3-Phenoxybenzyl)oxy]-6-(1-piperazinyl)pyrazine

The title compound was prepared according to the procedure of example 50, step 2, starting from 2-chloro-6-[(3-phenoxybenzyl)oxy]pyrazine (1.99 g, 6.36 mmol; obtained according to the procedure of example 50, step 1, starting from 3-phenoxybenzyl alcohol), piperazine (1.94 g, 22.5 mmol) and $K_2CO_3$ (0.88 g, 6.4 mmol). The yield of the title compound was 1.58 g (69%) which was obtained as an oil. Purity 100% (HPLC). MS m/z 363 $(M+H)^+$. HRMS m/z calcd for $C_{21}H_{22}N_4O_2$ $(M)^+$ 362.1743, found 362.1739.

Example 62

(2R)-1-[6-(Benzyloxy)-2-pyrazinyl]-2-methylpiperazine, Maleate

Step 1: (3R)-3-Methyl-1-tritylpiperazine

The title compound was prepared according to the procedure of Example 39, step 1, with the exception that (2R)-methylpiperazine was substituted for (2S)-methylpiperazine. The title compound was obtained as a light yellow crispy solid.

Step 2: (2R)-1-(6-Chloro-2-pyrazinyl)-2-methylpiperazine, Maleate

A mixture of 2.6-dichloropyrazine (2.33 g, 15.7 mmol), the product from step 1 above (5.11 g, 14.9 mmol) and $K_2CO_3$ (3.09 g, 22.4 mmol) in dry DMF (50 mL) was stirred at 120° C. for 7.5 h. The dark reaction mixture was diluted with ether and solids were filtered off. The filter cake was washed with $CHCl_3$. The filtrate was concentrated under reduced pressure. The residue was redissolved in $CHCl_3$ (150 mL) and 5M aqueous HCl (20 mL) was added and the mixture was stirred at room temperature 8.5 h. A solution of 5 M aqueous NaOH (25 mL) was added carefully and the layers were separated. The aqueous layer was extracted with $CHCl_3$ (2×150 mL). The combined, dried ($K_2CO_3$), organic phases were concentrated in vacuo. The brownish oily residue was purified by silica gel chromatography (bed size: 11×6 cm) using $CHCl_3$/MeOH (92:8) as eluent. The yield of the free base of the title compound was 1.74 g (55%) which was obtained as a tan colored oil. A portion (0.41 g, 1.9 mmol) of the free base was converted into its maleate salt. Purity 99% (HPLC). HRMS m/z calcd for $C_9H_{13}ClN_4$ $(M)^+$ 212.0829, found 212.0819.

Step 3: (2R)-1-[6-(Benzyloxy)-2-pyrazinyl]-2-methylpiperazine, Maleate

K-t-BuO (2.07 g, 18.4 mmol) was added to a mixture of (2R)-1-(6-chloro-2-pyrazinyl)-2-methylpiperazine (prepared in step 2 above; 1.31 g, 6.15 mmol) and benzyl alcohol (10.0 g, 92.5 mmol). After being stirred for 7 h at 95° C., the mixture was applied onto a bed of silica (12×6 cm). Elution with $CHCl_3$/MeOH (97:3 followed by 92:8) furnished 1.44 g (82%) of the free base of the title compound as a light yellow oil. The free base was converted into its maleate salt. Purity 99% (HPLC). MS m/z 284 $(M)^+$. HRMS m/z calcd for $C_{16}H_{20}N_4O$ $(M)^+$ 284.1637, found 284.1633.

Example 63

(2R)-1-[6-(Benzyloxy)-4-(trifluoromethyl)-2-pyridinyl]-2-methylpiperazine

The title compound was prepared according to the procedure of example 40 with the exceptions that (2R)-methylpiperazine was substituted for (2S)-methylpiperazine in step 1 and that N-deprotection (N-detritylation) in step 2 was carried out using trifluoroacetic acid in dichloromethane (3:1). MS m/z 352 $(M+H)^+$. HRMS m/z calcd for $C_{18}H_{20}F_3N_3O$ $(M)^+$ 351.1558, found 351.1549.

Example 64

(2R)-1-[6-(Benzyloxy)-2-pyridinyl]-2-methylpiperazine

The title compound was prepared according to the procedure of example 39 with the exceptions that (2R)-methylpiperazine was substituted for (2S)-methylpiperazine in step 1, and that 2,6-dichloropyridine was substituted for 2,6-dichloropyrazine in step 2, and further that N-deprotection (N-detritylation) in step 2 was carried out using trifluoroacetic acid in dichloromethane (3:1). MS m/z 284 $(M+H)^+$.

Example 65

2-(1-Piperazinyl)-6-{[3-(1H-pyrrol-1-yl)-2-thienyl]methoxy}pyrazine

Step 1: 2-Chloro-6-{[3-(1H-pyrrol-1-yl)-2-thienyl]methoxy}pyrazine

The title compound was prepared according to the procedure of example 50, step 1, starting from 3-(pyrrol-1-yl)thiophene-2-methanol (2.5 g, 14 mmol), K-t-BuO (1.43 g, 12.7 mmol) and 2,6-dichloropyrazine (1.73 g, 11.6 mmol). The yield of the title compound was 3.05 g (90%) and was obtained as an oil. Anal. ($C_{13}H_{10}ClN_3OS$) C, H, N.

Step 2: 2-(1-Piperazinyl)-6-{[3-(1H-pyrrol-1-yl)-2-thienyl]methoxy}pyrazine

The title compound was prepared according to the procedure of example 50, step 2, starting from the product obtained in step 1 above (1.78 g, 6.10 mmol), piperazine (1.58 g, 18.3 mmol) and $K_2CO_3$ (0.86 g, 6.2 mmol). The yield of the title compound was 1.43 g (69%) and was obtained as a beige solid. HRMS m/z calcd for $C_{17}H_{19}N_5OS$ (M)+ 341.1310, found 341.1301.

Example 66

2-{[3-(Benzyloxy)benzyl]oxy}-6-(1-piperazinyl)pyrazine

Step 1: 2-{[3-(Benzyloxy)benzyl]oxy}-6-chloropyrazine

The title compound was prepared according to the procedure of example 50, step 1, starting from 3-benzyloxybenzyl alcohol (3.46 g, 16.2 mmol), K-t-BuO (1.69 g, 15.1 mmol) and 2,6-dichloropyrazine (1.97 g, 13.2 mmol). The yield of the title compound was 2.64 g (61%) and was obtained as a semisolid. Anal. ($C_{18}H_{15}ClN_2O_2$) C, H, N.

Step 2: 2-{[3-(Benzyloxy)benzyl]oxy}-6-(1-piperazinyl)pyrazine

The title compound was prepared according to the procedure of example 50, step 2, starting from the product obtained in step 1 above (1.62 g, 4.96 mmol), piperazine (1.28 g, 14.9 mmol) and $K_2CO_3$ (0.70 g, 5.1 mmol). The yield of the title compound was 1.16 g (62%) and was obtained as an oil. HRMS m/z calcd for $C_{22}H_{24}N_4O_2$ (M)+ 376.1899, found 376.1890. Anal. ($C_{22}H_{24}N_4O_2$) C, H, N.

Example 67

2-(1-Piperazinyl)-6-[3-(2-pyridinyl)propoxy]pyrazine, Maleate

Step 1: 2-Chloro-6-[3-(2-pyridinyl)propoxy]pyrazine

The title compound was prepared according to the procedure of example 50, step 1, starting from 2-pyridinepropanol (4.08 g, 29.7 mmol), K-t-BuO (3.17 g, 28.3 mmol) and 2,6-dichloropyrazine (3.69 g, 24.8 mmol). The yield of the title compound was 5.18 g (84%) and was obtained as an oil. Anal. ($C_{12}H_{12}ClN_3O$) C, H, N.

Step 2: 2-(1-Piperazinyl)-6-[3-(2-pyridinyl)propoxy]pyrazine, Maleate

The title compound was prepared according to the procedure of example 50, step 2, starting from the product obtained in step 1 above (1.80 g, 7.20 mmol), piperazine (1.87 g, 21.6 mmol) and $K_2CO_3$ (1.0 g, 7.2 mmol). The free base (1.23 g) of the title compound was converted into its maleate. Recrystallization from MeOH-ether furnished 1.32 g (38%) of the title compound. HRMS m/z calcd for $C_{16}H_{21}N_5O$ (M)+ 299.1758, found 299.1748. Anal. ($C_{16}H_{21}N_5O \cdot 1.5C_4H_4O_4 \cdot 0.5H_2O$) C, H, N.

Example 68

2-[(3,5-Dimethoxybenzyl)oxy]-6-(1-piperazinyl)pyrazine, Maleate

Step 1: 2-Chloro-6-[(3,5-dimethoxybenzyl)oxy]pyrazine

The title compound was prepared according to the procedure of example 50, step 1, starting from 3,5-dimethoxybenzyl alcohol (2.16 g, 12.8 mmol), K-t-BuO (1.34 g, 11.9 mmol) and 2,6-dichloropyrazine (1.59 g, 10.7 mmol). The yield of the title compound was 2.56 g (84%) and was obtained as a white solid. HRMS m/z calcd for $C_{13}H_{13}ClN_2O_3$ (M)+ 280.0615, found 280.0627. Anal. ($C_{13}H_{13}ClN_2O_3$) C, H, N.

Step 2: 2-[(3,5-Dimethoxybenzyl)oxy]-6-(1-piperazinyl)pyrazine, Maleate

The title compound was prepared according to the procedure of example 50, step 2, starting from the product obtained in step 1 above (1.26 g, 4.50 mmol), piperazine (1.12 g, 13.0 mmol) and $K_2CO_3$ (0.62 g, 4.5 mmol). The free base (1.14 g) of the title compound was converted into its maleate salt. Recrystallization from MeOH-ether furnished 1.05 g (68%) of the title compound: mp 134–137° C. HRMS m/z calcd for $C_{17}H_{22}N_4O_3$ (M)+ 330.1692, found 330.1699. Anal. ($C_{17}H_{22}N_4O_3 \cdot C_4H_4O_4$) C, H, N.

Example 69

2-[2-(4-Methoxyphenyl)ethoxy]-6-(1-piperazinyl)pyrazine, Maleate

Step 1: 2-Chloro-6-[2-(4-methoxyphenyl)ethoxy]pyrazine

The title compound was prepared according to the procedure of example 50, step 1, starting from 4-methoxyphenethyl alcohol (1.99 g, 13.1 mmol), K-t-BuO (1.34 g, 12.0 mmol) and 2,6-dichloropyrazine (1.56 g, 10.5 mmol). The yield of the title compound was 2.14 g (77%) and was obtained as a white solid. Anal. ($C_{13}H_{13}ClN_2O_2$) C, H, N.

Step 2: 2-[2-(4-Methoxyphenyl)ethoxy]-6-(1-piperazinyl)pyrazine, Maleate

The title compound was prepared according to the procedure of example 50, step 2, starting from the product obtained in step 1 above (1.31 g, 4.95 mmol), piperazine (1.24 g, 14.4 mmol) and $K_2CO_3$ (0.68 g, 4.9 mmol). The free base (1.29 g) of the title compound was converted into its maleate salt. Recrystallization from MeOH-ether furnished 1.41 g (79%) of the title compound: mp 149–151° C. HRMS m/z calcd for $C_{17}H_{22}N_4O_2$ (M)+ 314.1743, found 314.1727. Anal. ($C_{17}H_{22}N_4O_2 \cdot C_4H_4O_4$) C, H, N.

Example 70

2-[2-(4-Methyl-1,3-thiazol-5-yl)ethoxy]-6-(1-piperazinyl)pyrazine, Acetate

The title compound was prepared according to the procedure of example 42 starting from 4-methyl-5-hydroxyethyl thiazole (0.215 g, 1.50 mmol) and was isolated as a brown oil. Yield: 0.41 g (66%). HRMS m/z calcd for $C_{14}H_{19}N_5OS$ (M)+ 305.1310, found 300.1325. Anal. ($C_{14}H_{19}N_5OS \cdot 1.5CH_3COOH \cdot 0.7H_2O$).

General Procedure for Synthesis of the Title Compounds Described in Examples 71–96.

To the appropriate alcohol or thiol (1.8 mmol) in dry DMF (5 mL) was added Na-t-BuO (1.20 ml, 2.5 M in DMF) and the mixture was stirred at room temperature for 15 minutes. To the mixture was added a solution of the appropriate piperazino-substituted chloro heterocycle (0.625 mL, 2.0 M in DMF) and the mixture were stirred at 100° C. for 5 h. The reactions were quenched with water (0.2 mL) and the solvent was removed under reduced pressure. The residue was taken up in water/CHCl₃ (20:80; 5 mL) and applied onto

Example 71

2-[2-(3-Methoxyphenoxy)ethoxy]-6-(1-piperazinyl) pyrazine, Acetic acid salt

Starting materials, 2-chloro-6-(1-piperazinyl)pyrazine*, and 2-(3-methoxyphenoxy)-ethanol. Purity 90% (HPLC). Fragmenting mass analysis supports the stated structure. HRMS m/z calcd for $C_{17}H_{22}N_4O_3$ (M)$^+$ 330.1692, found 330.1681.

*Obtained in Example 13, step 2.

Example 72

2-[2-(2,6-Difluorophenoxy)ethoxy]-6-(1-piperazinyl)pyrazine, Acetic acid salt

Starting materials, 2-chloro-6-(1-piperazinyl)pyrazine and 2-(2,6-difluorophenoxy)-ethanol. Fragmenting mass analysis supports the stated structure. Purity 90% (HPLC). HRMS m/z calcd for $C_{16}H_{18}F_2N_4O_3$ (M)$^+$ 336.1398, found 336.1403.

Example 73

2-[2-(Quinolin-8-yloxy)ethoxy]-6-(1-piperazinyl) pyrazine, Acetic acid salt

Starting materials, 2-chloro-6-(1-piperazinyl)pyrazine and 2-(quinolin-8-yloxy)ethanol.* Fragmenting mass analysis supports the stated structure. Purity 90% (HPLC). HRMS m/z calcd for $C_{19}H_{21}N_5O_2$ (M)$^+$ 351.1695, found 351.1683.

*Described in WO 00/76984.

Example 74

2-[(2R)-2,3-Dihydro-1,4-benzodioxin-2-ylmethoxy]-6-(1-piperazinyl)pyrazine, Acetic acid salt Starting materials, 2-chloro-6-(1-piperazinyl)pyrazine and (2R)-2-hydroxymethyl-1,4-benzodioxan*. Fragmenting mass analysis supports the stated structure. Purity 90% (HPLC). HRMS m/z calcd for $C_{17}H_{20}N_4O_3$ (M)$^+$ 328.1535, found 328.1524.

*Described in Tetrahedron Lett. 1988, 29, 3671–4.

Example 75

2-[2-(2-Naphthyloxy)ethoxy]-6-(1-piperazinyl) pyrazine, Acetic acid salt

Starting materials, 2-chloro-6-(1-piperazinyl)pyrazine and 2-(naphthalen-2-yloxy)-ethanol. Fragmenting mass analysis supports the stated structure. Purity 90% (HPLC). HRMS m/z calcd for $C_{20}H_{22}N_4O_2$ (M)$^+$ 350.1743, found 350.1752

Example 76

2-{2-[(2-Ethoxy-3-pyridinyl)oxy]ethoxy}-6-(1-piperazinyl)pyrazine, Acetic acid salt Starting materials, 2-chloro-6-(1-piperazinyl)pyrazine and 2-(2-ethoxypyridin-3-yloxy)-ethanol*. Fragmenting mass analysis supports the stated structure. Purity 80% (HPLC). HRMS m/z calcd for $C_{17}H_{23}N_5O_3$ (M)$^+$ 345.1801, found 345.1793.

*Described in WO 00/76984.

Example 77

2-{[4-(Benzyloxy)-3-methoxybenzyl]oxy}-6-(1-piperazinyl)pyrazine, Acetic acid salt Starting materials, 2-chloro-6-(1-piperazinyl)pyrazine and (4-benzyloxy-3-methoxyphenyl)-methanol. Fragmenting mass analysis supports the stated structure. Purity 90% (HPLC). HRMS m/z calcd for $C_{23}H_{26}N_4O_3$ (M)$^+$ 406.2005, found 406.1967.

Example 78

2-{[5-(Phenylethynyl)-2-thienyl]methoxy}-6-(1-piperazinyl)pyrazine, Acetic acid salt Starting materials, 2-chloro-6-(1-piperazinyl)pyrazine and (5-phenylethynyl-thiophen-2-yl)-methanol. Fragmenting mass analysis supports the stated structure Purity 80% (HPLC). HRMS m/z calcd for $C_{21}H_{20}N_4OS$ (M)$^+$ 376.1358, found 376.1346.

Example 79

2-(2,3-Dihydro-1,4-benzodioxin-6-ylmethoxy)-6-(1-piperazinyl)pyrazine, Acetic acid salt Starting materials, 2-chloro-6-(1-piperazinyl)pyrazine and (2,3-dihydro-1,4-benzodioxin-6-yl)-methanol. Fragmenting mass analysis supports the stated structure. Purity 90% (HPLC). HRMS m/z calcd for $C_{17}H_{20}N_4O_3$ (M)$^+$ 328.1535, found 328.1543.

Example 80

2-(1-Methyl-2-phenylethoxy)-6-(1-piperazinyl) pyrazine, Acetic acid salt

The general procedure was followed with the exception that the reaction mixture was heated at 100° C. overnight. Starting materials, 2-chloro-6-(1-piperazinyl)pyrazine and 1-phenylpropan-2-ol. Fragmenting mass analysis supports the stated structure. Purity 70% (HPLC). HRMS m/z calcd for $C_{17}H_{22}N_4O$ (M)$^+$ 298.1794, found 298.1801.

Example 81

2-[(2-Chlorobenzyl)sulfanyl]-6-(1-piperazinyl) pyrazine, Acetic acid salt

Starting materials, 2-chloro-6-(1-piperazinyl)pyrazine and (2-chlorophenyl)-methanethiol. Fragmenting mass analysis supports the stated structure. Purity 90% (HPLC). HRMS m/z calcd for $C_{15}H_{17}ClN_4S$ (M)$^+$ 320.0862, found 320.0868

Example 82

2-[(2-Phenylethyl)sulfanyl]-6-(1-piperazinyl) pyrazine, Acetic acid salt

Starting materials, 2-chloro-6-(1-piperazinyl)pyrazine and 2-phenyl-ethanethiol. Fragmenting mass analysis supports the stated structure. Purity 90% (HPLC). HRMS m/z calcd for $C_{16}H_{20}N_4S$ (M)$^+$ 300.1409, found 300.1419.

Example 83

2-[(4-Phenoxybenzyl)oxy]-6-(1-piperazinyl) pyrazine, Acetic acid salt

Starting materials 2-chloro-6-(1-piperazinyl)pyrazine and 4-phenoxybenzyl alcohol*. Fragmenting mass analysis supports the stated structure. Purity 90% (HPLC). HRMS m/z calcd for $C_{21}H_{22}N_4O_2$ (M)$^+$ 362.1743, found 362.1738.

*Prepared by reduction of 4-phenoxybenzaldehyde.

Example 84

2-{[4-(3-Dimethylamino-propoxy)benzyl]oxy}-6-(1-piperazinyl)pyrazine, Acetic acid salt Starting materials, 2-chloro-6-(1-piperazinyl)pyrazine and [4-(3-dimethylamino-propoxy) -phenyl]-methanol. Fragmenting mass analysis supports the stated structure. Purity 90% (HPLC). HRMS m/z calcd for $C_{20}H_{29}N_5O_2$ (M)$^+$ 371.2321, found 371.2314.

Example 85

2-{2-[2-(Benzyloxy)phenyl]ethoxy}-6-(1-piperazinyl)pyrazine, Acetic acid salt

Starting materials, 2-chloro-6-(1-piperazinyl)pyrazine and 2-(2-benzyloxy-phenyl)-ethanol.* Fragmenting mass analysis supports the stated structure. Purity 70% (HPLC). HRMS m/z calcd for $C_{23}H_{26}N_4O_2$ (M)$^+$ 390.2056, found 390.2043.

*Prepared by reduction of (2-benzyloxy-phenyl)-acetic acid.

Example 86

2-[2-(2,5-Dimethoxyphenyl)ethoxy]-6-(1-piperazinyl)pyrazine, Acetic acid salt

Starting materials, 2-chloro-6-(1-piperazinyl)pyrazine and 2-(2,5-dimethoxy-phenyl)-ethanol*. Fragmenting mass analysis supports the stated structure. Purity 80% (HPLC). HRMS m/z calcd for $C_{18}H_{24}N_4O_3$ (M)$^+$ 344.1848, found 344.1861.

*Prepared by reduction of (2,5-dimethoxy-phenyl)-acetic acid.

Example 87

2-(1-Benzofuran-2-ylmethoxy)-6-(1-piperazinyl) pyrazine, Acetic acid salt

Starting materials, 2-chloro-6-(1-piperazinyl)pyrazine and benzofuran-2-yl-methanol.* Fragmenting mass analysis supports the stated structure. Purity 80% (HPLC). HRMS m/z calcd for $C_{17}H_{18}N_4O_2$ (M)$^+$ 310.1430, found 310.1419.

*Prepared by reduction of benzofuran-2-carbaldehyde.

Example 88

2-{-[3-Methoxy-2-(phenoxymethyl)phenyl]ethoxy}-6-(1-piperazinyl)pyrazine, Acetic acid salt Starting materials, 2-chloro-6-(1-piperazinyl)pyrazine and (3-methoxy-2-phenoxymethyl-phenyl)-methanol.* Fragmenting mass analysis supports the stated structure. Purity 90% (HPLC). HRMS m/z calcd for $C_{23}H_{26}N_4O_3$ (M)$^+$ 406.2005, found 406.2011.

*Prepared by reduction of 3-methoxy-2-phenoxymethyl-benzaldehyde.

Example 89

2-[2-(Isoquinolin-7-yloxy)ethoxy]-6-(1-piperazinyl) pyrazine, Acetic acid salt

Step 1: 2-(7-Isoquinolinyloxy)ethanol

A mixture of 7-hydroxyisoquinoline (1.15 g, 7.9 mmol), ethylene carbonate (0.98 g, 11.1 mmol), powdered $K_2CO_3$ (0.65 g, 4.7 mmol) in dry DMF (20 mL) was stirred at 145° C. for two hours. The reaction was quenched with MeOH (1 mL), filtered and the solvent was removed under reduced pressure. The residue was taken up between alkaline water ($K_2CO_3$) and $CHCl_3$. Concentration of the dried ($MgSO_4$) organic phase afforded 1.4 g (94%) of the title compound as a yellow oil that solidified upon standing. Purity 91% (HPLC). Fragmenting mass analysis supports the stated structure.

Step 2: 2-[2-(Isoquinolin-7-yloxy)ethoxy]-6-(1-piperazinyl)pyrazine, Acetic acid salt The general procedure was followed starting 2-chloro-6-(1-piperazinyl)pyrazine and 2-(7-isoquinolinyloxy)ethanol. Fragmenting mass analysis supports the stated structure. Purity 80% (HPLC). HRMS m/z calcd for $C_{19}H_{21}N_5O_2$ (M)$^+$ 351.1695, found 351.1696.

Example 90

2-(2,3-Dihydro-1H-inden-2-yloxy)-6-(1-piperazinyl) pyrazine, Acetic acid salt

Starting materials, 2-chloro-6-(1-piperazinyl)pyrazine and 2-indanol. The general procedure was followed with the exception that the reaction mixture was heated at 100° C. overnight. Fragmenting mass analysis supports the stated structure. Purity 90% (HPLC). HRMS m/z calcd for $C_{17}H_{20}N_4O$ (M)$^+$ 296.1637, found 296.1652.

Example 91

2-{[2-(Phenoxymethyl)benzyl]oxy}-6-(1-piperazinyl)pyrazine, Acetic acid salt

Starting materials, 2-chloro-6-(1-piperazinyl)pyrazine and $^2$-phenoxymethyl-benzyl alcohol.* Fragmenting mass analysis supports the stated structure. Purity 90% (HPLC). HRMS m/z calcd for $C_{22}H_{24}N_4O_2$ (M)$^+$ 376.1899, found 376.1889.

*Prepared by reduction of 2-phenoxymethylbenzoic acid by lithium aluminum hydride in THF, cf J. Chem. Soc. 1954, 2819.

Example 92

2-2-Cyclohexylethoxy)-6-(1-piperazinyl)pyrazine, Acetic acid salt

Starting materials, 2-chloro-6-(1-piperazinyl)pyrazine and 2-cyclohexyl-ethanol. Fragmenting mass analysis supports the stated structure. Purity 90% (HPLC). HRMS m/z calcd for $C_{16}H_{26}N_4O$ (M)$^+$ 290.2107, found 290.2109.

Example 93

2-[2-(2-Amino-quinolin-8-yloxy)ethoxy]-6-(-piperazinyl)pyrazine, Acetic acid salt Starting materials, 2-chloro-6-(1-piperazinyl)pyrazine and 2-(2-amino-quinolin-8-yloxy)-ethanol.* Fragmenting mass analysis supports the stated structure. Purity 90% (HPLC). HRMS m/z calcd for $C_{19}H_{22}N_6O_2$ (M)$^+$ 366.1804, found 366.1791.

*Prepared as described in WO 00/76984.

Example 94

2-[(3-Cyanobenzyl)oxy]-6-(1-piperazinyl)pyrazine

Starting materials, 2-chloro-6-(1-piperazinyl)pyrazine and 3-cyanobenzyl alcohol. Fragmenting mass analysis supports the stated structure. Purity 90% (HPLC). HRMS m/z calcd for $C_{16}H_{17}N_5O$ (M)$^+$ 295.1433, found 295.1431.

Example 95

2-[(5-Fluoro-2-methoxybenzyl)oxy]-6-(1-piperazinyl)pyrazine, Acetic acid salt Starting materials, 2-chloro-6-(1-piperazinyl)pyrazine and (5-fluoro-2-methoxy-phenyl)-methanol.* Fragmenting mass analysis supports the stated structure. Purity 90% (HPLC). HRMS m/z calcd for $C_{16}H_{19}FN_4O_2$ (M)$^+$ 318.1492, found 318.1490.

*Prepared by reduction of 5-fluoro-2-methoxybenzaldehyde.

Example 96

2-(1-Cyclopentylethoxy)-6-(1-piperazinyl)pyrazine, Acetic acid salt

Starting materials, 2-chloro-6-(1-piperazinyl)pyrazine and 1-cyclopentyl-ethanol. The general procedure was followed with the exceptions that dioxane was used as solvent and that the reaction mixture was heated in a sealed tube with microwaves at 160° C. for 20 minutes. Fragmenting mass analysis supports the stated structure. Purity 90% (HPLC). HRMS m/z calcd for $C_{15}H_{24}N_4O$ (M)$^+$ 276.1950, found 276.1955.

Example 97

2-[(2,5-Difluorobenzyl)oxy]-6-(1-piperazinyl)pyrazine, Maleate

The title compound was prepared according to the procedure of example 50, step 2, starting from 2-chloro-6-[(2,5-difluorobenzyl)oxy]pyrazine (3.43 g, 13.4 mmol; obtained according to the procedure of example 50, step 1, starting from 2,5-difluorobenzyl alcohol), piperazine (3.51 g, 40.7 mmol) and $K_2CO_3$ (1.94 g, 14.0 mmol) with the exception that the final filtration through alumina was omitted. The yield of the free base of the title compound was 2.84 g (69%) which was obtained as an oil. The free base was converted into its maleate salt. Purity 100% (HPLC). MS m/z 306 (M)$^+$. HRMS m/z calcd for $C_{15}H_{16}F_2N_4O$ (M)$^+$ 306.1292, found 306.1297.

Example 98

2-[(3-Dimethylaminobenzyl)oxy]-6-(1-piperazinyl)pyrazine

The title compound was prepared according to the procedure of example 50, step 2, starting from 2-chloro-6-[(3-dimethylaminobenzyl)oxy]pyrazine (3.04 g, 11.5 mmol; obtained according to the procedure of example 50, step 1, starting from 3-dimethylaminobenzyl alcohol), piperazine (3.08 g, 35.7 mmol) and $K_2CO_3$ (1.59 g, 11.5 mmol) with the exception that the final filtration through alumina was omitted. The yield of the of the title compound was 2.06 g (57%) which was obtained as a beige colored oil that solidified when refrigerated. Purity 98% (HPLC). MS m/z 313 (M)$^+$. HRMS m/z calcd for $C_{17}H_{23}N_5O$ (M)$^+$ 313.1903, found 313.1910.

Example 99

2-[{4-(2-Pyridinyl)benzyl}oxy]-6-(1-piperazinyl)pyrazine

The title compound was prepared according to the procedure of example 50, step 2, starting from 2-chloro-6-[{4-(2-pyridinyl)benzyl}oxy]pyrazine (2.73 g, 9.16 mmol; obtained according to the procedure of example 50, step 1, starting from 4-(2-pyridinyl)benzyl alcohol*), piperazine (2.41 g, 27.9 mmol) and $K_2CO_3$ (1.33 g, 9.62 mmol) with the exception that the final filtration through alumina was omitted. The yield of the of the title compound was 2.06 g (65%) which was obtained as a beige colored oil that solidified when refrigerated. Purity 100% (HPLC). MS m/z 347 (M)$^+$. HRMS m/z calcd for $C_{20}H_{21}N_5O$ (M)$^+$ 347.1746, found 347.1749.

*Obtained by reduction (NaBH$_4$) of 4-(2-pyridyl)benzaldehyde.

Example 100

2-[(2-Fluorobenzyl)oxy]-6-(1-piperazinyl)pyrazine, Maleate

The title compound was prepared according to the procedure of example 50, step 2, starting from 2-chloro-6-[(2-fluorobenzyl)oxy]pyrazine (3.68 g, 15.4 mmol; obtained according to the procedure of example 50, step 1, starting from 2-fluorobenzyl alcohol), piperazine (4.06 g, 47.1 mmol) and $K_2CO_3$ (2.24 g, 16.2 mmol) with the exception that the final filtration through alumina was omitted. The yield of the free base of the title compound was 3.28 g (74%) which was obtained as an oil. The free base was converted into its maleate salt. Purity 100% (HPLC). MS m/z 288 (M)$^+$. HRMS m/z calcd for $C_{15}H_{17}FN_4O$ (M)$^+$ 288.1386, found 288.1378.

Example 101

2-(Benzo[b]thiophen-3-ylmethoxy)-6-(1-piperazinyl)pyrazine, Maleate

The title compound was prepared according to the procedure of example 50, step 2, starting from 2-chloro-6-(benzo[b]thiophen-3-ylmethoxy)pyrazine (2.88 g, 10.4 mmol; obtained according to the procedure of example 50, step 1, starting from benzo[b]thiophene-3-methanol), piperazine (2.73 g, 31.7 mmol) and $K_2CO_3$ (1.51 g, 10.9 mmol) with the exception that the final filtration through alumina was omitted. The yield of the free base of the title compound was 2.34 g (69%) which was obtained as a beige colored oil. The free base was converted into its maleate salt. Purity 99% (HPLC). MS m/z 326 (M)$^+$. HRMS m/z calcd for $C_{17}H_{18}N_4OS$ (M)$^+$ 326.1201, found 326.1207.

Example 102

2-(3-Phenoxy-thiophen-2-ylmethoxy)-6-(1-piperazinyl)pyrazine, Maleate

The title compound was prepared according to the procedure of example 50, step 2, starting from 2-chloro-6-(3-phenoxy-thiophen-2-ylmethoxy)pyrazine [2.83 g, 8.88 mmol; obtained according to the procedure of example 50, step 1, starting from (3-phenoxy-2-thienyl)methanol], piperazine (2.33 g, 27.1 mmol) and $K_2CO_3$ (1.29 g, 9.3 mmol) with the exception that the final filtration through alumina was omitted. The yield of the free base of the title compound was 1.80 g (55%) which was obtained as a beige colored oil. The free base was converted into its maleate salt. Purity 98% (HPLC). MS m/z 368 (M)$^+$. HRMS m/z calcd for $C_{19}H_{20}N_4O_2S$ (M)$^+$ 368.1307, found 368.1306.

Example 103

2-[5-(2-Pyridinyl)-thiophen-2-ylmethoxy)]-6-(1-piperazinyl)pyrazine, Maleate The title compound was prepared according to the procedure of example 50, step 2, starting from 2-chloro-6-[5-

(2-pyridinyl)-thiophen-2-ylmethoxy)]pyrazine [2.17 g, 7.13 mmol; obtained according to the procedure of example 50, step 1, starting from 5-(pyridin-2-yl)thiophene-2-methanol], piperazine (1.84 g, 21.4 mmol) and $K_2CO_3$ (0.99 g, 7.1 mmol) with the exception that the final filtration through alumina was omitted. The yield of the free base of the title compound was 1.66 g (66%) which was obtained as a beige colored oil. The free base was converted into its maleate salt. Purity 100% (HPLC). MS m/z 353 (M)$^+$. HRMS m/z calcd for $C_{18}H_{19}N_5OS$ (M)$^+$ 353.1310, found 353.1307.

Example 104

2-[2-(5-Methyl-2-phenyl-oxazol-4-yl)-ethoxy]-6-(1-piperazinyl)pyrazine

The title compound was prepared according to the procedure of example 50, step 2, starting from 2-chloro-6-[2-(5-methyl-2-phenyl-oxazol-4-yl)-ethoxy]pyrazine [2.90 g, 9.18 mmol; obtained according to the procedure of example 50, step 1, starting from 2-(5-methyl-2-phenyloxazol-4-yl) ethanol], piperazine (2.37 g, 27.5 mmol) and $K_2CO_3$ (1.27 g, 9.19 mmol) with the exception that the final filtration through alumina was omitted. The yield of the of the title compound was 2.09 g (62%) which was obtained as a light yellow oil that solidified when refrigerated. Purity 100% (HPLC). MS m/z 365 (M)$^+$. HRMS m/z calcd for $C_{20}H_{23}N_5O_2$ (M)$^+$ 365.1852, found 365.1855.

Example 105

2-[1-(2,6-Difluoro-phenyl)-ethoxy]-6-(1-piperazinyl) pyrazine, Maleate

The title compound was prepared according to the procedure of example 50, step 2, starting from 2-chloro-6-[1-(2,6-difluoro-phenyl)-ethoxy]pyrazine (3.20 g, 11.8 mmol; obtained according to the procedure of example 50, step 1, starting from 2,6-difluoro-α-methylbenzyl alcohol), piperazine (3.05 g, 35.4 mmol) and $K_2CO_3$ (1.63 g, 11.8 mmol) with the exception that the final filtration through alumina was omitted. The yield of the free base of the title compound was 2.95 g (78%) which was obtained as a colorless oil. The free base was converted into its maleate salt. Purity 100% (HPLC). MS m/z 320 (M)$^+$. HRMS m/z calcd for $C_{16}H_{18}F_2N_4O$ (M)$^+$ 320.1449, found 320.1447.

Example 106

2-(2-Naphthalen-2-yl-ethoxy)-6-(1-piperazinyl) pyrazine, Maleate

The title compound was prepared according to the procedure of example 50, step 2, starting from 2-chloro-6-(2-naphthalen-2-yl-ethoxy)pyrazine (2.73 g, 9.60 mmol; obtained according to the procedure of example 50, step 1, starting from 2-naphthalene-ethanol), piperazine (2.89 g, 33.5 mmol) and $K_2CO_3$ (1.39 g, 10.1 mmol) with the exception that the final filtration through alumina was omitted. The yield of the free base of the title compound was 2.63 g (82%) which was obtained as a colorless oil. The free base was converted into its maleate salt. Purity 99% (HPLC). MS m/z 334 (M)$^+$. HRMS m/z calcd for $C_{20}H_{22}N_4O$ (M)$^+$ 334.1794, found 334.1794.

Example 107

2-[3-(Naphthalen-2-yloxy)-propoxy]-6-(1-piperazinyl)pyrazine, Maleate

The title compound was prepared according to the procedure of example 50, step 2, starting from 2-chloro-6-[3-(naphthalen-2-yloxy)-propoxy]pyrazine [2.24 g, 7.12 mmol; obtained according to the procedure of example 50, step 1, starting from 3-(naphthalen-2-yloxy)-propan-1-ol*], piperazine (1.90 g, 22.1 mmol) and $K_2CO_3$ (1.03 g, 7.45 mmol) with the exception that the final filtration through alumina was omitted. The yield of the free base of the title compound was 1.10 g (42%) which was obtained as a light beige colored oil. The free base was converted into its maleate salt. Purity 100% (HPLC). MS m/z 364 (M)$^+$. HRMS m/z calcd for $C_{21}H_{24}N_4O_2$ (M)$^+$ 364.1899, found 364.1895.

*Described in J. Am. Chem Soc. 1929, 51, 3417 and ibid. 1954, 76, 56.

Example 108

2-(4-Phenylethynyl-thiophen-2-ylmethoxy)-6-(1-piperazinyl)pyrazine, Maleate The title compound was prepared according to the procedure of example 50, step 2, starting from 2-chloro-6-(4-phenylethynyl-thiophen-2-ylmethoxy)pyrazine [2.05 g, 6.28 mmol; obtained according to the procedure of example 50, step 1, starting from 4-(phenylethynyl)thiophene-2-methanol*], piperazine (1.62 g, 18.8 mmol) and $K_2CO_3$ (0.89 g, 6.4 mmol) with the exception that the final filtration through alumina was omitted. The yield of the free base of the title compound was 1.80 g (76%) which was obtained as a light beige colored oil. The free base was converted into its maleate salt. Purity 100% (HPLC). MS m/z 376 (M)$^+$. HRMS m/z calcd for $C_{21}H_{20}N_4OS$ (M)$^+$ 376.1358, found 376.1351.

*Obtained by reduction (NaBH$_4$) of 4-(phenylethynyl)thiophene-2-carboxaldehyde.

Example 109

2-(1-Cyclopropyl-ethoxy)-6-(1-piperazinyl)pyrazine, Maleate

The title compound was prepared according to the procedure of example 50, step 2, starting from 2-chloro-6-(1-cyclopropyl-ethoxy)pyrazine (2.38 g, 12.0 mmol; obtained according to the procedure of example 50, step 1, starting from α-methylcyclopropanemethanol), piperazine (3.60 g, 41.8 mmol) and $K_2CO_3$ (1.75 g, 12.7 mmol) with the exception that the final filtration through alumina was omitted. The yield of the free base of the title compound was 2.05 g (69%) which was obtained as a colorless oil. The free base was converted into its maleate salt. Purity 100% (HPLC). MS m/z 248 (M)$^+$. HRMS m/z calcd for $C_{13}H_{20}N_4O$ (M)$^+$ 248.1637, found 248.1636.

Example 110

2-[2-(6-Methoxy-naphthalen-2-yloxy)-ethoxy]-6-(1-piperazinyl)pyrazine

The title compound was prepared according to the procedure of example 50, step 2, starting from 2-chloro-6-[2-(6-methoxy-naphthalen-2-yloxy)-ethoxy]pyrazine [0.94 g, 2.8 mmol; obtained according to the procedure of example 50, step 1, starting from 2-(6-methoxy-naphthalen-2-yloxy) ethanol*], piperazine (1.00 g, 11.6 mmol) and $K_2CO_3$ (0.50 g, 3.6 mmol) with the exception that the final filtration through alumina was omitted. The yield of the of the title compound was 0.52 g (48%) which was obtained as a beige colored solid. Purity 100% (HPLC). MS m/z 380 (M)$^+$. HRMS m/z calcd for $C_{21}H_{24}N_4O_3$ (M)$^+$ 380.1848, found 380.1845.

*Prepared from 6-methoxy-2-naphthol and ethylene carbonat according to the procedure of Example 134, step 1, in WO 00/76984. The reaction mixture was refluxed for 2 h. Pure 2-(6-methoxy-naphthalen-2-yloxy)ethanol was obtained by recrystallization from MeOH/CHCl$_3$/n-hexane.

Example 111

2-[2-(7-Methoxy-naphthalen-2-yloxy)-ethoxy]-6-(1-piperazinyl)pyrazine

The title compound was prepared according to the procedure of example 50, step 2, starting from 2-chloro-6-[2-(7-methoxy-naphthalen-2-yloxy)-ethoxy]pyrazine [1.19 g, 3.60 mmol; obtained according to the procedure of example 50, step 1, starting from 2-(7-methoxy-naphthalen-2-yloxy)ethanol*], piperazine (1.25 g, 14.5 mmol) and $K_2CO_3$ (0.60 g, 4.3 mmol) with the exception that the final filtration through alumina was omitted. The yield of the of the title compound was 0.98 g (71%) which was obtained as an oil that solidified when refrigerated. Purity 100% (HPLC). MS m/z 380 (M)$^+$. HRMS m/z calcd for $C_{21}H_{24}N_4O_3$ (M)$^+$ 380.1848, found 380.1851.

*Prepared from 7-methoxy-2-naphthol and ethylene carbonat according to the procedure of Example 134, step 1, in WO 00/76984. The reaction mixture was refluxed for 2 h. Pure 2-(7-methoxy-naphthalen-2-yloxy)ethanol was obtained after column chromatography on silica gel using n-hexane/ethyl acetate (6:4) as eluent.

Example 112

2-[5-(4-Chlorophenyl)-2-methylfuran-3-ylmethoxy]-6-(1-piperazinyl)pyrazine

The title compound was prepared according to the procedure of example 50, step 2, starting from 2-chloro-6-[5-(4-chlorophenyl)-2-methylfuran-3-ylmethoxy]pyrazine [3.14 g, 9.39 mmol; obtained according to the procedure of example 50, step 1, starting from 5-(4-chlorophenyl)-3-hydroxymethyl-2-methylfuran], piperazine (2.47 g, 28.6 mmol) and $K_2CO_3$ (1.36 g, 9.86 mmol) with the exception that the final filtration through alumina was omitted. The yield of the of the title compound was 2.11 g (58%) which was obtained as a beige colored solid. Purity 100% (HPLC). MS m/z 384 (M)$^+$. HRMS m/z calcd for $C_{20}H_{21}ClN_4O_2$ (M)$^+$ 384.1353, found 384.1357.

Example 113

2-(1H-Indol-4-ylmethoxy)-6-(1-piperazinyl) pyrazine, Maleate

The title compound was prepared according to the procedure of example 50, step 2, starting from 2-chloro-6-(1H-indol-4-ylmethoxy)pyrazine [0.486 g, 1.87 mmol; obtained according to the procedure of example 50, step 1, starting from (1H-indol-4-yl)-methanol*], piperazine (0.491 g, 5.71 mmol) and $K_2CO_3$ (0.272 g, 1.96 mmol) with the exception that the final filtration through alumina was omitted. The yield of the free base of the title compound was 0.198 g (34%) which was obtained as an oil. The free base was converted into its maleate salt. Purity 100% (HPLC). MS m/z 309 (M)$^+$. HRMS m/z calcd for $C_{17}H_{19}N_5O$ (M)$^+$ 309.1590, found 309.1582.

*The reaction was carried out using (1H-indol-4-yl)-methanol (0.712 g, 4.84 mmol), K-t-BuO (0.517 g, 4.61 mmol), and 2,6-dichloropyrazine (0.687 g, 4.61 mmol).

Example 114

2-(2-Phenyl-propoxy)-6-(1-piperazinyl)pyrazine, Maleate

The title compound was prepared according to the procedure of example 50, step 2, starting from 2-chloro-6-(2-phenyl-propoxy)pyrazine (2.39 g, 9.61 mmol; obtained according to the procedure of example 50, step 1, starting from 2-phenyl-1-propanol), piperazine (2.90 g, 3.36 mmol) and $K_2CO_3$ (1.40 g, 10.1 mmol) with the exception that the final filtration through alumina was omitted. The yield of the free base of the title compound was 1.66 g (58%) which was obtained as a colorless oil. The free base was converted into its maleate salt. Purity 99% (HPLC). HRMS m/z calcd for $C_{17}H_{22}N_4O$ (M)$^+$ 298.1794, found 298.1795.

Example 115

2-[2-(2-Methoxyphenyl)ethoxy]-6-(1-piperazinyl) pyrazine, Maleate

The title compound was prepared according to the procedure of example 50, step 2, starting from 2-chloro-6-[2-(2-methoxyphenyl)ethoxy]pyrazine (0.967 g, 3.65 mmol; obtained according to the procedure of example 50, step 1, starting from 2-methoxyphenethyl alcohol), piperazine (0.913 g, 10.6 mmol) and $K_2CO_3$ (0.505 g, 3.65 mmol). The yield of the free base of the title compound was 0.63 g (55%) which was obtained as a colorless oil. The free base was converted into its maleate salt. Purity 100% (HPLC). MS m/z 314 (M)$^+$. HRMS m/z calcd for $C_{17}H_{22}N_4O_2$ (M)$^+$ 314.1743, found 314.1750.

Example 116

2-[2-(3-Methoxyphenyl)ethoxy]-6-(1-piperazinyl) pyrazine

The title compound was prepared according to the procedure of example 50, step 2, starting from 2-chloro-6-[2-(3-methoxyphenyl)ethoxy]pyrazine (1.12 g, 4.23 mmol; obtained according to the procedure of example 50, step 1, starting from 3-methoxyphenethyl alcohol), piperazine (1.06 g, 12.3 mmol) and $K_2CO_3$ (0.585 g, 4.23 mmol). The yield of the title compound was 0.91 g (69%) which was obtained as light beige oil. HRMS m/z calcd for $C_{17}H_{22}N_4O_2$ (M)$^+$ 314.1743, found 314.1759. Anal. ($C_{17}H_{22}N_4O_2$) C, H, N.

Example 117

2-[(2-Phenoxybenzyl)oxy]-6-(1-piperazinyl) pyrazine, Maleate

The title compound was prepared according to the procedure of example 50, step 2, starting from 2-chloro-6-[(2-phenoxybenzyl)oxy]pyrazine (0.981 g, 3.14 mmol; obtained according to the procedure of example 50, step 1, starting from 2-phenoxybenzyl alcohol), piperazine (0.784 g, 9.10 mmol) and $K_2CO_3$ (0.434 g, 3.14 mmol) with the exception that the final filtration through alumina was omitted. The yield of the free base of the title compound was 0.80 g (70%) which was obtained as a colorless oil. The free base was converted into its maleate salt. Anal. ($C_{21}H_{22}N_4O_2 \cdot C_4H_4O_4$) C, H, N.

Example 118

2-Benzylamino-4-(1-piperazinyl)pyrimidine, Hydrochloride

Step 1: 2-Benzylamino-4-[1-(4-tert-butoxycarbonyl) piperazinyl]pyrimidine

A mixture of 2-chloro-4-[1-(4-tert-butoxycarbonyl) piperazinyl]pyrimidine (obtained in Example 33, step 1; 1.80 g, 6.02 mmol), benzylamine (10 mL, large excess) and potassium carbonate (0.91 g, 6.62 mmol) was stirred in 50 mL of propionitrile at 110° C. for 1.5 h. The mixture was poured into water (200 mL) and left over night. The title compound was collected, washed with water +10% methanol and dried. Yield: 2.08 g (94%). Purity >90% (HPLC). HRMS m/z calcd for $C_{20}H_{27}N_5O_2$ $(M)^+$ 369.2165, found 369.2152.

Step 2: 2-Benzylamino-4-(1-piperazinyl)pyrimidine, Hydrochloride

To a solution of 2-benzylamino-4-[1-(4-tert-butoxycarbonyl)piperazinyl]pyrimidine (37 mg, 0.10 mmol) in a mixture of methyl tert butyl ether (3 mL) and methanol (1 mL) was 4.0 M HCl in dioxane (1 mL) added. The reaction was shaken over night. Methyl tert butyl ether (2 mL) was added. The title compound was collected as a white solid. Yield: 29 mg (95%). Purity >90% (HPLC). MS m/z 270 $(M+H)^+$.

Example 119

(2R)-1-[6-{(2-Chlorobenzyl)sulfanyl}-2-pyrazinyl]-2-methylpiperazine, Hydrochloride Na-t-BuO (8.7 mmol 0.84 g) was added to a solution of 2-chlorobenzylthiol (5.7 mmol 0.90 g) in dry DMF (25 mL) and the mixture was stirred at room temperature for 10 minutes. (2R)-1-(6-chloro-2-pyrazinyl)-2-methylpiperazine (0.92 g, 4.35 mmol; obtained in Example 62, step 2) was added and the reaction was stirred at 70° C. for 2 h. The mixture was filtered through a plug of silica and the solvent from the filtrate was evaporated at reduced pressure. The brown residue was chromatographed over silica gel using $CHCl_3$/MeOH/aq $NH_3$ 90/10/0.25 as eluent. This furnished the free base of the title compound as a yellow oil. The free base was precipitated as its HCl salt with HCl/ether to give 1.10 g (68%) of the title compound as light yellow crystals. Purity 98% (HPLC). HRMS m/z for $C_{16}H_{19}ClN_4S$ $(M)^+$ calcd for 334.1019, found 334.1036.

Example 120

2-(3-Thienylmethoxy)-6-(1-piperazinyl)pyrazine

The title compound was prepared according to the procedure of Example 20 starting from 3-thiophenemethanol (6.05 g, 53.0 mmol), K-t-BuO (0.897 g, 7.99 mmol) and 6-chloro-2-(1-piperazinyl)pyrazine (0.845 g, 4.25 mmol: obtained in Example 13, step 2). The reaction mixture was stirred at 105° C. for 7.5 h. Following chromatography on silica, solvents were evaporated off. The remaining oil was redissolved in ethyl acetetate and filtered through a short plug of alumina (5×3 cm) using ether/MeOH (96:4) as eluent. Solvent removal in vacuo gave 0.76 g (64%) of the title compound as a colorless oil. HRMS m/z for $C_{13}H_{16}N_4OS$ $(M)^+$ calcd for 276.1045, found 276.1037. Anal. ($C_{13}H_{16}N_4OS.0.25\ H_2O$) C, H, N.

Example 121

2-(3-Phenoxypropoxy)-6-(1-piperazinyl)pyrazine, Maleate

The title compound was prepared according to the procedure of example 50, step 2, starting from 2-chloro-6-(3-phenoxypropoxy)pyrazine (1.04 g, 3.93 mmol; obtained according to the procedure of example 50, step 1, starting from 3-phenoxy-1-propanol), piperazine (0.981 g, 11.4 mmol) and $K_2CO_3$ (0.543 g, 3.93 mmol). Following chromatography on silica, solvents were evaporated off. The semi-solid residue (0.83 g) was redissolved in $CHCl_3$ and filtered. The clear solution was concentrated in vacuo and the resulting free base of the title compound was converted into its maleate salt. Yield: 0.90 g (53%). HRMS m/z calcd for $C_{17}H_{22}N_4O_2$ $(M)^+$ 314.1743, found 314.1728. Anal. ($C_{17}H_{22}N_4O_2.C_4H_4O_4$) C, H, N.

Example 122

2-{[4-(Benzyloxy)benzyl]oxy}-6-(1-piperazinyl)pyrazine

The title compound was prepared according to the procedure of example 50, step 2, starting from 2-chloro-6-{[4-(benzyloxy)benzyl]oxy}pyrazine (1.15 g, 3.52 mmol; obtained according to the procedure of example 50, step 1, starting from 4-benzyloxybenzyl alcohol), piperazine (0.894 g, 10.4 mmol) and $K_2CO_3$ (0.486 g, 3.52 mmol). The yield of the title compound was 0.57 g (43%) which was obtained as a colorless viscous oil that solidified upon standing. Fragmenting mass analysis supports the stated structure. HRMS m/z calcd for $C_{22}H_{24}N_4O_2$ $(M)^+$ 376.1899, found 376.1892.

Example 123

2-(N-Hexyloxy)-6-(1-piperazinyl)pyrazine

The title compound was prepared according to the procedure of example 50, step 2, starting from 2-chloro-6-(n-hexyloxy)pyrazine (1.54 g, 7.17 mmol; obtained according to the procedure of example 50, step 1, starting from n-hexanol), piperazine (1.90 g, 22.1 mmol) and $K_2CO_3$ (0.99 g, 7.16 mmol). The yield of the title compound was 1.21 g (64%) which was obtained as a colorless oil. HRMS m/z calcd for $C_{14}H_{24}N_4O$ $(M)^+$ 264.1950, found 264.1953. Anal. ($C_{14}H_{24}N_4O$) C, H, N.

EXAMPLE 124

2-(Propargyloxy)-6-(1-piperazinyl)pyrazine, Maleate

The title compound was prepared according to the procedure of example 50, step 2, starting from 2-chloro-6-(propargyloxy)pyrazine (1.70 g, 10.1 mmol; obtained according to the procedure of example 50, step 1, starting from propargyl alcohol), piperazine (1.91 g, 22.2 mmol) and $K_2CO_3$ (1.39 g, 10.1 mmol) with the exception that the final filtration through alumina was omitted. Following repeated chromatography on silica, solvents were evaporated off. The yield of the free base of the title compound was 0.48 g (22%) which was obtained as a beige oil. The free base was converted into its maleate salt. HRMS m/z calcd for $C_{11}H_{14}N_4O$ $(M)^+$ 218.1168, found 218.1158. Anal. ($C_{11}H_{14}N_4O\ .C_4H_4O_4$) C, H, N.

Preparation of Pharmaceutical Compositions

Example: Preparation of Tablets

| Ingredients | mg/tablet |
| --- | --- |
| 1. Active compound | 10.0 |
| 2. Cellulose, microcrystalline | 57.0 |
| 3. Calcium hydrogen phosphate | 15.0 |
| 4. Sodium starch glycolate | 5.0 |
| 5. Silicon dioxide, colloidal | 0.25 |
| 6. Magnesium stearate | 0.75 |

The active ingredient 1 is mixed with ingredients 2, 3, 4 and 5 for about 10 minutes. The magnesium stearate is then added, and the resultant mixture is mixed for about 5 minutes and compressed into tablet form with or without film-coating.

Pharmacological Tests

The ability of a compound of the invention to bind or act at specific 5-HT receptor subtypes can be determined using in vitro and in vivo assays known in the art. The biological activity of compounds prepared in the Examples was tested using different tests.

Affinity Assay

The 5-HT$_{2c}$ receptor affinity of compounds in the Examples was determined in competition experiments, where the ability of each compound in serial dilution to displace $^3$H-labelled 5-HT, bound to membranes prepared from a transfected HEK293 cell line stably expressing the human 5-HT$_{2c}$ receptor protein, was monitored by Scintillation Proximity Assay technology. Non-specific binding was defined using 5 μM mianserin. Results obtained for exemplary compounds of the invention are illustrated in Table 1 below. Typically, the 5-HT$_{2c}$ receptor affinity values ($K_i$, nM) were in the range of 1 nM to 1500 nM.

TABLE 1

| 5-HT$_{2c}$ receptor Affinity | |
|---|---|
| Compound | $K_i$ (nM) |
| Example 2 | 8 |
| Example 12 | 197 |
| Example 15 | 616 |
| Example 18 | 92 |
| Example 20 | 28 |
| Example 23 | 478 |
| Example 32 | 48 |
| Example 48 | 37 |

Efficacy Assay

The agonist efficacy at the 5-HT$_{2c}$ receptor of the compounds in the Examples was determined by the ability of each compound to mobilise intracellular calcium in transfected HEK293 cells, stably expressing the human 5-HT$_{2c}$ receptor protein, using the calcium-chelating fluorescent dye FLUO-3 (Sigma, St. Louis, Mo., U.S.A.).

Typically, the maximum responses of 5-HT$_{2c}$ agonists were in the range of 20–100% relative to the maximum response of 5-HT (serotonin) at a concentration of 1 μM.

What is claimed is:

1. A compound of the formula (I):

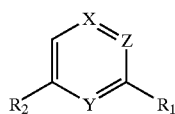

(I)

wherein
(i) X and Y represent both nitrogen and Z represents CH,
R$_1$ and R$_2$ are each, independently, selected from a group A consisting of

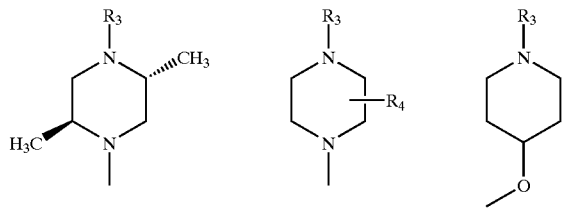

or from a group B, consisting of aryl-C$_1$–C$_6$-alkyl, aryl-C$_1$–C$_6$-alkoxy, heteroaryl-C$_1$–C$_6$-alkoxy, aryloxy-C$_2$–C$_6$-alkoxy, heteroaryloxy-C$_2$–C$_6$-alkoxy, 1-indanyloxy, 2-indanyloxy, aryloxy, heteroaryloxy, arylthio, heteroarylthio, C$_5$–C$_6$-cycloalkylthio, C$_5$–C$_8$-alkoxy, C$_5$–C$_8$-alkylthio, C$_3$–C$_6$-alkynyloxy, C$_3$–C$_6$-alkenyloxy, fluoro-C$_2$–C$_4$-alkoxy, C$_4$–C$_8$-cycloalkyloxy, C$_3$–C$_8$-cycloalkyl-C$_1$–C$_4$-alkoxy, halogen, aryl-C$_1$–C$_4$-alkylthio, heteroaryl-C$_1$–C$_4$alkylthio, aryl-C$_1$–C$_4$-alkylamino, heteroaryl-C$_1$–C$_4$-alkylamino, heteroaryl and aryl;

with the proviso that:
(i) R$_1$ and R$_2$ are different and are not both selected from group A or group B at the same time;
(ii) R$_1$ or R$_2$ are not phenylthio, phenylmethylthio, phenyl or phenyl substituted by halogen;
(iii) R$_1$ in formula (I) is halogen, only when R$_2$ simultaneously is 2-methylpiperazin-1-yl, 2-ethylpiperazin-1-yl, or trans-2,5-dimethylpiperazin-1-yl;
(iv) when R$_1$ is 4-piperidinyloxy, R$_2$ is other than 3-pyridinylmethoxy, 4-quinolinylmethoxy and 3-(4-pyridinyl)propoxy;

and where R$_3$ is H or C$_{1-4}$-alkyl, allyl, 2-hydroxyethyl, 2-cyanoethyl, or a nitrogen protecting group, or a prodrug moiety;

R$_4$ is hydrogen, or C$_{1-4}$ alkyl;

and wherein any aryl or heteroaryl residue, alone or as part of another group, in R$_1$ or R$_2$ may be independently substituted in one or more positions, by C$_{1-4}$-alkyl, C$_{1-4}$-alkoxy, C$_{1-4}$-alkylthio, C$_{2-4}$-acyl, C$_{1-4}$-alkylsulphonyl, cyano, nitro, hydroxy, C$_{2-6}$-alkenyl, C$_{2-6}$-alkynyl, fluoromethyl, trifluoromethyl, trifluoromethoxy, halogen, —N(R$_5$)(R$_6$), aryl, aryloxy, arylthio, aryl-C$_{1-4}$-alkyl, aryl-C$_{2-4}$-alkenyl, aryl-C$_{2-4}$-alkynyl, heteroaryl, heteroaryloxy, heteroarylthio or heteroaryl-C$_{1-4}$-alkyl, aryl-C$_{1-4}$-alkoxy, aryloxy-C$_{1-4}$-alkyl, dimethylamino-C$_{2-4}$-alkoxy; and wherein any aryl or heteroaryl residue as substituents on aryl or heteroaryl, alone or as part of another group, in R$_1$ or R$_2$ in turn may be substituted in one or more postions, independently of each other by C$_{1-4}$-alkyl, C$_{1-4}$-alkoxy, halogen, trifluoromethyl, cyano, hydroxy or dimethylamino; and R$_5$ and R$_6$ independently of each other are hydrogen, methyl or ethyl, or together with the nitrogen atom to which they are bound form a pyrrolidine, piperazine, morpholine, thiomorpholine or a piperidine ring;

or pharmaceutically acceptable salt, hydrate, geometrical isomer, tautomer, optical isomer, N-oxide or prodrug form thereof.

2. The compound according to claim 1 wherein X and Y represent both nitrogen and Z represents CH, forming a pyrazine derivative.

3. The compound according to claim 1 wherein $R_3$ is hydrogen and $R_1$ or $R_2$ is selected from

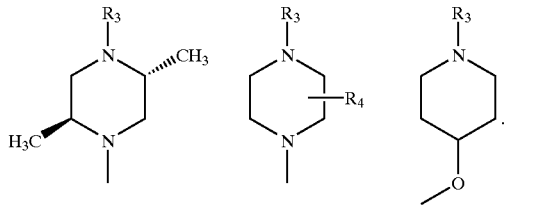

4. The compound according to claim 1 wherein $R_1$ or $R_2$ is selected from

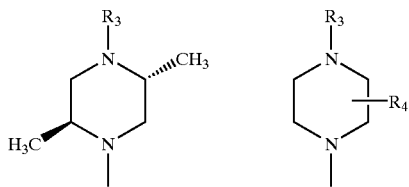

and where $R_3$ is hydrogen and $R_4$ is selected from hydrogen, methyl or ethyl.

5. The compound according to claim 1 wherein $R_1$ or $R_2$ is

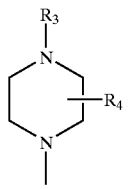

and where $R_3$ is hydrogen and $R_4$ is selected from hydrogen, methyl or ethyl.

6. The compound according to claim 1, wherein $R_1$ or $R_2$ is selected from

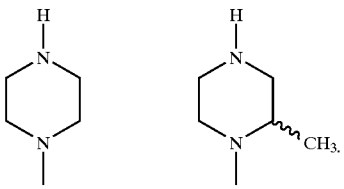

7. The compound according to claim 1 with the general formula (II):

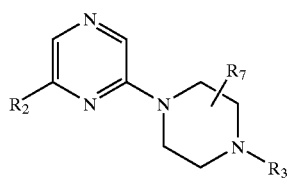

wherein
  $R_2$ and $R_3$ are as defined above;
  $R_7$ is hydrogen or $C_{1-4}$-alkyl;
  and any aryl and heteroaryl residue, alone or as part of another group, in $R_2$ may be substituted in one or more positions, independently of each other by $C_{1-4}$-alkyl, $C_{1-4}$-alkoxy, $C_{1-4}$-alkylthio, $C_{2-4}$-acyl, $C_{1-4}$-alkylsulphonyl, cyano, nitro, hydroxy, $C_{2-6}$-alkenyl, $C_{2-6}$-alkynyl, fluoromethyl, trifluoromethyl, trifluoromethoxy, halogen, —N($R_5$)($R_6$), aryl, aryloxy, arylthio, aryl-$C_{1-4}$-alkyl, aryl-$C_{2-4}$-alkenyl, aryl-$C_{2-4}$-alkynyl, heteroaryl, heteroaryloxy, heteroarylthio or heteroaryl-$C_{1-4}$-alkyl, aryl-$C_{1-4}$-alkoxy, aryloxy-$C_{1-4}$-alkyl, dimethylamino-$C_{2-4}$-alkoxy; and any aryl or heteroaryl residue as substituents on aryl or heteroaryl, alone or as part of another group, in $R_2$ in turn may be substituted in one or more postions, independently of each other by $C_{1-4}$-alkyl, $C_{1-4}$-alkoxy, halogen, trifluoromethyl, cyano, hydroxy or dimethylamino; $R_5$ and $R_6$ are as defined above.

8. The compound according to claim 7 wherein $R_3$ is hydrogen.

9. The compound according to claim 7 wherein $R_7$ is selected from hydrogen, methyl or ethyl.

10. The compound according to claim 7 wherein $R_7$ is methyl and where said methyl is attached to the C2-position of the piperazine ring.

11. The compound according to claim 7 wherein $R_7$ is hydrogen.

12. The compound according to claim 1, which is selected from the group consisting of:

2-(Benzyloxy)-6-(1-piperazinyl)pyrazine,
2-[(2-Methoxybenzyl)oxy]-6-(1-piperazinyl)pyrazine,
2-[(3-Methoxybenzyl)oxy]-6-(1-piperazinyl)pyrazine,
2-[(3,5-Difluorobenzyl)oxy]-6-(1-piperazinyl)pyrazine,
2-(1-Naphthylmethoxy)-6-(1-piperazinyl)pyrazine,
2-(1-Phenylethoxy)-6-(1-piperazinyl)pyrazine,
2-[1-(3-Fluorophenyl)ethoxy]-6-(1-piperazinyl)pyrazine,
2-[1-(2-Methoxyphenyl)ethoxy]-6-(1-piperazinyl)pyrazine,
2-(3,4-Dihydro-2H-chromen-4-yloxy)-6-(1-piperazinyl)pyrazine,
2-(2-Phenylethoxy)-6-(1-piperazinyl)pyrazine,
2-[(2-Phenoxybenzyl)oxy]-6-(1-piperazinyl)pyrazine,
2-[2-(3-chlorophenyl)ethoxy]-6-(1-piperazinyl)pyrazine,
2-[2-(2-Methoxyphenyl)ethoxy]-6-(1-piperazinyl)pyrazine,
2-[2-(3Methoxyphenyl)ethoxy]-6-(1-piperazinyl)pyrazine,
2-[2-(4-Methoxyphenyl)ethoxy]-6-(1-piperazinyl)pyrazine,
2-[2-(2,5-Dimethoxyphenyl)ethoxy]-6-(1-piperazinyl)pyrazine,
2-[(2-Phenylethyl)sulfanyl]-6-(1-piperazinyl)pyrazine,
2-[(5-Fluoro-2-methoxybenzyl)oxy]-6-(1-piperazinyl)pyrazine,
2-[(3-Cyanobenzyl)oxy]-6-(1-piperazinyl)pyrazine,
2-[(2-chlorobenzyl)sulfanyl]-6-(1-piperazinyl)pyrazine,
2-[2-(4-Dimethylaminophenyl)ethoxy]-6-(1-piperazinyl)pyrazine,
2-[2-(1H-Indol-3-yl)ethoxy]-6-(1-piperazinyl)pyrazine,
2-[2-(1 H-Indol-1-yl)ethoxy]-6-(1-piperazinyl)pyrazine,
2-Benzyl-6-(1-piperazinyl)pyrazine,
2-[(3,5-Dimethoxybenzyl)oxy]-6-(1-piperazinyl)pyrazine,
1-[6-(Benzyloxy)-2-pyrazinyl]-2-methylpiperazine, 1-[6-(Benzyloxy)-2-pyrazinyl]-2-ethylpiperazine
1-[6-(Benzyloxy)-2-pyrazinyl]-trans-2,5-dimethylpiperazine.
2-[2-(2-Fluorophenyl)ethoxy]-6-(1-piperazinyl)pyrazine,
2-(2,3-Dihydro-1H-inden-1-ylmethoxy)-6-(1-piperazinyl)pyrazine
2-(4-Phenoxybutoxy)-6-(1-piperazinyl)pyrazine.
2-[(5-Phenoxypentyl)oxy]-6-(1-piperazinyl)pyrazine.
2-[(2,5-Dimethoxybenzyl)oxy]-6-(1-piperazinyl)pyrazine.
2-{[2-(2-Phenylethyl)benzyl]oxy}-6-(1-piperazinyl)pyrazine
(2R)-1-[6-(Benzyloxy)-2-pyrazinyl]-2-methylpiperazine,
2-[2-(2,6-Difluorophenoxy)ethoxy]-6-(1-piperazinyl)pyrazine
2-[2-(2-Naphthyloxy)ethoxy]-6-(1-piperazinyl)pyrazine
2-(1-Methyl-2-phenylethoxy)-6-(1-piperazinyl)pyrazine
2-{[2-(Phenoxymethyl)benzyl]oxy}-6-(1-piperazinyl)pyrazine
2-[(5-Fluoro-2-methoxybenzyl)oxy]-6-(1-piperazinyl)pyrazine
2-[(2,5-Difluorobenzyl)oxy]-6-(1-piperazinyl)pyrazine
2-[(2-Fluorobenzyl)oxy]-6-(1-piperazinyl)pyrazine
2-(Benzo[b]thiophen-3-ylmethoxy)-6-(1-piperazinyl)pyrazine,
2-[2-(5-Methyl-2-phenyl-oxazol-4-yl)-ethoxy]-6-(1-piperazinyl)pyrazine,
2-[1-(2,6-Difluoro-phenyl)-ethoxy]-6-(1-piperazinyl)pyrazine,
2-(2-Naphthalen-2-yl-ethoxy)-6-(1-piperazinyl)pyrazine,
2-[3-(Naphthalen-2-yloxy)-propoxy]-6-(1-piperazinyl)pyrazine,
2-[2-(7-Methoxy-naphthalen-2-yloxy)-ethoxy]-6-(1-piperazinyl)pyrazine,
2-[5-(4-Chlorophenyl)-2-methylfuran-3-ylmethoxy]-6-(1-piperazinyl)pyrazine,
2-(1H-Indol-4-ylmethoxy)-6-(1-piperazinyl)pyrazine,
and their pharmacologically acceptable salts and solvates.

13. A pharmaceutical composition comprising a compound according to claim 1 as an active ingredient, together with a pharmaceutically acceptable carrier.

14. A method for the prophylaxis or treatment of a serotonin-related medical condition, comprising administering to a subject in need thereof a therapeutically effective amount of a compound according to claim 1.

15. The method according to claim 14, wherein the medical condition is related to the 5-HT$_{2c}$ receptor.

16. The method according to claim 14 wherein the medical condition is an eating disorder.

17. The method according to claim 14, wherein the medical condition is obesity.

18. The method according to claim 14, wherein the medical condition a memory disorder.

19. The method according to claim 14, wherein the medical condition is a mood disorder.

20. The method according to claim 14, wherein the medical condition is an anxiety disorder.

21. The method according to claim 14, wherein the medical condition is selected from sexual dysfunctions, epilepsy and urinary disorders.

22. The method according to claim 14, wherein the medical condition is pain.

23. The method according to claim 14, wherein the medical condition is substance abuse.

24. The method according to claim 14, wherein the medical condition is schizophrenia.

25. A method of making a compound of claim 1, taking a compound of the following formula:

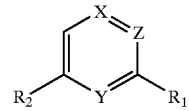

wherein
(i) X and Y represent both nitrogen and Z represents CH,
and R$_2$ are independently a halogen;
and reacting the compound with one or more chemical reagents in one or more steps to produce a compound of claim 1.

26. A method of modulating serotonin in a subject comprising administering to the subject an effective amount of a compound of claim 1.

27. A method of modulating 5-HT$_{2c}$ in a subject comprising administering to the subject an effective amount of a compound of claim 1.

28. The compound according to claim 1, wherein R$_3$ is an acyl- or alkoxycarbonyl group forming a cleavable amide or carbamate linkage.

29. The compound according to claim 7, wherein R$_2$ is substituted in two positions.

30. The compound according to claim 7, wherein R$_2$ is substituted in one position.

* * * * *